(12) United States Patent
Deinhammer et al.

(10) Patent No.: US 10,941,422 B2
(45) Date of Patent: *Mar. 9, 2021

(54) PROCESSES FOR PRODUCING FUEL ETHANOL

(71) Applicant: NOVOZYMES A/S, Bagsvaerd (DK)

(72) Inventors: Randy Deinhammer, Wake Forest, NC (US); Suzanne Clark, Youngsville, NC (US); Mauricio Quiros, Raleigh, NC (US); John Matthews, Louisburg, NC (US); Anne Glud Hjulmand, Raleigh, NC (US); Chee Leong Soong, Raleigh, NC (US); Tomoko Matsui, Chiba (JP); Shinobu Takagi, Chiba (JP)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/407,840

(22) Filed: May 9, 2019

(65) Prior Publication Data

US 2019/0271011 A1 Sep. 5, 2019

Related U.S. Application Data

(63) Continuation of application No. 15/727,952, filed on Oct. 9, 2017, which is a continuation of application No. 13/994,310, filed as application No. PCT/US2011/066559 on Dec. 21, 2011, now Pat. No. 9,816,112.

(60) Provisional application No. 61/556,373, filed on Dec. 2, 2011, provisional application No. 61/426,039, filed on Dec. 22, 2010.

(51) Int. Cl.
| | | |
|---|---|---|
| *C12P 7/06* | (2006.01) | |
| *C12P 19/02* | (2006.01) | |
| *C12P 19/14* | (2006.01) | |
| *C12P 19/20* | (2006.01) | |

(52) U.S. Cl.
CPC .......... *C12P 7/06* (2013.01); *C12Y 302/01001* (2013.01); *C12Y 302/01003* (2013.01); *C12Y 304/24* (2013.01); *C12P 19/02* (2013.01); *C12P 19/14* (2013.01); *C12P 19/20* (2013.01); *Y02E 50/10* (2013.01)

(58) Field of Classification Search
None
See application file for complete search history.

(56) References Cited

U.S. PATENT DOCUMENTS

| 5,756,339 | A | 5/1998 | Mitta |
|---|---|---|---|
| 6,358,726 | B1 | 3/2002 | Takakura |
| 7,601,858 | B2 | 10/2009 | Cantrell |
| 7,608,729 | B2 | 10/2009 | Winsness |
| 8,008,517 | B2 | 8/2011 | Cantrell |
| 8,048,657 | B2 | 11/2011 | Breneman |
| 9,677,095 | B2 | 6/2017 | Deinhammer |
| 9,816,112 | B2 * | 11/2017 | Deinhammer ... C12Y 302/0100 |
| 9,951,364 | B2 | 4/2018 | Kang |
| 10,035,973 | B2 | 7/2018 | Kreel |
| 10,093,882 | B2 | 10/2018 | Clark |
| 2002/0086402 | A1 | 7/2002 | Takakura |
| 2004/0219649 | A1 | 11/2004 | Olsen |
| 2005/0084934 | A1 | 4/2005 | Takakura |
| 2005/0100996 | A1 | 5/2005 | Lantero, Jr. |
| 2007/0178567 | A1 | 8/2007 | Lewis |
| 2007/0184150 | A1 | 8/2007 | Bhargava |
| 2008/0138871 | A1 | 6/2008 | Smith |
| 2009/0227004 | A1 | 9/2009 | Dale |
| 2010/0058649 | A1 | 3/2010 | Bootsma |
| 2012/0040436 | A1 | 2/2012 | Harada |
| 2012/0214197 | A1 | 8/2012 | Landvik |
| 2014/0024064 | A1 | 1/2014 | Burlew |
| 2014/0315243 | A1 | 10/2014 | Deinhammer et al. |

FOREIGN PATENT DOCUMENTS

| DE | 10 2005062984 A1 | 12/2005 |
|---|---|---|
| WO | 92/02614 A1 | 2/1992 |
| WO | 92/20777 A1 | 11/1992 |
| WO | 97/29179 A1 | 8/1997 |
| WO | 99/19467 A1 | 4/1999 |
| WO | 02/074895 A2 | 9/2002 |
| WO | 2004/087889 A1 | 10/2004 |
| WO | 2005/113785 A2 | 12/2005 |
| WO | 2006/087692 A2 | 8/2006 |
| WO | 2007/056321 A1 | 5/2008 |
| WO | 2009/52101 A1 | 4/2009 |
| WO | 2009/100138 A2 | 8/2009 |
| WO | 2010/008841 A2 | 1/2010 |
| WO | 2011/068803 A1 | 6/2011 |
| WO | 2011/72191 A2 | 6/2011 |

(Continued)

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Ben et al, 2010—Uniport Access No. Q9KWY6.
Cheng et al, 2011, Appl Biochem Biotechnol 163(6), 693-706.
Chica et al, 2005, Curr Op Biotechnol 16(4), 378-384.
Maeder et al, 2002, Uniprot accession No. Q8U0C9.

(Continued)

*Primary Examiner* — Christian L Fronda

(74) *Attorney, Agent, or Firm* — David Fazzolare

(57) ABSTRACT

The present invention relates to processes for producing fermentation products from starch-containing material, wherein a thermostable alpha-amylase and optionally a thermostable protease are present and/or added during liquefaction. The invention also relates to a composition suitable for use in a process of the invention.

114 Claims, 5 Drawing Sheets
Specification includes a Sequence Listing.

(56) References Cited

FOREIGN PATENT DOCUMENTS

| WO | 2011/80353 A1 | 7/2011 |
|---|---|---|
| WO | 2011/82425 A2 | 7/2011 |
| WO | 2011/126897 A1 | 10/2011 |
| WO | 2011/127802 A1 | 10/2011 |
| WO | 2012/084225 A1 | 6/2012 |
| WO | 2013/006756 A2 | 1/2013 |
| WO | 2013/082486 A1 | 6/2013 |

OTHER PUBLICATIONS

Sen et al, 2007, Appl Biochem Biotechnol 143(3), 212-223.
Silva et al, 1998, Uniprot accession No. O31193.
Singh et al, 2017, Current protein and peptide science 18, 1-11.
Case No. IPR2020-00464, U.S. Pat. No. 7,820,419 dated Jan. 27, 2020.
Declaration of Douglas S. Clark, Ph.D. For IPR 2020-00464 dated Jan. 25, 2020.
Goode et al., Optimization of Mashing Conditions when Mashing with Unmalted Sorghum and Commercial Enzymes, 61 J. Am. Soc. Brew. Chem. 69-78 (2003).
K.C. Thomas & W.M. Ingledew, Fuel Alcohol Production: Effects of Free Amino Nitrogen on Fermentation of Very-High-Gravity Wheat Mashes, 56 Appl. Environ. Microbiology 2046-2050 (1990).
B. T. Little, Alternative Cereals for Beer Production, 7 Ferment 163-168 (1994).
The Alcohol Textbook, Foreword, Chapters 1, 2, 14, 15 (K.A. Jacques et al., eds., 4th ed. 2003).
Declaration of Dr. Vijay Singh dated Feb. 24, 2019.
Anonymous, 2006-2007, Biochemicals, reagents and kits of life science research.
Anonymous, 2019, Danisco petition fro inter partes review of U.S. Appl. No. 10/035,973.
Brock, 1967, Science 158(3804), 1012-1019.
Bruins et al, 2001, Appl Biochem Biotechnol 90, 155-186.
Connaris et al, 1991, J Gen Microbiol 137, 1193-1199.
Gray et al, 1986, Uniprot access No. P00799.
Katrolia et al, 2012, Bioresource Technology 110, 578-586.
Kristjansson et al, 1990, Biochem J 270, 51-55.
Lao et al, 1996, Appl Environ Microbiol 62(11), 4256-4259.
Lao et al, 1998, Uniprot access No. O86984.
Li (Ed), 2010, Tianjin Science and Technology Translation Publishing Company, 26-28—English translation attached.
Majoni et al, 2011, JAOCS 88(4) 523-532.
Niehaus et al, 1999, Appl Microbiol Biotechnol 51, 711-729.
Perez-Carillo et al, 2012, Biochem Eng J 67, 1-9.
Prakash et al, 2013, Biomed research international, Article ID 264020, 1-8.
Qi, 2011, Zhengzhou university press, 118-119—English translation attached.
Sun et al, 2013, Food Safety 34(2), 72-77.
Vielle et al, 2001, Microbiol Mol Biol Revs 65(1), 1-43.
Wang et al, 2009, J Agric Food Chem 57, 2302-2307.
Wang, 2008, Lipid technology 20(9), 203-207.
Ward et al, 2002, Archaea 1, 63-74.
Yang (Ed), 2013, Industrial patent analysis report, Intellectual property press 16, 79—English translation attached.
Yao et al, 2014, Journal of bioprocess engineering and biorefinery 3, 323-331.
Zheng (Ed), 2003, Science and Technology Literature Press, 96—English translation attached.
Zheng (Ed), 2009, Zhongshan University Press, 315—English translation attached.
U.S. Appl. No. 10/035,973—PTAB decision granting IPR petition.
WO 2003-048353 A1—Access No. ABR62336.
WO 2011-127802 A1—Accession No. AZN72409.
U.S. Office Actions from related application U.S. Appl. No. 14/362,002 dated May 24, 2016; Jan. 17, 2017; Mar. 9, 2018; Sep. 19, 2018 and Sep. 9, 2019.
IPR 2020-00464 re Patent 7,820,419 B2—Institution Decision dated Jul. 28, 2020.

\* cited by examiner

SEQUENCE LISTING

```
<160> NUMBER OF SEQ ID NOS: 14

<210> SEQ ID NO 1
<211> LENGTH: 515
<212> TYPE: PRT
<213> ORGANISM: Bacillus stearothermophilus
<220> FEATURE:
<221> NAME/KEY: mat_peptide
<222> LOCATION: (1)..(515)

<400> SEQUENCE: 1
```

```
Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
            115                 120                 125

Glu Ile Ser Gly Thr Tyr Gln Ile Gln Ala Trp Thr Lys Phe Asp Phe
130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
            165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
            195                 200                 205

Pro Glu Val Val Thr Glu Leu Lys Asn Trp Gly Lys Trp Tyr Val Asn
            210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
            245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
            275                 280                 285

Ala Pro Leu His Asn Lys Phe Tyr Thr Ala Ser Lys Ser Gly Gly Ala
            290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
            325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
            370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
            405                 410                 415
```

-continued

```
Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515

<210> SEQ ID NO 2
<211> LENGTH: 1068
<212> TYPE: DNA
<213> ORGANISM: Thermoascus aurantiacus
<220> FEATURE:
<221> NAME/KEY: CDS
<222> LOCATION: (1)..(1065)
<220> FEATURE:
<221> NAME/KEY: misc_signal
<222> LOCATION: (1)..(57)
<220> FEATURE:
<221> NAME/KEY: misc_feature
<222> LOCATION: (58)..(534)
<220> FEATURE:
<221> NAME/KEY: mat_peptide
<222> LOCATION: (535)..(1068)

<400> SEQUENCE: 2 atg cgg ctc gtt gct tcc cta acg gcc ttg gtg gcc ttg tcc gta        45
Met Arg Leu Val Ala Ser Leu Thr Ala Leu Val Ala Leu Ser Val
        -175                -170                -165 cct gtc ttt ccc gct gct gtc aac gtg aag cgt gct tcg tcc tac        90
Pro Val Phe Pro Ala Ala Val Asn Val Lys Arg Ala Ser Ser Tyr
    -160                -155                -150 ctg gag atc act ctg agc cag gtc agc aac act ctg atc aag gcc       135
Leu Glu Ile Thr Leu Ser Gln Val Ser Asn Thr Leu Ile Lys Ala
-145                -140                -135 gtg gtc cag aac act ggt agc gac gag ttg tcc ttc gtt cac ctg       180
Val Val Gln Asn Thr Gly Ser Asp Glu Leu Ser Phe Val His Leu
        -130                -125                -120 aac ttc ttc aag gac ccc gct cct gtc aaa aag gta tcg gtc tat       225
Asn Phe Phe Lys Asp Pro Ala Pro Val Lys Lys Val Ser Val Tyr
    -115                -110                -105 cgc gat ggg tct gaa gtg cag ttc gag ggc att ttg agc cgc tac aaa   273
Arg Asp Gly Ser Glu Val Gln Phe Glu Gly Ile Leu Ser Arg Tyr Lys
-100                -95                  -90 tcg act ggc ctc tct cgt gac gcc ttt act tat ctg gct ccc gga gag   321
Ser Thr Gly Leu Ser Arg Asp Ala Phe Thr Tyr Leu Ala Pro Gly Glu
        -85                 -80                 -75 tcc gtc gag gac gtt ttt gat att gct tcg act tac gat ctg acc agc   369
Ser Val Glu Asp Val Phe Asp Ile Ala Ser Thr Tyr Asp Leu Thr Ser
    -70                 -65                 -60 ggc ggc cct gta act atc cgt act gag gga gtt gtt ccc tac gcc acg   417
Gly Gly Pro Val Thr Ile Arg Thr Glu Gly Val Val Pro Tyr Ala Thr
-55                 -50                 -45                 -40 gct aac agc act gat att gcc ggc tac atc tca tac tcg tct aat gtg   465
Ala Asn Ser Thr Asp Ile Ala Gly Tyr Ile Ser Tyr Ser Ser Asn Val
```

```
                -35             -30             -25
ttg acc att gat gtc gat ggc gcc gct gct gcc act gtc tcc aag gca    513
Leu Thr Ile Asp Val Asp Gly Ala Ala Ala Ala Thr Val Ser Lys Ala
        -20             -15             -10 atc act cct ttg gac cgc cgc act agg atc agt tcc tgc tcc ggc agc    561
Ile Thr Pro Leu Asp Arg Arg Thr Arg Ile Ser Ser Cys Ser Gly Ser
         -5             -1   1                 5 aga cag agc gct ctt act acg gct ctc aga aac gct gct tct ctt gcc    609
Arg Gln Ser Ala Leu Thr Thr Ala Leu Arg Asn Ala Ala Ser Leu Ala
 10              15              20              25 aac gca gct gcc gac gcg gct cag tct gga tca gct tca aag ttc agc    657
Asn Ala Ala Ala Asp Ala Ala Gln Ser Gly Ser Ala Ser Lys Phe Ser
             30              35              40 gag tac ttc aag act act tct agc tct acc cgc cag acc gtg gct gcg    705
Glu Tyr Phe Lys Thr Thr Ser Ser Ser Thr Arg Gln Thr Val Ala Ala
         45              50              55 cgt ctt cgg gct gtt gcg cgg gag gca tct tcg tct tct tcg gga gcc    753
Arg Leu Arg Ala Val Ala Arg Glu Ala Ser Ser Ser Ser Ser Gly Ala
         60              65              70 acc acg tac tac tgc gac gat ccc tac ggc tac tgt tcc tcc aac gtc    801
Thr Thr Tyr Tyr Cys Asp Asp Pro Tyr Gly Tyr Cys Ser Ser Asn Val
 75              80              85 ctg gct tac acc ctg cct tca tac aac ata atc gcc aac tgt gac att    849
Leu Ala Tyr Thr Leu Pro Ser Tyr Asn Ile Ile Ala Asn Cys Asp Ile
 90              95              100             105 ttc tat act tac ctg ccg gct ctg acc agt acc tgt cac gct cag gat    897
Phe Tyr Thr Tyr Leu Pro Ala Leu Thr Ser Thr Cys His Ala Gln Asp
             110             115             120 caa gcg acc act gcc ctt cac gag ttc acc cat gcc cct ggc gtc tac    945
Gln Ala Thr Thr Ala Leu His Glu Phe Thr His Ala Pro Gly Val Tyr
         125             130             135 agc cct ggc acg gac gac ctg gcg tat ggc tac cag gct gcg atg ggt    993
Ser Pro Gly Thr Asp Asp Leu Ala Tyr Gly Tyr Gln Ala Ala Met Gly
         140             145             150 ctc agc agc agc cag gct gtc atg aac gct gac acc tac gct ctc tat   1041
Leu Ser Ser Ser Gln Ala Val Met Asn Ala Asp Thr Tyr Ala Leu Tyr
 155             160             165 gcg aat gcc ata tac ctt ggt tgc taa                                1068
Ala Asn Ala Ile Tyr Leu Gly Cys
 170             175

<210> SEQ ID NO 3
<211> LENGTH: 355
<212> TYPE: PRT
<213> ORGANISM: Thermoascus aurantiacus

<400> SEQUENCE: 3

Met Arg Leu Val  Ala Ser Leu Thr Ala  Leu Val Ala Leu Ser  Val
        -175             -170              -165

Pro Val Phe Pro  Ala Ala Val Asn Val  Lys Arg Ala Ser Ser  Tyr
        -160             -155              -150

Leu Glu Ile Thr  Leu Ser Gln Val Ser  Asn Thr Leu Ile Lys  Ala
        -145             -140              -135

Val Val Gln Asn  Thr Gly Ser Asp Glu  Leu Ser Phe Val His  Leu
        -130             -125              -120

Asn Phe Phe Lys  Asp Pro Ala Pro Val  Lys Lys Val Ser Val  Tyr
        -115             -110              -105

Arg Asp Gly Ser  Glu Val Gln Phe Glu  Gly Ile Leu Ser Arg Tyr  Lys
        -100              -95               -90
```

Ser Thr Gly Leu Ser Arg Asp Ala Phe Thr Tyr Leu Ala Pro Gly Glu
        -85                 -80                 -75

Ser Val Glu Asp Val Phe Asp Ile Ala Ser Thr Tyr Asp Leu Thr Ser
    -70                 -65                 -60

Gly Gly Pro Val Thr Ile Arg Thr Glu Gly Val Val Pro Tyr Ala Thr
-55                 -50                 -45                 -40

Ala Asn Ser Thr Asp Ile Ala Gly Tyr Ile Ser Tyr Ser Ser Asn Val
            -35                 -30                 -25

Leu Thr Ile Asp Val Asp Gly Ala Ala Ala Thr Val Ser Lys Ala
            -20                 -15                 -10

Ile Thr Pro Leu Asp Arg Arg Thr Arg Ile Ser Ser Cys Ser Gly Ser
        -5                  -1  1                5

Arg Gln Ser Ala Leu Thr Thr Ala Leu Arg Asn Ala Ala Ser Leu Ala
10                  15                  20                  25

Asn Ala Ala Ala Asp Ala Ala Gln Ser Gly Ser Ala Ser Lys Phe Ser
            30                  35                  40

Glu Tyr Phe Lys Thr Thr Ser Ser Thr Arg Gln Thr Val Ala Ala
            45                  50                  55

Arg Leu Arg Ala Val Ala Arg Glu Ala Ser Ser Ser Ser Gly Ala
    60                  65                  70

Thr Thr Tyr Tyr Cys Asp Asp Pro Tyr Gly Tyr Cys Ser Ser Asn Val
75                  80                  85

Leu Ala Tyr Thr Leu Pro Ser Tyr Asn Ile Ile Ala Asn Cys Asp Ile
90                  95                  100                 105

Phe Tyr Thr Tyr Leu Pro Ala Leu Thr Ser Thr Cys His Ala Gln Asp
                110                 115                 120

Gln Ala Thr Thr Ala Leu His Glu Phe Thr His Ala Pro Gly Val Tyr
            125                 130                 135

Ser Pro Gly Thr Asp Asp Leu Ala Tyr Gly Tyr Gln Ala Ala Met Gly
            140                 145                 150

Leu Ser Ser Ser Gln Ala Val Met Asn Ala Asp Thr Tyr Ala Leu Tyr
            155                 160                 165

Ala Asn Ala Ile Tyr Leu Gly Cys
170                 175

<210> SEQ ID NO 4
<211> LENGTH: 49
<212> TYPE: DNA
<213> ORGANISM: Artificial Sequence
<220> FEATURE:
<223> OTHER INFORMATION: Synthetic Construct

<400> SEQUENCE: 4
aacgacggta cccgggggatc ggatccatgc ggctcgttgc ttccctaac                49

<210> SEQ ID NO 5
<211> LENGTH: 48
<212> TYPE: DNA
<213> ORGANISM: Artificial Sequence
<220> FEATURE:
<223> OTHER INFORMATION: Artificial Construct

<400> SEQUENCE: 5
ctaattacat gatgcggccc ttaattaatt agcaaccaag gtatatgg                 48

<210> SEQ ID NO 6
<211> LENGTH: 20

```
<212> TYPE: DNA
<213> ORGANISM: Artificial Sequence
<220> FEATURE:
<223> OTHER INFORMATION: Artificial Construct

<400> SEQUENCE: 6
taggagttta gtgaacttgc                                                     20

<210> SEQ ID NO 7
<211> LENGTH: 18
<212> TYPE: DNA
<213> ORGANISM: Artificial Sequence
<220> FEATURE:
<223> OTHER INFORMATION: Artificial Construct

<400> SEQUENCE: 7
ttcgagcgtc ccaaaacc                                                       18

<210> SEQ ID NO 8
<211> LENGTH: 1851
<212> TYPE: DNA
<213> ORGANISM: Penicillium oxalicum
<220> FEATURE:
<221> NAME/KEY: CDS
<222> LOCATION: (1)..(1851)

<400> SEQUENCE: 8 atg cgt ctc act cta tta tca ggt gta gcc ggc gtt ctc tgc gca gga        48
Met Arg Leu Thr Leu Leu Ser Gly Val Ala Gly Val Leu Cys Ala Gly
1               5                   10                  15 cag ctg acg gcg gcg cgt cct gat ccc aag ggt ggg aat ctg acg ccg        96
Gln Leu Thr Ala Ala Arg Pro Asp Pro Lys Gly Gly Asn Leu Thr Pro
                20                  25                  30 ttc atc cac aaa gag ggc gag cgg tcg ctc caa ggc atc ttg gac aat       144
Phe Ile His Lys Glu Gly Glu Arg Ser Leu Gln Gly Ile Leu Asp Asn
            35                  40                  45 ctc ggt ggg cga ggt aag aaa aca ccc ggc act gcc gca ggg ttg ttt       192
Leu Gly Gly Arg Gly Lys Lys Thr Pro Gly Thr Ala Ala Gly Leu Phe
        50                  55                  60 att gcc agt cca aac aca gag aat cca aac tat tat tat aca tgg act       240
Ile Ala Ser Pro Asn Thr Glu Asn Pro Asn Tyr Tyr Tyr Thr Trp Thr
65                  70                  75                  80 cgt gac tca gct ttg act gcc aag tgc ttg atc gac ctg ttc gaa gac       288
Arg Asp Ser Ala Leu Thr Ala Lys Cys Leu Ile Asp Leu Phe Glu Asp
                85                  90                  95 tct cgg gca aag ttt cca att gac cgc aaa tac ttg gaa aca gga att       336
Ser Arg Ala Lys Phe Pro Ile Asp Arg Lys Tyr Leu Glu Thr Gly Ile
                100                 105                 110 cgg gac tac gtg tcg tcc caa gca atc ctc cag agt gtg tct aat cct       384
Arg Asp Tyr Val Ser Ser Gln Ala Ile Leu Gln Ser Val Ser Asn Pro
            115                 120                 125 tct gga acc ctg aag gat ggc tct ggt ctg ggt gaa ccc aag ttt gag       432
Ser Gly Thr Leu Lys Asp Gly Ser Gly Leu Gly Glu Pro Lys Phe Glu
        130                 135                 140 att gac ctg aat ccc ttt tcg ggt gcc tgg ggt cgg cct cag cgg gat       480
Ile Asp Leu Asn Pro Phe Ser Gly Ala Trp Gly Arg Pro Gln Arg Asp
145                 150                 155                 160 ggc cca gcg ctg cga gcg acc gct atg atc acc tac gcc aac tac ctg       528
Gly Pro Ala Leu Arg Ala Thr Ala Met Ile Thr Tyr Ala Asn Tyr Leu
                165                 170                 175 ata tcc cat ggt cag aaa tcg gat gtg tca cag gtc atg tgg ccg att       576
Ile Ser His Gly Gln Lys Ser Asp Val Ser Gln Val Met Trp Pro Ile
            180                 185                 190
```

```
att gcc aat gat cta gca tat gtt ggt caa tac tgg aat aat acc gga    624
Ile Ala Asn Asp Leu Ala Tyr Val Gly Gln Tyr Trp Asn Asn Thr Gly
        195                 200                 205 ttt gac ctg tgg gaa gag gtg gat ggg tca agc ttt ttc acg att gcg    672
Phe Asp Leu Trp Glu Glu Val Asp Gly Ser Ser Phe Phe Thr Ile Ala
    210                 215                 220 gtc cag cac cga gcc ctt gtt gaa ggc tcg caa ctg gcg aaa aag ctc    720
Val Gln His Arg Ala Leu Val Glu Gly Ser Gln Leu Ala Lys Lys Leu
225                 230                 235                 240 ggc aag tcc tgc gat gcc tgt gat tct cag cct ccc cag ata ttg tgt    768
Gly Lys Ser Cys Asp Ala Cys Asp Ser Gln Pro Pro Gln Ile Leu Cys
                245                 250                 255 ttc ctg cag agt ttc tgg aac gga aag tac atc acc tcc aac atc aac    816
Phe Leu Gln Ser Phe Trp Asn Gly Lys Tyr Ile Thr Ser Asn Ile Asn
            260                 265                 270 acg caa gca agc cgc tct ggt atc gac ctg gac tct gtc ctg gga agc    864
Thr Gln Ala Ser Arg Ser Gly Ile Asp Leu Asp Ser Val Leu Gly Ser
        275                 280                 285 att cat acc ttt gat ccc gaa gca gcc tgt gac gat gca act ttc cag    912
Ile His Thr Phe Asp Pro Glu Ala Ala Cys Asp Asp Ala Thr Phe Gln
    290                 295                 300 cct tgt tct gcc cgc gct ctg gcg aac cac aag gtc tat gtg gat tcc    960
Pro Cys Ser Ala Arg Ala Leu Ala Asn His Lys Val Tyr Val Asp Ser
305                 310                 315                 320 ttc cgc tct atc tac aag att aat gcg ggt ctt gca gag gga tcg gct   1008
Phe Arg Ser Ile Tyr Lys Ile Asn Ala Gly Leu Ala Glu Gly Ser Ala
                325                 330                 335 gcc aac gtt ggc cgc tac ccc gag gat gtt tac caa gga ggc aat cca   1056
Ala Asn Val Gly Arg Tyr Pro Glu Asp Val Tyr Gln Gly Gly Asn Pro
            340                 345                 350 tgg tat ctc gcc acc cta ggc gca tct gaa ttg ctt tac gac gcc ttg   1104
Trp Tyr Leu Ala Thr Leu Gly Ala Ser Glu Leu Leu Tyr Asp Ala Leu
        355                 360                 365 tac cag tgg gac aga ctt ggc aaa ctt gaa gtc tcg gag acc tcg ttg   1152
Tyr Gln Trp Asp Arg Leu Gly Lys Leu Glu Val Ser Glu Thr Ser Leu
    370                 375                 380 tca ttc ttc aaa gac ttt gac gcg acc gtg aaa att ggc tcg tac tcg   1200
Ser Phe Phe Lys Asp Phe Asp Ala Thr Val Lys Ile Gly Ser Tyr Ser
385                 390                 395                 400 agg aac agc aag acc tac aag aaa ttg acc cag tcc atc aag tcg tac   1248
Arg Asn Ser Lys Thr Tyr Lys Lys Leu Thr Gln Ser Ile Lys Ser Tyr
                405                 410                 415 gcg gac ggg ttc atc cag tta gtg cag cag tac act cct tct aat gga   1296
Ala Asp Gly Phe Ile Gln Leu Val Gln Gln Tyr Thr Pro Ser Asn Gly
            420                 425                 430 tct ctg gcc gag caa tac gat cgc aat acg gct gct cct ctc tct gca   1344
Ser Leu Ala Glu Gln Tyr Asp Arg Asn Thr Ala Ala Pro Leu Ser Ala
        435                 440                 445 aac gat ctg act tgg tca ttt gcc tct ttc ttg acg gct acg caa cgc   1392
Asn Asp Leu Thr Trp Ser Phe Ala Ser Phe Leu Thr Ala Thr Gln Arg
    450                 455                 460 cgc gat gcc gtg gtt cct ccc tcc tgg ggc gca aag tcg gca aac aaa   1440
Arg Asp Ala Val Val Pro Pro Ser Trp Gly Ala Lys Ser Ala Asn Lys
465                 470                 475                 480 gtc cca acc act tgt tca gcc tcc cct gtt gtg ggt act tat aag gcg   1488
Val Pro Thr Thr Cys Ser Ala Ser Pro Val Val Gly Thr Tyr Lys Ala
                485                 490                 495 ccc acg gca act ttc tca tcc aag act aag tgc gtc ccc gct aaa gat   1536
Pro Thr Ala Thr Phe Ser Ser Lys Thr Lys Cys Val Pro Ala Lys Asp
```

```
                         500                 505                 510
att gtg cct atc acg ttc tac ctg att gag aac act tac tat gga gag    1584
Ile Val Pro Ile Thr Phe Tyr Leu Ile Glu Asn Thr Tyr Tyr Gly Glu
        515                 520                 525 aac gtc ttc atg agt ggc aac att act gcg ctg ggt aac tgg gac gcc    1632
Asn Val Phe Met Ser Gly Asn Ile Thr Ala Leu Gly Asn Trp Asp Ala
    530                 535                 540 aag aaa ggc ttc cca ctc acc gca aac ctc tac acg caa gat caa aac    1680
Lys Lys Gly Phe Pro Leu Thr Ala Asn Leu Tyr Thr Gln Asp Gln Asn
545                 550                 555                 560 ttg tgg ttc gcc agt gtc gag ttc atc cca gca ggc aca ccc ttt gag    1728
Leu Trp Phe Ala Ser Val Glu Phe Ile Pro Ala Gly Thr Pro Phe Glu
                565                 570                 575 tac aag tac tac aag gtc gag ccc aat ggc gat att act tgg gag aag    1776
Tyr Lys Tyr Tyr Lys Val Glu Pro Asn Gly Asp Ile Thr Trp Glu Lys
            580                 585                 590 ggt ccc aac cgg gtg ttc gtc gct ccc acg gga tgc cca gtt cag cct    1824
Gly Pro Asn Arg Val Phe Val Ala Pro Thr Gly Cys Pro Val Gln Pro
        595                 600                 605 cac tcc aac gac gtg tgg cag ttt tga                                1851
His Ser Asn Asp Val Trp Gln Phe
    610                 615

<210> SEQ ID NO 9
<211> LENGTH: 616
<212> TYPE: PRT
<213> ORGANISM: Penicillium oxalicum

<400> SEQUENCE: 9

Met Arg Leu Thr Leu Leu Ser Gly Val Ala Gly Val Leu Cys Ala Gly
1               5                   10                  15

Gln Leu Thr Ala Ala Arg Pro Asp Pro Lys Gly Gly Asn Leu Thr Pro
            20                  25                  30

Phe Ile His Lys Glu Gly Glu Arg Ser Leu Gln Gly Ile Leu Asp Asn
        35                  40                  45

Leu Gly Gly Arg Gly Lys Lys Thr Pro Gly Thr Ala Ala Gly Leu Phe
    50                  55                  60

Ile Ala Ser Pro Asn Thr Glu Asn Pro Asn Tyr Tyr Tyr Thr Trp Thr
65                  70                  75                  80

Arg Asp Ser Ala Leu Thr Ala Lys Cys Leu Ile Asp Leu Phe Glu Asp
                85                  90                  95

Ser Arg Ala Lys Phe Pro Ile Asp Arg Lys Tyr Leu Glu Thr Gly Ile
            100                 105                 110

Arg Asp Tyr Val Ser Ser Gln Ala Ile Leu Gln Ser Val Ser Asn Pro
        115                 120                 125

Ser Gly Thr Leu Lys Asp Gly Ser Gly Leu Gly Glu Pro Lys Phe Glu
    130                 135                 140

Ile Asp Leu Asn Pro Phe Ser Gly Ala Trp Gly Arg Pro Gln Arg Asp
145                 150                 155                 160

Gly Pro Ala Leu Arg Ala Thr Ala Met Ile Thr Tyr Ala Asn Tyr Leu
                165                 170                 175

Ile Ser His Gly Gln Lys Ser Asp Val Ser Gln Val Met Trp Pro Ile
            180                 185                 190

Ile Ala Asn Asp Leu Ala Tyr Val Gly Gln Tyr Trp Asn Asn Thr Gly
        195                 200                 205

Phe Asp Leu Trp Glu Glu Val Asp Gly Ser Ser Phe Phe Thr Ile Ala
    210                 215                 220
```

```
Val Gln His Arg Ala Leu Val Glu Gly Ser Gln Leu Ala Lys Lys Leu
225                 230                 235                 240

Gly Lys Ser Cys Asp Ala Cys Asp Ser Gln Pro Gln Ile Leu Cys
            245                 250                 255

Phe Leu Gln Ser Phe Trp Asn Gly Lys Tyr Ile Thr Ser Asn Ile Asn
        260                 265                 270

Thr Gln Ala Ser Arg Ser Gly Ile Asp Leu Asp Ser Val Leu Gly Ser
            275                 280                 285

Ile His Thr Phe Asp Pro Glu Ala Ala Cys Asp Ala Thr Phe Gln
290                 295                 300

Pro Cys Ser Ala Arg Ala Leu Ala Asn His Lys Val Tyr Val Asp Ser
305                 310                 315                 320

Phe Arg Ser Ile Tyr Lys Ile Asn Ala Gly Leu Ala Glu Gly Ser Ala
                325                 330                 335

Ala Asn Val Gly Arg Tyr Pro Glu Asp Val Tyr Gln Gly Gly Asn Pro
            340                 345                 350

Trp Tyr Leu Ala Thr Leu Gly Ala Ser Glu Leu Leu Tyr Asp Ala Leu
        355                 360                 365

Tyr Gln Trp Asp Arg Leu Gly Lys Leu Glu Val Ser Glu Thr Ser Leu
370                 375                 380

Ser Phe Phe Lys Asp Phe Asp Ala Thr Val Lys Ile Gly Ser Tyr Ser
385                 390                 395                 400

Arg Asn Ser Lys Thr Tyr Lys Lys Leu Thr Gln Ser Ile Lys Ser Tyr
                405                 410                 415

Ala Asp Gly Phe Ile Gln Leu Val Gln Tyr Thr Pro Ser Asn Gly
            420                 425                 430

Ser Leu Ala Glu Gln Tyr Asp Arg Asn Thr Ala Ala Pro Leu Ser Ala
        435                 440                 445

Asn Asp Leu Thr Trp Ser Phe Ala Ser Phe Leu Thr Ala Thr Gln Arg
        450                 455                 460

Arg Asp Ala Val Val Pro Pro Ser Trp Gly Ala Lys Ser Ala Asn Lys
465                 470                 475                 480

Val Pro Thr Thr Cys Ser Ala Ser Pro Val Gly Tyr Lys Ala
                485                 490                 495

Pro Thr Ala Thr Phe Ser Ser Lys Thr Lys Cys Val Pro Ala Lys Asp
            500                 505                 510

Ile Val Pro Ile Thr Phe Tyr Leu Ile Glu Asn Thr Tyr Gly Glu
            515                 520                 525

Asn Val Phe Met Ser Gly Asn Ile Thr Ala Leu Gly Asn Trp Asp Ala
        530                 535                 540

Lys Lys Gly Phe Pro Leu Thr Ala Asn Leu Tyr Thr Gln Asp Gln Asn
545                 550                 555                 560

Leu Trp Phe Ala Ser Val Glu Phe Ile Pro Ala Gly Thr Pro Phe Glu
            565                 570                 575

Tyr Lys Tyr Tyr Lys Val Glu Pro Asn Gly Asp Ile Thr Trp Glu Lys
            580                 585                 590

Gly Pro Asn Arg Val Phe Val Ala Pro Thr Gly Cys Pro Val Gln Pro
            595                 600                 605

His Ser Asn Asp Val Trp Gln Phe
610                 615

<210> SEQ ID NO 10
<211> LENGTH: 4014
```

```
<212> TYPE: DNA
<213> ORGANISM: Thermococcus hydrothermalis
<220> FEATURE:
<221> NAME/KEY: CDS
<222> LOCATION: (1)..(4011)
<220> FEATURE:
<221> NAME/KEY: misc_signal
<222> LOCATION: (1)..(81)
<220> FEATURE:
<221> NAME/KEY: mat_peptide
<222> LOCATION: (82)..(4014)

<400> SEQUENCE: 10
```

| | | | | | | | | | | | | | | | | |
|---|---|---|---|---|---|---|---|---|---|---|---|---|---|---|---|---|
| atg | agg | cgg | gtg | gtt | gcc | ctc | ttc | att | gca | att | ttg | atg | ctt | gga | agc | 48 |
| Met | Arg | Arg | Val | Val | Ala | Leu | Phe | Ile | Ala | Ile | Leu | Met | Leu | Gly | Ser | |
| | -25 | | | | -20 | | | | | -15 | | | | | | |
| atc | gtt | gga | gcg | aac | gtt | aag | agc | gtt | ggc | gcg | gcg | gag | ccg | aag | ccg | 96 |
| Ile | Val | Gly | Ala | Asn | Val | Lys | Ser | Val | Gly | Ala | Ala | Glu | Pro | Lys | Pro | |
| -10 | | | | | -5 | | | | | -1 | 1 | | | | 5 | |
| ctc | aac | gtc | ata | ata | gtc | tgg | cac | cag | cac | cag | ccc | tac | tac | tac | gac | 144 |
| Leu | Asn | Val | Ile | Ile | Val | Trp | His | Gln | His | Gln | Pro | Tyr | Tyr | Tyr | Asp | |
| | | | 10 | | | | | 15 | | | | | 20 | | | |
| cct | gtc | cag | gac | gtc | tac | acc | agg | ccc | tgg | gtc | agg | ctc | cac | gcg | gcg | 192 |
| Pro | Val | Gln | Asp | Val | Tyr | Thr | Arg | Pro | Trp | Val | Arg | Leu | His | Ala | Ala | |
| | | 25 | | | | | 30 | | | | | 35 | | | | |
| aac | aac | tac | tgg | aag | atg | gcc | cac | tac | ctg | agc | cag | tac | ccg | gag | gtt | 240 |
| Asn | Asn | Tyr | Trp | Lys | Met | Ala | His | Tyr | Leu | Ser | Gln | Tyr | Pro | Glu | Val | |
| | 40 | | | | | 45 | | | | | 50 | | | | | |
| cac | gcc | acc | att | gac | ctc | tcg | ggt | tcg | ctg | ata | gcc | cag | ctt | gcc | gac | 288 |
| His | Ala | Thr | Ile | Asp | Leu | Ser | Gly | Ser | Leu | Ile | Ala | Gln | Leu | Ala | Asp | |
| | 55 | | | | | 60 | | | | | 65 | | | | | |
| tac | atg | aac | ggc | aag | aag | gac | acc | tac | cag | ata | atc | acc | gag | aag | ata | 336 |
| Tyr | Met | Asn | Gly | Lys | Lys | Asp | Thr | Tyr | Gln | Ile | Ile | Thr | Glu | Lys | Ile | |
| 70 | | | | | 75 | | | | | 80 | | | | | 85 | |
| gcc | aac | ggg | gaa | ccc | ctc | acc | gtc | gac | gag | aag | tgg | ttc | atg | ctc | cag | 384 |
| Ala | Asn | Gly | Glu | Pro | Leu | Thr | Val | Asp | Glu | Lys | Trp | Phe | Met | Leu | Gln | |
| | | | | 90 | | | | | 95 | | | | | 100 | | |
| gca | ccg | gga | ggg | ttc | ttc | gac | aac | acc | atc | ccc | tgg | aac | ggt | gaa | ccg | 432 |
| Ala | Pro | Gly | Gly | Phe | Phe | Asp | Asn | Thr | Ile | Pro | Trp | Asn | Gly | Glu | Pro | |
| | | 105 | | | | | 110 | | | | | 115 | | | | |
| ata | acc | gac | ccc | aac | ggc | aac | ccg | ata | agg | gac | ttc | tgg | gac | cgc | tac | 480 |
| Ile | Thr | Asp | Pro | Asn | Gly | Asn | Pro | Ile | Arg | Asp | Phe | Trp | Asp | Arg | Tyr | |
| | 120 | | | | | 125 | | | | | 130 | | | | | |
| acg | gag | ctg | aag | aac | aag | atg | ctc | agc | gca | aag | gcc | aag | tac | gca | aac | 528 |
| Thr | Glu | Leu | Lys | Asn | Lys | Met | Leu | Ser | Ala | Lys | Ala | Lys | Tyr | Ala | Asn | |
| | 135 | | | | | 140 | | | | | 145 | | | | | |
| ttc | gtg | act | gag | agc | cag | aag | gtc | gct | gtg | acg | aac | gag | ttc | aca | gag | 576 |
| Phe | Val | Thr | Glu | Ser | Gln | Lys | Val | Ala | Val | Thr | Asn | Glu | Phe | Thr | Glu | |
| 150 | | | | | 155 | | | | | 160 | | | | | 165 | |
| cag | gac | tac | ata | gac | cta | gcg | gtt | ctc | ttc | aat | ctc | gct | tgg | att | gac | 624 |
| Gln | Asp | Tyr | Ile | Asp | Leu | Ala | Val | Leu | Phe | Asn | Leu | Ala | Trp | Ile | Asp | |
| | | | 170 | | | | | 175 | | | | | 180 | | | |
| tac | aat | tac | atc | acg | agc | acg | ccg | gag | ttc | aag | gcc | ctc | tac | gac | aag | 672 |
| Tyr | Asn | Tyr | Ile | Thr | Ser | Thr | Pro | Glu | Phe | Lys | Ala | Leu | Tyr | Asp | Lys | |
| | | 185 | | | | | 190 | | | | | 195 | | | | |
| gtt | gac | gag | ggc | ggc | tat | aca | agg | gcg | gac | gtc | aaa | acc | gtt | ctc | gac | 720 |
| Val | Asp | Glu | Gly | Gly | Tyr | Thr | Arg | Ala | Asp | Val | Lys | Thr | Val | Leu | Asp | |
| | 200 | | | | | 205 | | | | | 210 | | | | | |
| gcc | cag | atc | tgg | ctt | ctc | aac | cac | acc | ttc | gag | gag | cac | gag | aag | ata | 768 |
| Ala | Gln | Ile | Trp | Leu | Leu | Asn | His | Thr | Phe | Glu | Glu | His | Glu | Lys | Ile | |
| | 215 | | | | | 220 | | | | | 225 | | | | | |
| aac | ctc | ctc | ctc | gga | aac | ggc | aac | gtc | gag | gtc | acg | gtc | gtt | ccc | tac | 816 |

```
                Asn Leu Leu Gly Asn Gly Asn Val Glu Val Thr Val Val Pro Tyr
                230             235                 240                 245 gcc cac ccg ata ggc ccg ata ctc aac gac ttc ggc tgg gac agc gac            864
Ala His Pro Ile Gly Pro Ile Leu Asn Asp Phe Gly Trp Asp Ser Asp
                250                 255                 260 ttc aac gac cag gtc aag aag gcc gac gaa ctg tac aag ccg tac ctc            912
Phe Asn Asp Gln Val Lys Lys Ala Asp Glu Leu Tyr Lys Pro Tyr Leu
            265                 270                 275 ggc ggc ggc acc gcg gtt cca aaa ggc gga tgg gcg gct gag agc gcc            960
Gly Gly Gly Thr Ala Val Pro Lys Gly Gly Trp Ala Ala Glu Ser Ala
        280                 285                 290 ctc aac gac aaa act ctg gag atc ctc gcc gag aac ggc tgg gag tgg           1008
Leu Asn Asp Lys Thr Leu Glu Ile Leu Ala Glu Asn Gly Trp Glu Trp
    295                 300                 305 gtc atg acc gac cag atg gtt ctc gga aag ctc ggc att gag gga acc           1056
Val Met Thr Asp Gln Met Val Leu Gly Lys Leu Gly Ile Glu Gly Thr
310                 315                 320                 325 gtc gag aac tac cac aag ccc tgg gtg gcc gag ttc aac gga aag aag           1104
Val Glu Asn Tyr His Lys Pro Trp Val Ala Glu Phe Asn Gly Lys Lys
                330                 335                 340 ata tac ctc ttc cca aga aat cac gat cta agt gac aga gtt ggc ttt           1152
Ile Tyr Leu Phe Pro Arg Asn His Asp Leu Ser Asp Arg Val Gly Phe
            345                 350                 355 acc tac agc gga atg aac cag cag cag gcc gtt gag gac ttc gtc aac           1200
Thr Tyr Ser Gly Met Asn Gln Gln Gln Ala Val Glu Asp Phe Val Asn
        360                 365                 370 gag ctc ctc aag ctc cag aag cag aac tac gat ggc tcg ctg gtt tac           1248
Glu Leu Leu Lys Leu Gln Lys Gln Asn Tyr Asp Gly Ser Leu Val Tyr
    375                 380                 385 gtg gtc acg ctc gac ggc gag aac ccc gtg gag aac tac ccc tac gac           1296
Val Val Thr Leu Asp Gly Glu Asn Pro Val Glu Asn Tyr Pro Tyr Asp
390                 395                 400                 405 ggg gag ctc ttc ctc acc gaa ctc tac aag aag ctg acc gaa ctc cag           1344
Gly Glu Leu Phe Leu Thr Glu Leu Tyr Lys Lys Leu Thr Glu Leu Gln
                410                 415                 420 gag cag ggt ctc ata aga acc ctc acc ccg agc gag tac atc cag ctc           1392
Glu Gln Gly Leu Ile Arg Thr Leu Thr Pro Ser Glu Tyr Ile Gln Leu
            425                 430                 435 tac ggc gac aag gcc aac aag ctc aca cct cgg atg atg gag cgc ctt           1440
Tyr Gly Asp Lys Ala Asn Lys Leu Thr Pro Arg Met Met Glu Arg Leu
        440                 445                 450 gac ctc acc gga gac aac gtt aac gcc ctc ctc aag gcc cag agc ctc           1488
Asp Leu Thr Gly Asp Asn Val Asn Ala Leu Leu Lys Ala Gln Ser Leu
    455                 460                 465 ggc gaa ctc tac gac atg acc ggc gtt aag gag gag atg cag tgg ccc           1536
Gly Glu Leu Tyr Asp Met Thr Gly Val Lys Glu Glu Met Gln Trp Pro
470                 475                 480                 485 gag agc agc tgg ata gac gga acc ctc tcc acg tgg ata ggc gag ccc           1584
Glu Ser Ser Trp Ile Asp Gly Thr Leu Ser Thr Trp Ile Gly Glu Pro
                490                 495                 500 cag gag aac tac ggc tgg tac tgg ctc tac atg gcc agg aag gcc ctt           1632
Gln Glu Asn Tyr Gly Trp Tyr Trp Leu Tyr Met Ala Arg Lys Ala Leu
            505                 510                 515 atg gag aac aag gat aaa atg agc cag gcg gac tgg gag aag gcc tac           1680
Met Glu Asn Lys Asp Lys Met Ser Gln Ala Asp Trp Glu Lys Ala Tyr
        520                 525                 530 gag tac ctg ctc cgc gcc gag gca agc gac tgg ttc tgg tgg tac gga           1728
Glu Tyr Leu Leu Arg Ala Glu Ala Ser Asp Trp Phe Trp Trp Tyr Gly
    535                 540                 545
```

| | | | | | | | | | | | | | | | | |
|---|---|---|---|---|---|---|---|---|---|---|---|---|---|---|---|---|
| agc | gac | cag | gac | agc | ggc | cag | gac | tac | acc | ttc | gac | cgc | tac | ctg | aag | 1776 |
| Ser | Asp | Gln | Asp | Ser | Gly | Gln | Asp | Tyr | Thr | Phe | Asp | Arg | Tyr | Leu | Lys | |
| 550 | | | | 555 | | | | | 560 | | | | | 565 | | |
| acc | tac | ctc | tac | gag | atg | tac | aag | ctg | gca | gga | gtc | gag | ccg | ccg | agc | 1824 |
| Thr | Tyr | Leu | Tyr | Glu | Met | Tyr | Lys | Leu | Ala | Gly | Val | Glu | Pro | Pro | Ser | |
| | | | | 570 | | | | | 575 | | | | | 580 | | |
| tac | ctc | ttc | ggc | aac | tac | ttc | ccg | gac | gga | gag | ccc | tac | acc | acg | agg | 1872 |
| Tyr | Leu | Phe | Gly | Asn | Tyr | Phe | Pro | Asp | Gly | Glu | Pro | Tyr | Thr | Thr | Arg | |
| | | | 585 | | | | | 590 | | | | | 595 | | | |
| ggc | ctg | gtc | gga | ctc | aag | gac | ggc | gag | atg | aag | aac | ttc | tcc | agc | atg | 1920 |
| Gly | Leu | Val | Gly | Leu | Lys | Asp | Gly | Glu | Met | Lys | Asn | Phe | Ser | Ser | Met | |
| | | 600 | | | | | 605 | | | | | 610 | | | | |
| tcc | ccg | ctg | gca | aag | ggc | gtg | agc | gtc | tat | ttc | gac | ggc | gag | ggg | ata | 1968 |
| Ser | Pro | Leu | Ala | Lys | Gly | Val | Ser | Val | Tyr | Phe | Asp | Gly | Glu | Gly | Ile | |
| | 615 | | | | | 620 | | | | | 625 | | | | | |
| cac | ttc | ata | gtg | aaa | ggg | aac | ctg | gac | agg | ttc | gag | gtg | agc | atc | tgg | 2016 |
| His | Phe | Ile | Val | Lys | Gly | Asn | Leu | Asp | Arg | Phe | Glu | Val | Ser | Ile | Trp | |
| 630 | | | | 635 | | | | | 640 | | | | | 645 | | |
| gag | aag | gat | gag | cgc | gtt | ggc | aac | acg | ttc | acc | cgc | ctc | caa | gag | aag | 2064 |
| Glu | Lys | Asp | Glu | Arg | Val | Gly | Asn | Thr | Phe | Thr | Arg | Leu | Gln | Glu | Lys | |
| | | | | 650 | | | | | 655 | | | | | 660 | | |
| ccg | gac | gag | ttg | agc | tat | ttc | atg | ttc | cca | ttc | tca | agg | gac | agc | gtt | 2112 |
| Pro | Asp | Glu | Leu | Ser | Tyr | Phe | Met | Phe | Pro | Phe | Ser | Arg | Asp | Ser | Val | |
| | | | 665 | | | | | 670 | | | | | 675 | | | |
| ggt | ctc | ctc | ata | acc | aag | cac | gtc | gtg | tac | gag | aac | gga | aag | gcc | gag | 2160 |
| Gly | Leu | Leu | Ile | Thr | Lys | His | Val | Val | Tyr | Glu | Asn | Gly | Lys | Ala | Glu | |
| | | 680 | | | | | 685 | | | | | 690 | | | | |
| ata | tac | ggc | gcc | acc | gac | tac | gag | aag | agc | gag | aag | ctt | ggg | gaa | gcc | 2208 |
| Ile | Tyr | Gly | Ala | Thr | Asp | Tyr | Glu | Lys | Ser | Glu | Lys | Leu | Gly | Glu | Ala | |
| | 695 | | | | | 700 | | | | | 705 | | | | | |
| acc | gtc | aag | aac | acg | agc | gaa | gga | atc | gaa | gtc | gtc | ctt | ccc | ttt | gac | 2256 |
| Thr | Val | Lys | Asn | Thr | Ser | Glu | Gly | Ile | Glu | Val | Val | Leu | Pro | Phe | Asp | |
| 710 | | | | 715 | | | | | 720 | | | | | 725 | | |
| tac | ata | gaa | aac | ccc | tcc | gac | ttc | tac | ttc | gct | gtc | tcg | acg | gtc | aaa | 2304 |
| Tyr | Ile | Glu | Asn | Pro | Ser | Asp | Phe | Tyr | Phe | Ala | Val | Ser | Thr | Val | Lys | |
| | | | | 730 | | | | | 735 | | | | | 740 | | |
| gat | gga | gac | ctt | gag | gtg | ata | agc | act | cct | gtg | gag | ctc | aag | ctc | ccg | 2352 |
| Asp | Gly | Asp | Leu | Glu | Val | Ile | Ser | Thr | Pro | Val | Glu | Leu | Lys | Leu | Pro | |
| | | | 745 | | | | | 750 | | | | | 755 | | | |
| acc | gag | gtc | aag | gga | gtc | gtc | ata | gcc | gat | ata | acc | gac | cca | gaa | ggc | 2400 |
| Thr | Glu | Val | Lys | Gly | Val | Val | Ile | Ala | Asp | Ile | Thr | Asp | Pro | Glu | Gly | |
| | | 760 | | | | | 765 | | | | | 770 | | | | |
| gac | gac | cat | ggg | ccc | gga | aac | tac | act | tat | ccc | acg | gac | aag | gtc | ttc | 2448 |
| Asp | Asp | His | Gly | Pro | Gly | Asn | Tyr | Thr | Tyr | Pro | Thr | Asp | Lys | Val | Phe | |
| 775 | | | | 780 | | | | | 785 | | | | | | | |
| aag | cca | ggt | gtt | ttc | gac | ctc | ctc | cgc | ttc | agg | atg | ctc | gaa | cag | acg | 2496 |
| Lys | Pro | Gly | Val | Phe | Asp | Leu | Leu | Arg | Phe | Arg | Met | Leu | Glu | Gln | Thr | |
| 790 | | | | 795 | | | | | 800 | | | | | 805 | | |
| gag | agc | tac | gtc | atg | gag | ttc | tac | ttc | aag | gac | cta | ggt | ggt | aac | ccg | 2544 |
| Glu | Ser | Tyr | Val | Met | Glu | Phe | Tyr | Phe | Lys | Asp | Leu | Gly | Gly | Asn | Pro | |
| | | | 810 | | | | | 815 | | | | | 820 | | | |
| tgg | aac | gga | ccc | aac | ggc | ttc | agc | ctc | cag | ata | atc | gag | gtc | tac | ctc | 2592 |
| Trp | Asn | Gly | Pro | Asn | Gly | Phe | Ser | Leu | Gln | Ile | Ile | Glu | Val | Tyr | Leu | |
| | | 825 | | | | | 830 | | | | | 835 | | | | |
| gac | ttc | aag | gac | ggt | gga | aac | agt | tcg | gcc | att | aag | atg | ttc | ccc | gac | 2640 |
| Asp | Phe | Lys | Asp | Gly | Gly | Asn | Ser | Ser | Ala | Ile | Lys | Met | Phe | Pro | Asp | |
| | 840 | | | | | 845 | | | | | 850 | | | | | |
| gga | ccg | gga | gcc | aac | gtc | aac | ctc | gac | ccc | gag | cat | cca | tgg | gac | gtt | 2688 |
| Gly | Pro | Gly | Ala | Asn | Val | Asn | Leu | Asp | Pro | Glu | His | Pro | Trp | Asp | Val | |
| 855 | | | | 860 | | | | | 865 | | | | | | | |

-continued

| | |
|---|---|
| gcc ttc agg ata gcg ggc tgg gac tac gga aac ctc atc atc ctg ccg<br>Ala Phe Arg Ile Ala Gly Trp Asp Tyr Gly Asn Leu Ile Ile Leu Pro<br>870                  875                  880                885 | 2736 |
| aac gga acg gcc atc cag ggc gag atg cag att tcc gca gat ccg gtt<br>Asn Gly Thr Ala Ile Gln Gly Glu Met Gln Ile Ser Ala Asp Pro Val<br>                  890                  895                  900 | 2784 |
| aag aac gcc ata ata gtc aag gtt cca aag aag tac atc gcc ata aac<br>Lys Asn Ala Ile Ile Val Lys Val Pro Lys Lys Tyr Ile Ala Ile Asn<br>905                  910                  915 | 2832 |
| gag gac tac ggc ctc tgg gga gac gtc ctc gtc ggc tcg cag gac ggc<br>Glu Asp Tyr Gly Leu Trp Gly Asp Val Leu Val Gly Ser Gln Asp Gly<br>                  920                  925                  930 | 2880 |
| tac ggc ccg gac aag tgg aga acg gcg gca gtg gat gcg gag cag tgg<br>Tyr Gly Pro Asp Lys Trp Arg Thr Ala Ala Val Asp Ala Glu Gln Trp<br>935                  940                  945 | 2928 |
| aag ctt gga ggt gcg gac ccg cag gca gtc ata aac ggc gtg gcc ccg<br>Lys Leu Gly Gly Ala Asp Pro Gln Ala Val Ile Asn Gly Val Ala Pro<br>950                  955                  960                965 | 2976 |
| cgc gtc att gat gag ctg gtt ccg cag ggc ttt gaa ccg acc cag gag<br>Arg Val Ile Asp Glu Leu Val Pro Gln Gly Phe Glu Pro Thr Gln Glu<br>                  970                  975                  980 | 3024 |
| gag cag ctg agc agc tac gat gca aac gac atg aag ctc gcc act gtc<br>Glu Gln Leu Ser Ser Tyr Asp Ala Asn Asp Met Lys Leu Ala Thr Val<br>985                  990                  995 | 3072 |
| aag gcg ctg cta ctc ctc aag cag ggc atc gtt gtg acc gac ccg<br>Lys Ala Leu Leu Leu Leu Lys Gln Gly Ile Val Val Thr Asp Pro<br>1000                  1005                1010 | 3117 |
| gag gga gac gac cac ggg ccg gga acg tac acc tat ccg acg gac<br>Glu Gly Asp Asp His Gly Pro Gly Thr Tyr Thr Tyr Pro Thr Asp<br>1015                  1020                1025 | 3162 |
| aaa gtt ttc aag ccc ggt gtt ttc gac ctc ctc aag ttc aag gtg<br>Lys Val Phe Lys Pro Gly Val Phe Asp Leu Leu Lys Phe Lys Val<br>1030                  1035                1040 | 3207 |
| acc gag gga agc gac gac tgg acg ctg gag ttc cac ttc aaa gac<br>Thr Glu Gly Ser Asp Asp Trp Thr Leu Glu Phe His Phe Lys Asp<br>1045                  1050                1055 | 3252 |
| ctc ggt gga aac ccg tgg aac ggg ccg aac ggc ttc agc ctg cag<br>Leu Gly Gly Asn Pro Trp Asn Gly Pro Asn Gly Phe Ser Leu Gln<br>1060                  1065                1070 | 3297 |
| ata atc gag gta tac ttc gac ttc aag gag ggc ggg aac gtc tcg<br>Ile Ile Glu Val Tyr Phe Asp Phe Lys Glu Gly Gly Asn Val Ser<br>1075                  1080                1085 | 3342 |
| gcc att aag atg ttc ccg gat ggg ccc gga agc aac gtc cgt ctt<br>Ala Ile Lys Met Phe Pro Asp Gly Pro Gly Ser Asn Val Arg Leu<br>1090                  1095                1100 | 3387 |
| gat cca aat cac cca tgg gac ctg gcg ctt agg ata gcc ggc tgg<br>Asp Pro Asn His Pro Trp Asp Leu Ala Leu Arg Ile Ala Gly Trp<br>1105                  1110                1115 | 3432 |
| gac tac gga aac ctg ata att ctg ccc gac gga acc gcc tac caa<br>Asp Tyr Gly Asn Leu Ile Ile Leu Pro Asp Gly Thr Ala Tyr Gln<br>1120                  1125                1130 | 3477 |
| ggc gag atg cag att tcc gca gat ccg gtt aag aac gcc ata ata<br>Gly Glu Met Gln Ile Ser Ala Asp Pro Val Lys Asn Ala Ile Ile<br>1135                  1140                1145 | 3522 |
| gtc aag gtt cca aag aag tac ctg aac ata tcc gac tac gga ctc<br>Val Lys Val Pro Lys Lys Tyr Leu Asn Ile Ser Asp Tyr Gly Leu<br>1150                  1155                1160 | 3567 |
| tac acc gcc gtc atc gtg ggt tcc caa gac ggg tac ggc ccg gac<br>Tyr Thr Ala Val Ile Val Gly Ser Gln Asp Gly Tyr Gly Pro Asp | 3612 |

-continued

```
                1165                    1170                    1175
aag tgg agg ccc gtg gcc gct gag gcc gag cag tgg aag ctc gga        3657
Lys Trp Arg Pro Val Ala Ala Glu Ala Glu Gln Trp Lys Leu Gly
        1180                    1185                    1190 ggc gca gac ccc cag gcg gtc ata gac aac ctc gta cca agg gtc        3702
Gly Ala Asp Pro Gln Ala Val Ile Asp Asn Leu Val Pro Arg Val
        1195                    1200                    1205 gtt gat gaa ctc gtg ccg gag ggc ttc aag cca acg cag gag gag        3747
Val Asp Glu Leu Val Pro Glu Gly Phe Lys Pro Thr Gln Glu Glu
        1210                    1215                    1220 cag ctg agc agc tac gac ctt gag aag aag acc ctg gcg acg gtg        3792
Gln Leu Ser Ser Tyr Asp Leu Glu Lys Lys Thr Leu Ala Thr Val
        1225                    1230                    1235 ctc atg gta ccg ctc gtc aat ggg act ggc ggc gag gaa cca acg        3837
Leu Met Val Pro Leu Val Asn Gly Thr Gly Gly Glu Glu Pro Thr
        1240                    1245                    1250 ccg acg gag agc cca acg gaa acg acg aca acc aca ccc agc gaa        3882
Pro Thr Glu Ser Pro Thr Glu Thr Thr Thr Thr Thr Pro Ser Glu
        1255                    1260                    1265 aca acc acc aca act tca acg acc acc ggc cca agc tca acg acc        3927
Thr Thr Thr Thr Thr Ser Thr Thr Thr Gly Pro Ser Ser Thr Thr
        1270                    1275                    1280 acc agc aca ccc ggc gga gga atc tgc ggc cca ggc att ata gcg        3972
Thr Ser Thr Pro Gly Gly Gly Ile Cys Gly Pro Gly Ile Ile Ala
        1285                    1290                    1295 ggc ctg gcc ctg ata ccg ctc ctc ctc aag agg agg aac tga            4014
Gly Leu Ala Leu Ile Pro Leu Leu Leu Lys Arg Arg Asn
        1300                    1305                    1310

<210> SEQ ID NO 11
<211> LENGTH: 1337
<212> TYPE: PRT
<213> ORGANISM: Thermococcus hydrothermalis

<400> SEQUENCE: 11

Met Arg Arg Val Val Ala Leu Phe Ile Ala Ile Leu Met Leu Gly Ser
    -25                 -20                 -15

Ile Val Gly Ala Asn Val Lys Ser Val Gly Ala Ala Glu Pro Lys Pro
-10                 -5                  -1  1                   5

Leu Asn Val Ile Ile Val Trp His Gln His Gln Pro Tyr Tyr Tyr Asp
                10                  15                  20

Pro Val Gln Asp Val Tyr Thr Arg Pro Trp Val Arg Leu His Ala Ala
            25                  30                  35

Asn Asn Tyr Trp Lys Met Ala His Tyr Leu Ser Gln Tyr Pro Glu Val
        40                  45                  50

His Ala Thr Ile Asp Leu Ser Gly Ser Leu Ile Ala Gln Leu Ala Asp
    55                  60                  65

Tyr Met Asn Gly Lys Lys Asp Thr Tyr Gln Ile Ile Thr Glu Lys Ile
70                  75                  80                  85

Ala Asn Gly Glu Pro Leu Thr Val Asp Glu Lys Trp Phe Met Leu Gln
                90                  95                  100

Ala Pro Gly Gly Phe Phe Asp Asn Thr Ile Pro Trp Asn Gly Glu Pro
            105                 110                 115

Ile Thr Asp Pro Asn Gly Asn Pro Ile Arg Asp Phe Trp Asp Arg Tyr
        120                 125                 130

Thr Glu Leu Lys Asn Lys Met Leu Ser Ala Lys Ala Lys Tyr Ala Asn
    135                 140                 145
```

```
Phe Val Thr Glu Ser Gln Lys Val Ala Val Thr Asn Glu Phe Thr Glu
150                 155                 160                 165

Gln Asp Tyr Ile Asp Leu Ala Val Leu Phe Asn Leu Ala Trp Ile Asp
            170                 175                 180

Tyr Asn Tyr Ile Thr Ser Thr Pro Glu Phe Lys Ala Leu Tyr Asp Lys
                185                 190                 195

Val Asp Glu Gly Gly Tyr Thr Arg Ala Asp Val Lys Thr Val Leu Asp
        200                 205                 210

Ala Gln Ile Trp Leu Leu Asn His Thr Phe Glu His Glu Lys Ile
    215                 220                 225

Asn Leu Leu Leu Gly Asn Gly Asn Val Glu Val Thr Val Pro Tyr
230                 235                 240                 245

Ala His Pro Ile Gly Pro Ile Leu Asn Asp Phe Gly Trp Asp Ser Asp
                250                 255                 260

Phe Asn Asp Gln Val Lys Lys Ala Asp Glu Leu Tyr Lys Pro Tyr Leu
            265                 270                 275

Gly Gly Gly Thr Ala Val Pro Lys Gly Gly Trp Ala Ala Glu Ser Ala
        280                 285                 290

Leu Asn Asp Lys Thr Leu Glu Ile Leu Ala Glu Asn Gly Trp Glu Trp
295                 300                 305

Val Met Thr Asp Gln Met Val Leu Gly Lys Leu Gly Ile Glu Gly Thr
310                 315                 320                 325

Val Glu Asn Tyr His Lys Pro Trp Val Ala Glu Phe Asn Gly Lys Lys
                330                 335                 340

Ile Tyr Leu Phe Pro Arg Asn His Asp Leu Ser Asp Arg Val Gly Phe
            345                 350                 355

Thr Tyr Ser Gly Met Asn Gln Gln Gln Ala Val Glu Asp Phe Val Asn
        360                 365                 370

Glu Leu Leu Lys Leu Gln Lys Gln Asn Tyr Asp Gly Ser Leu Val Tyr
    375                 380                 385

Val Val Thr Leu Asp Gly Glu Asn Pro Val Glu Asn Tyr Pro Tyr Asp
390                 395                 400                 405

Gly Glu Leu Phe Leu Thr Glu Leu Tyr Lys Lys Leu Thr Glu Leu Gln
                410                 415                 420

Glu Gln Gly Leu Ile Arg Thr Leu Thr Pro Ser Glu Tyr Ile Gln Leu
            425                 430                 435

Tyr Gly Asp Lys Ala Asn Lys Leu Thr Pro Arg Met Met Glu Arg Leu
        440                 445                 450

Asp Leu Thr Gly Asp Asn Val Asn Ala Leu Leu Lys Ala Gln Ser Leu
    455                 460                 465

Gly Glu Leu Tyr Asp Met Thr Gly Val Lys Glu Glu Met Gln Trp Pro
470                 475                 480                 485

Glu Ser Ser Trp Ile Asp Gly Thr Leu Ser Thr Trp Ile Gly Glu Pro
                490                 495                 500

Gln Glu Asn Tyr Gly Trp Tyr Trp Leu Tyr Met Ala Arg Lys Ala Leu
            505                 510                 515

Met Glu Asn Lys Asp Lys Met Ser Gln Ala Asp Trp Glu Lys Ala Tyr
        520                 525                 530

Glu Tyr Leu Leu Arg Ala Glu Ala Ser Asp Trp Phe Trp Trp Tyr Gly
    535                 540                 545

Ser Asp Gln Asp Ser Gly Gln Asp Tyr Thr Phe Asp Arg Tyr Leu Lys
550                 555                 560                 565

Thr Tyr Leu Tyr Glu Met Tyr Lys Leu Ala Gly Val Glu Pro Pro Ser
```

-continued

```
                570                 575                 580
Tyr Leu Phe Gly Asn Tyr Phe Pro Asp Gly Glu Pro Tyr Thr Thr Arg
            585                 590                 595
Gly Leu Val Gly Leu Lys Asp Gly Glu Met Lys Asn Phe Ser Ser Met
            600                 605                 610
Ser Pro Leu Ala Lys Gly Val Ser Val Tyr Phe Asp Gly Glu Gly Ile
            615                 620                 625
His Phe Ile Val Lys Gly Asn Leu Asp Arg Phe Glu Val Ser Ile Trp
630                 635                 640                 645
Glu Lys Asp Glu Arg Val Gly Asn Thr Phe Thr Arg Leu Gln Glu Lys
            650                 655                 660
Pro Asp Glu Leu Ser Tyr Phe Met Phe Pro Phe Ser Arg Asp Ser Val
            665                 670                 675
Gly Leu Leu Ile Thr Lys His Val Val Tyr Glu Asn Gly Lys Ala Glu
            680                 685                 690
Ile Tyr Gly Ala Thr Asp Tyr Glu Lys Ser Glu Lys Leu Gly Glu Ala
695                 700                 705
Thr Val Lys Asn Thr Ser Glu Gly Ile Glu Val Val Leu Pro Phe Asp
710                 715                 720                 725
Tyr Ile Glu Asn Pro Ser Asp Phe Tyr Phe Ala Val Ser Thr Val Lys
            730                 735                 740
Asp Gly Asp Leu Glu Val Ile Ser Thr Pro Val Glu Leu Lys Leu Pro
            745                 750                 755
Thr Glu Val Lys Gly Val Val Ile Ala Asp Ile Thr Asp Pro Glu Gly
            760                 765                 770
Asp Asp His Gly Pro Gly Asn Tyr Thr Tyr Pro Thr Asp Lys Val Phe
775                 780                 785
Lys Pro Gly Val Phe Asp Leu Leu Arg Phe Arg Met Leu Glu Gln Thr
790                 795                 800                 805
Glu Ser Tyr Val Met Glu Phe Tyr Phe Lys Asp Leu Gly Gly Asn Pro
            810                 815                 820
Trp Asn Gly Pro Asn Gly Phe Ser Leu Gln Ile Ile Glu Val Tyr Leu
            825                 830                 835
Asp Phe Lys Asp Gly Gly Asn Ser Ser Ala Ile Lys Met Phe Pro Asp
            840                 845                 850
Gly Pro Gly Ala Asn Val Asn Leu Asp Pro Glu His Pro Trp Asp Val
            855                 860                 865
Ala Phe Arg Ile Ala Gly Trp Asp Tyr Gly Asn Leu Ile Ile Leu Pro
870                 875                 880                 885
Asn Gly Thr Ala Ile Gln Gly Glu Met Gln Ile Ser Ala Asp Pro Val
            890                 895                 900
Lys Asn Ala Ile Ile Val Lys Val Pro Lys Lys Tyr Ile Ala Ile Asn
            905                 910                 915
Glu Asp Tyr Gly Leu Trp Gly Asp Val Leu Val Gly Ser Gln Asp Gly
            920                 925                 930
Tyr Gly Pro Asp Lys Trp Arg Thr Ala Ala Val Asp Ala Glu Gln Trp
            935                 940                 945
Lys Leu Gly Gly Ala Asp Pro Gln Ala Val Ile Asn Gly Val Ala Pro
950                 955                 960                 965
Arg Val Ile Asp Glu Leu Val Pro Gln Gly Phe Glu Pro Thr Gln Glu
            970                 975                 980
Glu Gln Leu Ser Ser Tyr Asp Ala Asn Asp Met Lys Leu Ala Thr Val
            985                 990                 995
```

Lys Ala Leu Leu Leu Leu Lys Gln Gly Ile Val Val Thr Asp Pro
            1000                1005                1010

Glu Gly Asp Asp His Gly Pro Gly Thr Tyr Thr Tyr Pro Thr Asp
    1015                1020                1025

Lys Val Phe Lys Pro Gly Val Phe Asp Leu Leu Lys Phe Lys Val
1030                1035                1040

Thr Glu Gly Ser Asp Asp Trp Thr Leu Glu Phe His Phe Lys Asp
    1045                1050                1055

Leu Gly Gly Asn Pro Trp Asn Gly Pro Asn Gly Phe Ser Leu Gln
    1060                1065                1070

Ile Ile Glu Val Tyr Phe Asp Phe Lys Glu Gly Gly Asn Val Ser
    1075                1080                1085

Ala Ile Lys Met Phe Pro Asp Gly Pro Gly Ser Asn Val Arg Leu
    1090                1095                1100

Asp Pro Asn His Pro Trp Asp Leu Ala Leu Arg Ile Ala Gly Trp
    1105                1110                1115

Asp Tyr Gly Asn Leu Ile Ile Leu Pro Asp Gly Thr Ala Tyr Gln
    1120                1125                1130

Gly Glu Met Gln Ile Ser Ala Asp Pro Val Lys Asn Ala Ile Ile
    1135                1140                1145

Val Lys Val Pro Lys Lys Tyr Leu Asn Ile Ser Asp Tyr Gly Leu
    1150                1155                1160

Tyr Thr Ala Val Ile Val Gly Ser Gln Asp Gly Tyr Gly Pro Asp
    1165                1170                1175

Lys Trp Arg Pro Val Ala Ala Glu Ala Glu Gln Trp Lys Leu Gly
    1180                1185                1190

Gly Ala Asp Pro Gln Ala Val Ile Asp Asn Leu Val Pro Arg Val
    1195                1200                1205

Val Asp Glu Leu Val Pro Glu Gly Phe Lys Pro Thr Gln Glu Glu
    1210                1215                1220

Gln Leu Ser Ser Tyr Asp Leu Glu Lys Lys Thr Leu Ala Thr Val
    1225                1230                1235

Leu Met Val Pro Leu Val Asn Gly Thr Gly Gly Glu Pro Thr
    1240                1245                1250

Pro Thr Glu Ser Pro Thr Glu Thr Thr Thr Thr Pro Ser Glu
    1255                1260                1265

Thr Thr Thr Thr Thr Ser Thr Thr Thr Gly Pro Ser Ser Thr Thr
    1270                1275                1280

Thr Ser Thr Pro Gly Gly Gly Ile Cys Gly Pro Gly Ile Ile Ala
    1285                1290                1295

Gly Leu Ala Leu Ile Pro Leu Leu Leu Lys Arg Arg Asn
    1300                1305                1310

<210> SEQ ID NO 12
<211> LENGTH: 809
<212> TYPE: PRT
<213> ORGANISM: Artificial Sequence
<220> FEATURE:
<223> OTHER INFORMATION: Hybrid pullulanase of Thermoccus hydrothermalis
      and Thermococcus litoralis
<220> FEATURE:
<221> NAME/KEY: SIGNAL
<222> LOCATION: (1)..(27)
<220> FEATURE:
<221> NAME/KEY: mat_peptide
<222> LOCATION: (28)..(809)

<400> SEQUENCE: 12

```
Met Lys Lys Pro Leu Gly Lys Ile Val Ala Ser Thr Ala Leu Leu Ile
    -25                 -20                 -15
Ser Val Ala Phe Ser Ser Ile Ala Ser Glu Glu Pro Lys Pro
    -10                 -5              -1   1                   5
Leu Asn Val Ile Ile Val Trp His Gln His Gln Pro Tyr Tyr Tyr Asp
                    10                  15                  20
Pro Ile Gln Asp Ile Tyr Thr Arg Pro Trp Val Arg Leu His Ala Ala
                25                  30                  35
Asn Asn Tyr Trp Lys Met Ala Asn Tyr Leu Ser Lys Tyr Pro Asp Val
            40                  45                  50
His Val Ala Ile Asp Leu Ser Gly Ser Leu Ile Ala Gln Leu Ala Asp
    55                  60                  65
Tyr Met Asn Gly Lys Lys Asp Thr Tyr Gln Ile Val Thr Glu Lys Ile
70                  75                  80                  85
Ala Asn Gly Glu Pro Leu Thr Leu Glu Asp Lys Trp Phe Met Leu Gln
                90                  95                  100
Ala Pro Gly Gly Phe Phe Asp His Thr Ile Pro Trp Asn Gly Glu Pro
                105                 110                 115
Val Ala Asp Glu Asn Gly Asn Pro Tyr Arg Glu Gln Trp Asp Arg Tyr
                120                 125                 130
Ala Glu Leu Lys Asp Lys Arg Asn Asn Ala Phe Lys Lys Tyr Ala Asn
                135                 140                 145
Leu Pro Leu Asn Glu Gln Lys Val Lys Ile Thr Ala Glu Phe Thr Glu
150                 155                 160                 165
Gln Asp Tyr Ile Asp Leu Ala Val Leu Phe Asn Leu Ala Trp Ile Asp
                170                 175                 180
Tyr Asn Tyr Ile Ile Asn Thr Pro Glu Leu Lys Ala Leu Tyr Asp Lys
                185                 190                 195
Val Asp Val Gly Gly Tyr Thr Lys Glu Asp Val Ala Thr Val Leu Lys
                200                 205                 210
His Gln Met Trp Leu Leu Asn His Thr Phe Glu Glu His Glu Lys Ile
                215                 220                 225
Asn Tyr Leu Leu Gly Asn Gly Asn Val Glu Val Thr Val Pro Tyr
230                 235                 240                 245
Ala His Pro Ile Gly Pro Leu Leu Asn Asp Phe Gly Trp Tyr Glu Asp
                250                 255                 260
Phe Asp Ala His Val Lys Lys Ala His Glu Leu Tyr Lys Lys Tyr Leu
                265                 270                 275
Gly Asp Asn Arg Val Glu Pro Gln Gly Gly Trp Ala Ala Glu Ser Ala
                280                 285                 290
Leu Asn Asp Lys Thr Leu Glu Ile Leu Thr Asn Asn Gly Trp Lys Trp
                295                 300                 305
Val Met Thr Asp Gln Met Val Leu Asp Ile Leu Gly Ile Pro Asn Thr
310                 315                 320                 325
Val Glu Asn Tyr Tyr Lys Pro Trp Val Ala Glu Phe Asn Gly Lys Lys
                330                 335                 340
Ile Tyr Leu Phe Pro Arg Asn His Asp Leu Ser Asp Arg Val Gly Phe
                345                 350                 355
Arg Tyr Ser Gly Met Asn Gln Tyr Gln Ala Val Glu Asp Phe Val Asn
                360                 365                 370
Glu Leu Leu Lys Val Gln Lys Glu Asn Tyr Asp Gly Ser Leu Val Tyr
                375                 380                 385
```

Val Val Thr Leu Asp Gly Glu Asn Pro Trp Glu His Tyr Pro Phe Asp
390                 395                 400                 405

Gly Lys Ile Phe Leu Glu Glu Leu Tyr Lys Lys Leu Thr Glu Leu Gln
                410                 415                 420

Lys Gln Gly Leu Ile Arg Thr Val Thr Pro Ser Glu Tyr Ile Gln Met
            425                 430                 435

Tyr Gly Asp Lys Ala Asn Lys Leu Thr Pro Arg Met Met Glu Arg Leu
        440                 445                 450

Asp Leu Thr Gly Asp Asn Val Asn Ala Leu Leu Lys Ala Gln Ser Leu
    455                 460                 465

Gly Glu Leu Tyr Asp Met Thr Gly Val Lys Glu Met Gln Trp Pro
470                 475                 480                 485

Glu Ser Ser Trp Ile Asp Gly Thr Leu Ser Thr Trp Ile Gly Glu Pro
                490                 495                 500

Gln Glu Asn Tyr Gly Trp Tyr Trp Leu Tyr Met Ala Arg Lys Ala Leu
            505                 510                 515

Met Glu Asn Lys Asp Lys Met Ser Gln Ala Asp Trp Glu Lys Ala Tyr
        520                 525                 530

Glu Tyr Leu Leu Arg Ala Glu Ala Ser Asp Trp Phe Trp Trp Tyr Gly
    535                 540                 545

Ser Asp Gln Asp Ser Gly Gln Asp Tyr Thr Phe Asp Arg Tyr Leu Lys
550                 555                 560                 565

Thr Tyr Leu Tyr Glu Met Tyr Lys Leu Ala Gly Val Glu Pro Pro Ser
                570                 575                 580

Tyr Leu Phe Gly Asn Tyr Phe Pro Asp Gly Glu Pro Tyr Thr Thr Arg
            585                 590                 595

Gly Leu Val Gly Leu Lys Asp Gly Glu Met Lys Asn Phe Ser Ser Met
        600                 605                 610

Ser Pro Leu Ala Lys Gly Val Ser Val Tyr Phe Asp Gly Glu Gly Ile
    615                 620                 625

His Phe Ile Val Lys Gly Asn Leu Asp Arg Phe Glu Val Ser Ile Trp
630                 635                 640                 645

Glu Lys Asp Glu Arg Val Gly Asn Thr Phe Thr Arg Leu Gln Glu Lys
                650                 655                 660

Pro Asp Glu Leu Ser Tyr Phe Met Phe Pro Phe Ser Arg Asp Ser Val
            665                 670                 675

Gly Leu Leu Ile Thr Lys His Val Val Tyr Glu Asn Gly Lys Ala Glu
        680                 685                 690

Ile Tyr Gly Ala Thr Asp Tyr Glu Lys Ser Glu Lys Leu Gly Glu Ala
    695                 700                 705

Thr Val Lys Asn Thr Ser Glu Gly Ile Glu Val Val Leu Pro Phe Asp
710                 715                 720                 725

Tyr Ile Glu Asn Pro Ser Asp Phe Tyr Phe Ala Val Ser Thr Val Lys
                730                 735                 740

Asp Gly Asp Leu Glu Val Ile Ser Thr Pro Val Glu Leu Lys Leu Pro
            745                 750                 755

Thr Glu Val Lys Gly Val Val Ile Ala Asp Ile Thr Asp Pro Glu Gly
        760                 765                 770

Asp Asp His Gly Pro Gly Asn Tyr Thr
    775                 780

<210> SEQ ID NO 13
<211> LENGTH: 412

```
<212> TYPE: PRT
<213> ORGANISM: Pyrococcus furiosus
<220> FEATURE:
<221> NAME/KEY: mat_peptide
<222> LOCATION: (1)..(412)
<223> OTHER INFORMATION: Pyrococcus furiosus protease (Pfu)

<400> SEQUENCE: 13
```

| | | | | | | | | | | | | | | |
|---|---|---|---|---|---|---|---|---|---|---|---|---|---|---|
| Ala | Glu | Leu | Glu | Gly | Leu | Asp | Glu | Ser | Ala | Ala | Gln | Val | Met | Ala | Thr |
| 1 | | | | 5 | | | | | 10 | | | | | 15 | |
| Tyr | Val | Trp | Asn | Leu | Gly | Tyr | Asp | Ser | Gly | Ile | Thr | Ile | Gly | Ile | |
| | | | 20 | | | | | 25 | | | | | 30 | | |
| Ile | Asp | Thr | Gly | Ile | Asp | Ala | Ser | His | Pro | Asp | Leu | Gln | Gly | Lys | Val |
| | | | 35 | | | | | 40 | | | | | 45 | | |
| Ile | Gly | Trp | Val | Asp | Phe | Val | Asn | Gly | Arg | Ser | Tyr | Pro | Tyr | Asp | Asp |
| | 50 | | | | | 55 | | | | | 60 | | | | |
| His | Gly | His | Gly | Thr | His | Val | Ala | Ser | Ile | Ala | Ala | Gly | Thr | Gly | Ala |
| 65 | | | | | 70 | | | | | 75 | | | | | 80 |
| Ala | Ser | Asn | Gly | Lys | Tyr | Lys | Gly | Met | Ala | Pro | Gly | Ala | Lys | Leu | Ala |
| | | | | 85 | | | | | 90 | | | | | 95 | |
| Gly | Ile | Lys | Val | Leu | Gly | Ala | Asp | Gly | Ser | Gly | Ser | Ile | Ser | Thr | Ile |
| | | | 100 | | | | | 105 | | | | | 110 | | |
| Ile | Lys | Gly | Val | Glu | Trp | Ala | Val | Asp | Asn | Lys | Asp | Lys | Tyr | Gly | Ile |
| | | 115 | | | | | 120 | | | | | 125 | | | |
| Lys | Val | Ile | Asn | Leu | Ser | Leu | Gly | Ser | Ser | Gln | Ser | Ser | Asp | Gly | Thr |
| | 130 | | | | | 135 | | | | | 140 | | | | |
| Asp | Ala | Leu | Ser | Gln | Ala | Val | Asn | Ala | Ala | Trp | Asp | Ala | Gly | Leu | Val |
| 145 | | | | | 150 | | | | | 155 | | | | | 160 |
| Val | Val | Val | Ala | Ala | Gly | Asn | Ser | Gly | Pro | Asn | Lys | Tyr | Thr | Ile | Gly |
| | | | | 165 | | | | | 170 | | | | | 175 | |
| Ser | Pro | Ala | Ala | Ala | Ser | Lys | Val | Ile | Thr | Val | Gly | Ala | Val | Asp | Lys |
| | | | 180 | | | | | 185 | | | | | 190 | | |
| Tyr | Asp | Val | Ile | Thr | Ser | Phe | Ser | Ser | Arg | Gly | Pro | Thr | Ala | Asp | Gly |
| | | 195 | | | | | 200 | | | | | 205 | | | |
| Arg | Leu | Lys | Pro | Glu | Val | Val | Ala | Pro | Gly | Asn | Trp | Ile | Ile | Ala | Ala |
| 210 | | | | | 215 | | | | | 220 | | | | | |
| Arg | Ala | Ser | Gly | Thr | Ser | Met | Gly | Gln | Pro | Ile | Asn | Asp | Tyr | Tyr | Thr |
| 225 | | | | | 230 | | | | | 235 | | | | | 240 |
| Ala | Ala | Pro | Gly | Thr | Ser | Met | Ala | Thr | Pro | His | Val | Ala | Gly | Ile | Ala |
| | | | | 245 | | | | | 250 | | | | | 255 | |
| Ala | Leu | Leu | Leu | Gln | Ala | His | Pro | Ser | Trp | Thr | Pro | Asp | Lys | Val | Lys |
| | | | 260 | | | | | 265 | | | | | 270 | | |
| Thr | Ala | Leu | Ile | Glu | Thr | Ala | Asp | Ile | Val | Lys | Pro | Asp | Glu | Ile | Ala |
| | | 275 | | | | | 280 | | | | | 285 | | | |
| Asp | Ile | Ala | Tyr | Gly | Ala | Gly | Arg | Val | Asn | Ala | Tyr | Lys | Ala | Ile | Asn |
| | 290 | | | | | 295 | | | | | 300 | | | | |
| Tyr | Asp | Asn | Tyr | Ala | Lys | Leu | Val | Phe | Thr | Gly | Tyr | Val | Ala | Asn | Lys |
| 305 | | | | | 310 | | | | | 315 | | | | | 320 |
| Gly | Ser | Gln | Thr | His | Gln | Phe | Val | Ile | Ser | Gly | Ala | Ser | Phe | Val | Thr |
| | | | | 325 | | | | | 330 | | | | | 335 | |
| Ala | Thr | Leu | Tyr | Trp | Asp | Asn | Ala | Asn | Ser | Asp | Leu | Asp | Leu | Tyr | Leu |
| | | | 340 | | | | | 345 | | | | | 350 | | |
| Tyr | Asp | Pro | Asn | Gly | Asn | Gln | Val | Asp | Tyr | Ser | Tyr | Thr | Ala | Tyr | Tyr |
| | | 355 | | | | | 360 | | | | | 365 | | | |
| Gly | Phe | Glu | Lys | Val | Gly | Tyr | Tyr | Asn | Pro | Thr | Asp | Gly | Thr | Trp | Thr |

```
              370                 375                 380
Ile Lys Val Val Ser Tyr Ser Gly Ser Ala Asn Tyr Gln Val Asp Val
385                 390                 395                 400

Val Ser Asp Gly Ser Leu Ser Gln Pro Gly Ser Ser
                405                 410

<210> SEQ ID NO 14
<211> LENGTH: 595
<212> TYPE: PRT
<213> ORGANISM: Penicillium oxalicum
<220> FEATURE:
<221> NAME/KEY: mat_peptide
<222> LOCATION: (1)..(595)
<223> OTHER INFORMATION: mature Penicillium oxalicum glucoamylase
      sequence

<400> SEQUENCE: 14

Arg Pro Asp Pro Lys Gly Gly Asn Leu Thr Pro Phe Ile His Lys Glu
1               5                   10                  15

Gly Glu Arg Ser Leu Gln Gly Ile Leu Asp Asn Leu Gly Gly Arg Gly
            20                  25                  30

Lys Lys Thr Pro Gly Thr Ala Ala Gly Leu Phe Ile Ala Ser Pro Asn
        35                  40                  45

Thr Glu Asn Pro Asn Tyr Tyr Tyr Thr Trp Thr Arg Asp Ser Ala Leu
50                  55                  60

Thr Ala Lys Cys Leu Ile Asp Leu Phe Glu Asp Ser Arg Ala Lys Phe
65                  70                  75                  80

Pro Ile Asp Arg Lys Tyr Leu Glu Thr Gly Ile Arg Asp Tyr Lys Ser
                85                  90                  95

Ser Gln Ala Ile Leu Gln Ser Val Ser Asn Pro Ser Gly Thr Leu Lys
            100                 105                 110

Asp Gly Ser Gly Leu Gly Glu Pro Lys Phe Glu Ile Asp Leu Asn Pro
        115                 120                 125

Phe Ser Gly Ala Trp Gly Arg Pro Gln Arg Asp Gly Pro Ala Leu Arg
130                 135                 140

Ala Thr Ala Met Ile Thr Tyr Ala Asn Tyr Leu Ile Ser His Gly Gln
145                 150                 155                 160

Lys Ser Asp Val Ser Gln Val Met Trp Pro Ile Ile Ala Asn Asp Leu
                165                 170                 175

Ala Tyr Val Gly Gln Tyr Trp Asn Asn Thr Gly Phe Asp Leu Trp Glu
            180                 185                 190

Glu Val Asp Gly Ser Ser Phe Phe Thr Ile Ala Val Gln His Arg Ala
        195                 200                 205

Leu Val Glu Gly Ser Gln Leu Ala Lys Lys Leu Gly Lys Ser Cys Asp
210                 215                 220

Ala Cys Asp Ser Gln Pro Pro Gln Ile Leu Cys Phe Leu Gln Ser Phe
225                 230                 235                 240

Trp Asn Gly Lys Tyr Ile Thr Ser Asn Ile Asn Thr Gln Ala Ser Arg
                245                 250                 255

Ser Gly Ile Asp Leu Asp Ser Val Leu Gly Ser Ile His Thr Phe Asp
            260                 265                 270

Pro Glu Ala Ala Cys Asp Asp Ala Thr Phe Gln Pro Cys Ser Ala Arg
        275                 280                 285

Ala Leu Ala Asn His Lys Val Tyr Val Asp Ser Phe Arg Ser Ile Tyr
290                 295                 300

Lys Ile Asn Ala Gly Leu Ala Glu Gly Ser Ala Ala Asn Val Gly Arg
```

-continued

```
            305                 310                 315                 320
Tyr Pro Glu Asp Val Tyr Gln Gly Gly Asn Pro Trp Tyr Leu Ala Thr
                    325                 330                 335
Leu Gly Ala Ser Glu Leu Leu Tyr Asp Ala Leu Tyr Gln Trp Asp Arg
                340                 345                 350
Leu Gly Lys Leu Glu Val Ser Glu Thr Ser Leu Ser Phe Phe Lys Asp
            355                 360                 365
Phe Asp Ala Thr Val Lys Ile Gly Ser Tyr Ser Arg Asn Ser Lys Thr
        370                 375                 380
Tyr Lys Lys Leu Thr Gln Ser Ile Lys Ser Tyr Ala Asp Gly Phe Ile
385                 390                 395                 400
Gln Leu Val Gln Gln Tyr Thr Pro Ser Asn Gly Ser Leu Ala Glu Gln
                    405                 410                 415
Tyr Asp Arg Asn Thr Ala Ala Pro Leu Ser Ala Asn Asp Leu Thr Trp
                420                 425                 430
Ser Phe Ala Ser Phe Leu Thr Ala Thr Gln Arg Arg Asp Ala Val Val
            435                 440                 445
Pro Pro Ser Trp Gly Ala Lys Ser Ala Asn Lys Val Pro Thr Thr Cys
        450                 455                 460
Ser Ala Ser Pro Val Val Gly Thr Tyr Lys Ala Pro Thr Ala Thr Phe
465                 470                 475                 480
Ser Ser Lys Thr Lys Cys Val Pro Ala Lys Asp Ile Val Pro Ile Thr
                    485                 490                 495
Phe Tyr Leu Ile Glu Asn Thr Tyr Tyr Gly Glu Asn Val Phe Met Ser
                500                 505                 510
Gly Asn Ile Thr Ala Leu Gly Asn Trp Asp Ala Lys Lys Gly Phe Pro
            515                 520                 525
Leu Thr Ala Asn Leu Tyr Thr Gln Asp Gln Asn Leu Trp Phe Ala Ser
        530                 535                 540
Val Glu Phe Ile Pro Ala Gly Thr Pro Phe Glu Tyr Lys Tyr Tyr Lys
545                 550                 555                 560
Val Glu Pro Asn Gly Asp Ile Thr Trp Glu Lys Gly Pro Asn Arg Val
                    565                 570                 575
Phe Val Ala Pro Thr Gly Cys Pro Val Gln Pro His Ser Asn Asp Val
                580                 585                 590
Trp Gln Phe
        595
```

PROCESSES FOR PRODUCING FUEL ETHANOL

CROSS-REFERENCE TO RELATED APPLICATIONS

This application is a continuation of U.S. application Ser. No. 15/727,952 filed Oct. 9, 2017, which is a continuation of U.S. application Ser. No. 13/994,310 filed Oct. 1, 2013, now U.S. Pat. No. 9,816,112, which is a 35 U.S.C. 371 national application of PCT/US2011/066559 filed Dec. 21, 2011 which claims priority or the benefit under 35 U.S.C. 119 of U.S. provisional application Nos. 61/426,039 and 61/566,373 filed Dec. 22, 2010 and Dec. 2, 2011, respectively, the contents of which are fully incorporated herein by reference.

FIELD OF THE INVENTION

The present invention relates to processes for producing fermentation products from starch-containing material. The invention also relates to a composition suitable for use in a process of the invention.

REFERENCE TO A SEQUENCE LISTING

This application contains a Sequence Listing in computer readable form, which is incorporated herein by reference.

BACKGROUND OF THE INVENTION

Production of fermentation products, such as ethanol, from starch-containing material is well-known in the art. Industrially two different kinds of processes are used today. The most commonly used process, often referred to as a "conventional process", including liquefying gelatinized starch at high temperature using typically a bacterial alpha-amylase, followed by simultaneous saccharification and fermentation carried out in the presence of a glucoamylase and a fermentation organism. Another well known process, often referred to as a "raw starch hydrolysis"-process (RSH process) includes simultaneously saccharifying and fermenting granular starch below the initial gelatinization temperature typically in the presence of an acid fungal alpha-amylase and a glucoamylase.

Despite significant improvement of fermentation product production processes over the past decade a significant amount of residual starch material is not converted into the desired fermentation product, such as ethanol. At least some of the unconverted residual starch material, e.g., sugars and dextrins, is in the form of non-fermentable Maillard products.

Therefore, there is still a desire and need for providing processes for producing fermentation products, such as ethanol, from starch-containing material that can provide a higher fermentation product yield compared to a conventional process.

SUMMARY OF THE INVENTION

The present invention relates to processes of producing fermentation products, such as ethanol from starch-containing material using a fermenting organism. The invention also relates to a composition suitable for use in a process of the invention.

In the first aspect the invention relates to processes for producing fermentation products, such as ethanol, from starch-containing material comprising the steps of:
i) liquefying the starch-containing material at a pH in the range from 4.5-5.0 at a temperature in the range from 80-90° C. using:
an alpha-amylase having a T½ (min) at pH 4.5, 85° C., 0.12 mM $CaCl_2$) of at least 10;
optionally a protease having a thermostability value of more than 20% determined as Relative Activity at 80° C./70° C.;
ii) saccharifying using a carbohydrate-source generating enzyme;
iii) fermenting using a fermenting organism.

In an embodiment a carbohydrate-source generating enzyme, in particular a thermostable glucoamylase, and/or a pullulanase is(are) present and/or added during liquefaction in step i).

In a second aspect the invention relates to compositions comprising an alpha-amylase and a protease, wherein
i) the alpha-amylase has a T½ (min) at pH 4.5, 85° C., 0.12 mM $CaCl_2$) of at least 10; and
ii) the protease has a thermostability value of more than 20% determined as Relative Activity at 80° C./70° C.

In an embodiment the composition further comprises a carbohydrate-source generating enzyme, in particular a thermostable glucoamylase, and/or a pullulanase.

In an embodiment a second alpha-amylase is present and/or added during liquefaction step i).

In an embodiment the invention relates to a composition comprising:
i) an alpha-amylase having a T½ (min) at pH 4.5, 85° C., 0.12 mM $CaCl_2$) of at least 10 derived from *Bacillus stearothermophilus*;
ii) a protease having a thermostability value of more than 20% determined as Relative Activity at 80° C./70° C. derived derived from *Pyrococcus furiosus* and/or *Thermoascus aurantiacus*; and optionally
iii) a glucoamylase derived from *Penicillium oxalicum*.

In an embodiment the composition comprises a second alpha-amylase.

Alpha-Amylase A (0.7 micro g)+Alpha-Amylase 1407 (1.4 micro g)+Glucoamylase PE001 (10 micro g)+Protease 196 (1 micro g) (pH 4.8).

Figure 4:
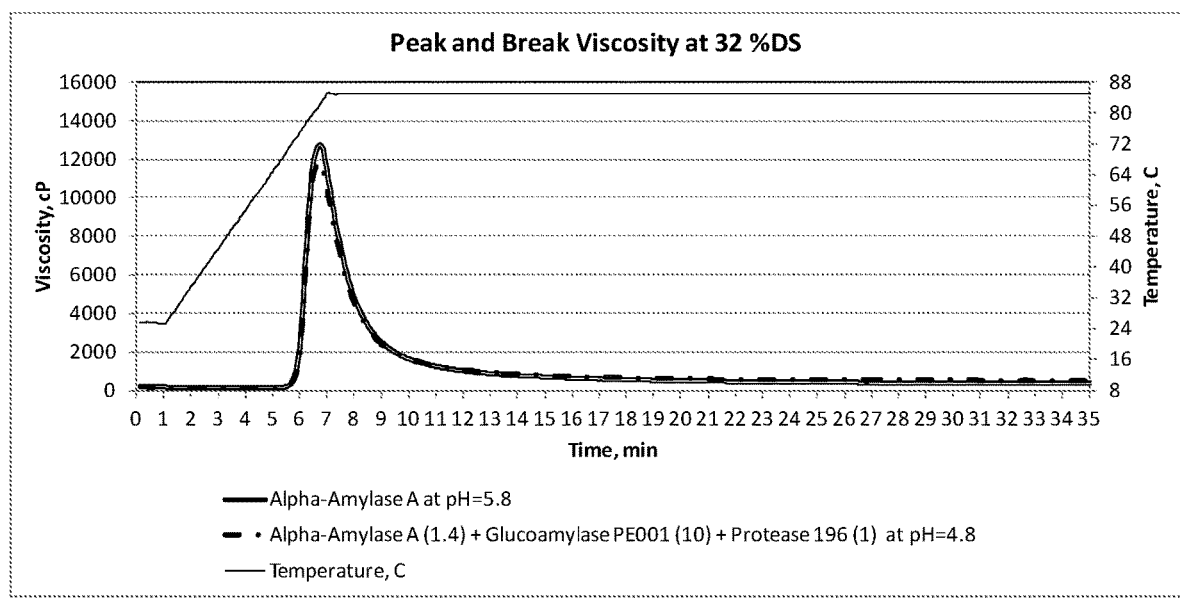

FIG. 4 shows the peak and break viscosity at 32% DS for the experiment in Example 10 comparing Alpha-Amylase A (1.4 micro g) (pH 5.8) and Alpha-Amylase A (1.4 micro g)+Glucoamylase PE001 (10 micro g)+Protease 196 (1 micro g) (pH 4.8).

Figure 5:
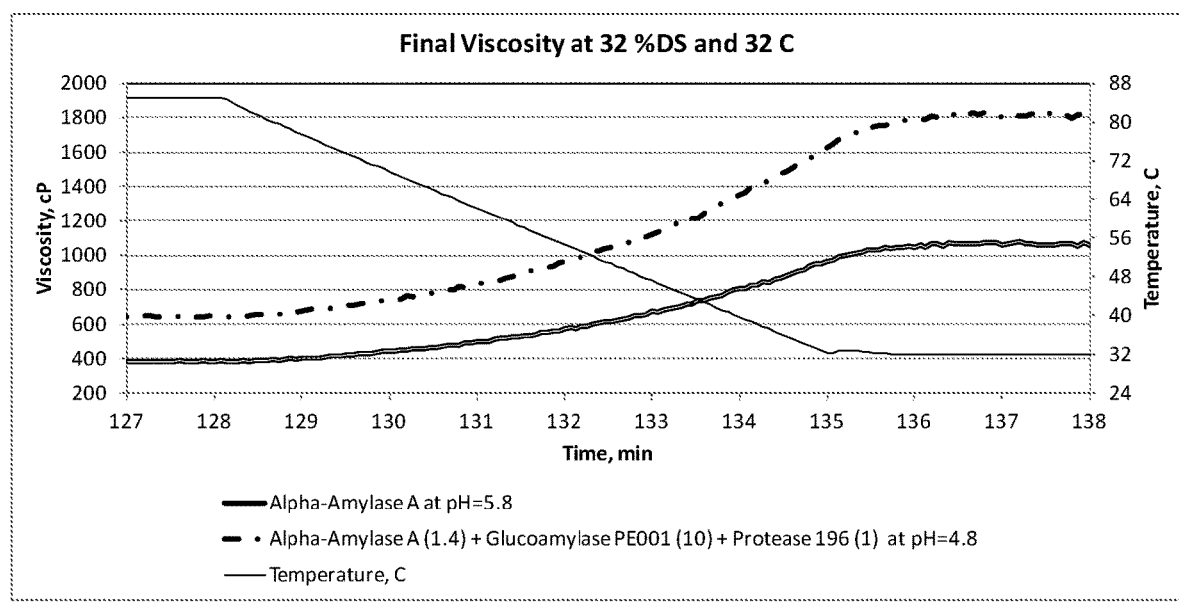

FIG. 5 shows the final viscosity at 32% DS, at 32° C. for the experiment in Example 10 comparing Alpha-Amylase A (1.4 micro g) (pH 5.8) and Alpha-Amylase A (1.4 micro g)+Glucoamylase PE001 (10 micro g)+Protease 196 (1 micro g) (pH 4.8).

DETAILED DESCRIPTION OF THE INVENTION

The present invention relates to processes of producing fermentation products, such as ethanol from starch-containing material using a fermenting organism. The invention also relates to a composition suitable for use in a process of the invention.

The inventors have shown that a process of the invention has a number of advantages. As shown in the Examples a process of the invention results in a higher ethanol yield. Other benefits, includes a reduced need for using $H_2SO_4$ for pH adjustment. This results in less sulfur downstream in the DDGS, less front-end fouling, less beerstone, and less phytate precipitation.

A process of the invention also results in reduced loss of sugars and dextrins to Maillard products. The DDGS color is improved and the heat exchanger lifetime (less solids) is extended. Furthermore, due to the higher thermostability of the enzymes used the enzyme dose may be reduced. A process of the invention requires limited changes to existing process and process equipment and thus limited capital investment.

By having a thermostable alpha-amylase and a second alpha-amylase as defined herein in liquefaction the peak viscosity, e.g., in slurry tank is (further) reduced. This result in less energy spent for mixing. Also having a lower average viscosity improves the mixing of the mash/starch in the slurry tank and its pumping through the liquefaction process.

In the first aspect the invention relates to processes for producing fermentation products from starch-containing material comprising the steps of:

i) liquefying the starch-containing material at a pH in the range from 4.5-5.0 at a temperature in the range from 80-90° C. using:
  an alpha-amylase having a T½ (min) at pH 4.5, 85° C., 0.12 mM $CaCl_2$ of at least 10;
  optionally a protease having a thermostability value of more than 20% determined as Relative Activity at 80° C./70° C.;
ii) saccharifying using a carbohydrate-source generating enzyme;
iii) fermenting using a fermenting organism.

In a preferred embodiment step ii) and iii) are carried out either sequentially or simultaneously. The thermostable alpha-amylase and optionally a thermostable protease and optionally the carbohydrate-source generating enzyme, preferably thermostable glucoamylase, and/or optionally a pullulanase may be added before and/or during liquefaction step i). Examples of thermostable alpha-amylases can be found in the "Alpha-Amylase Present and/or Added During Liquefaction" section below. Examples of thermostable proteases can be found in the "Protease Present and/or Added During Liquefaction"-section below. A composition of the invention may suitably be used in a process of the invention. However, the enzyme components may also be added separately.

In a preferred embodiment the pH during liquefaction is between 4.5-4.8.

In an embodiment a carbohydrate-source generating enzyme is also present during liquefaction. In a preferred embodiment the carbohydrate-source generating enzymes is a thermostable glucoamylase. In an embodiment the carbohydrate-source generating enzyme is different from the one used during saccharification in step ii) and/or fermentation in step iii).

Examples of "carbohydrate-source generating enzymes", including in particular glucoamylases, can be found in the "Carbohydrate-Source Generating Enzyme Present and/or Added During Liquefaction"-section below. Examples of thermostable glucoamylases can be found in the "Glucoamylase Present and/or Added During Liquefaction"-section below.

In an embodiment, the process of the invention further comprises, prior to the step i), the steps of:
a) reducing the particle size of the starch-containing material, preferably by dry milling;
b) forming a slurry comprising the starch-containing material and water.

The starch-containing starting material, such as whole grains, may be reduced in particle size, e.g., by milling, in order to open up the structure and allowing for further processing. Generally there are two types of processes: wet and dry milling. In dry milling whole kernels are milled and used. Wet milling gives a good separation of germ and meal (starch granules and protein) and is often applied at locations where the starch hydrolysate is used in production of, e.g., syrups. Both dry and wet milling is well known in the art of starch processing. According to the invention dry milling is preferred. In an embodiment the particle size is reduced to between 0.05 to 3.0 mm, preferably 0.1-0.5 mm, or so that at least 30%, preferably at least 50%, more preferably at least 70%, even more preferably at least 90% of the starch-containing material fit through a sieve with a 0.05 to 3.0 mm screen, preferably 0.1-0.5 mm screen. In another embodiment at least 50%, preferably at least 70%, more preferably at least 80%, especially at least 90% of the starch-containing material fit through a sieve with #6 screen.

The aqueous slurry may contain from 10-55 w/w-% dry solids (DS), preferably 25-45 w/w-% dry solids (DS), more preferably 30-40 w/w-% dry solids (DS) of starch-containing material. The slurry is heated to above the gelatinization temperature, preferably for between 80-90° C., pH 4.5-4.8 for around 15-60 minutes.

The thermostable alpha-amylase, optional thermostable protease and optional carbohydrate-source generating enzyme, in particular thermostable glucoamylase, and/or optional pullulanase may be added to the aqueous slurry to initiate liquefaction (thinning). In an embodiment only a part of the enzyme blend (composition of the invention) is added to the aqueous slurry, while the rest of the enzyme is added during liquefaction step i). Liquefaction step i) is typically carried out at 80-90° C., pH 4.5-4.8 for 1-3 hours.

The aqueous slurry may in an embodiment be jet-cooked to further gelatinize the slurry before being subjected to liquefaction in step i). The jet-cooking may be carried out at a temperature between 110-145° C., preferably 120-140° C., such as 125-135° C., preferably around 130° C. for about 1-15 minutes, preferably for about 3-10 minutes, especially around about 5 minutes.

Saccharification and Fermentation

One or more carbohydrate-source generating enzymes, in particular glucoamylases, are present and/or added during saccharification step ii) and/or fermentation step iii). The carbohydrate-source generating enzyme may preferably be a glucoamylase, but may also be an enzyme selected from the group consisting of: beta-amylase, maltogenic amylase and alpha-glucosidase.

Examples of carbohydrate-source generating enzyme, including glucoamylases, can be found in the "Carbohydrate-Source Generating Enzyme Present and/or Added During Saccharification and/or Fermentation"-section below.

When doing sequential saccharification and fermentation the saccharification step ii) may be carried out using conditions well-known in the art. For instance, the saccharification step ii) may last up to from about 24 to about 72 hours, however, it is common to do only a pre-saccharification of typically 40-90 minutes at a temperature between 30-65° C., typically about 60° C., followed by saccharification during fermentation in simultaneous saccharification and fermentation ("SSF). Saccharification is typically carried out at temperatures from 20-75° C., preferably from 40-70° C., typically around 60° C., and at a pH between 4 and 5, normally at about pH 4.5.

Simultaneous saccharification and fermentation ("SSF") is widely used in industrial scale fermentation product production processes, especially ethanol production processes. When doing SSF the saccharification step ii) and the fermentation step iii) are carried out simultaneously. There is no holding stage for the saccharification, meaning that a fermenting organism, such as yeast, and enzyme(s), may be added together. SSF are according to the invention typically carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours. In an embodiment the pH is between 3.5-5, in particular between 3.8 and 4.3.

Fermentation Medium

"Fermentation media" or "fermentation medium" which refers to the environment in which fermentation is carried out and which includes the fermentation substrate, that is, the carbohydrate source that is metabolized by the fermenting organism. The fermentation medium may comprise nutrients and growth stimulator(s) for the fermenting organism(s). Nutrient and growth stimulators are widely used in the art of fermentation and include nitrogen sources, such as ammonia; urea, vitamins and minerals, or combinations thereof.

Fermenting Organisms

The term "Fermenting organism" refers to any organism, including bacterial and fungal organisms, suitable for use in a fermentation process and capable of producing the desired fermentation product. Especially suitable fermenting organisms are able to ferment, i.e., convert, sugars, such as glucose or maltose, directly or indirectly into the desired fermentation product, such as ethanol. Examples of fermenting organisms include fungal organisms, such as yeast. Preferred yeast includes strains of Saccharomyces spp., in particular, Saccharomyces cerevisiae.

In one embodiment the fermenting organism is added to the fermentation medium so that the viable fermenting organism, such as yeast, count per mL of fermentation medium is in the range from $10^5$ to $10^{12}$, preferably from $10^7$ to $10^{10}$, especially about $5 \times 10^7$.

Commercially available yeast includes, e.g., RED STAR™ and ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

Starch-Containing Materials

Any suitable starch-containing material may be used according to the present invention. The starting material is generally selected based on the desired fermentation product. Examples of starch-containing materials, suitable for use in a process of the invention, include whole grains, corn, wheat, barley, rye, milo, sago, cassava, tapioca, sorghum, rice, peas, beans, or sweet potatoes, or mixtures thereof or starches derived there from, or cereals. Contemplated are also waxy and non-waxy types of corn and barley.

Fermentation Products

The term "fermentation product" means a product produced by a process including a fermentation step using a fermenting organism. Fermentation products contemplated according to the invention include alcohols (e.g., ethanol, methanol, butanol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, B12, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferred fermentation processes used include alcohol fermentation processes. The fermentation product, such as ethanol, obtained according to the invention, may preferably be used as fuel, that typically is blended with gasoline. However, in the case of ethanol it may also be used as potable ethanol.

Recovery

Subsequent to fermentation the fermentation product may be separated from the fermentation medium. The slurry may be distilled to extract the desired fermentation product. Alternatively the desired fermentation product may be extracted from the fermentation medium by micro or membrane filtration techniques. The fermentation product may also be recovered by stripping or other method well known in the art.

Alpha-Amylase Present and/or Added During Liquefaction

According to the invention a thermostable alpha-amylase is present and/or added during liquefaction optionally together with a thermostable protease, and optionally a carbohydrate-source generating enzyme, preferably a thermostable glucoamylase, and/or optionally a pullulanase. According to the invention the alpha-amylase has high activity toward starch solubilisation in liquefaction at pH 4.5 to 5.0 and high thermostability at pH 4.5-5.0 and 80-90° C., preferably 4.5-4.8, around 85° C.

More specifically the alpha-amylase used in a process of the invention has a T½ (min) at pH 4.5, 85° C., 0.12 mM $CaCl_2$) of at least 10 determined as described in Example 1.

In a preferred embodiment T½ (min) at pH 4.5, 85° C., 0.12 mM $CaCl_2$, is at least 15, such as at least 20, such as at least 25, such as at least 30, such as at least 40, such as at least 50, such as at least 60, such as between 10-70, such as between 15-70, such as between 20-70, such as between 25-70, such as between 30-70, such as between 40-70, such as between 50-70, such as between 60-70.

In an embodiment the thermostable alpha-amylase is a *Bacillus stearothermophilus* alpha-amylase variant having at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 3 disclosed in WO 99/019467 or SEQ ID NO: 1 herein.

In an embodiment of the invention the alpha-amylase is an bacterial alpha-amylase, preferably derived from the genus *Bacillus*, especially a strain of *Bacillus stearothermophilus*, in particular the *Bacillus stearothermophilus* as disclosed in WO 99/019467 as SEQ ID NO: 3 or SEQ ID NO: 1 herein with the double deletion I181+G182 and substitution N193F, further comprising the following mutations:

V59A+Q89R+G112D+E129V+K177L+R179E+K220P+ N224L+Q254S;
V59A+Q89R+E129V+K177L+R179E+H208Y+K220P+ N224L+Q254S;
V59A+Q89R+E129V+K177L+R179E+K220P+N224L+ Q254S+D269E+D281N;
V59A+Q89R+E129V+K177L+R179E+K220P+N224L+ Q254S+I270L;
V59A+Q89R+E129V+K177L+R179E+K220P+N224L+ Q254S+H274K;
V59A+Q89R+E129V+K177L+R179E+K220P+N224L+ Q254S+Y276F;
V59A+E129V+R157Y+K177L+R179E+K220P+ N224L+S242Q+Q254S;
V59A+E129V+K177L+R179E+H208Y+K220P+ N224L+S242Q+Q254S;
V59A+E129V+K177L+R179E+K220P+N224L+ S242Q+Q254S;
V59A+E129V+K177L+R179E+K220P+N224L+ S242Q+Q254S+H274K;
V59A+E129V+K177L+R179E+K220P+N224L+ S242Q+Q254S+Y276F;
V59A+E129V+K177L+R179E+K220P+N224L+ S242Q+Q254S+D281N;
V59A+E129V+K177L+R179E+K220P+N224L+ S242Q+Q254S+M284T;
V59A+E129V+K177L+R179E+K220P+N224L+ S242Q+Q254S+G416V;
V59A+E129V+K177L+R179E+K220P+N224L+Q254S;
V59A+E129V+K177L+R179E+K220P+N224L+ Q254S+M284T;
A91L+M96I+E129V+K177L+R179E+K220P+N224L+ S242Q+Q254S;
E129V+K177L+R179E;
E129V+K177L+R179E+K220P+N224L+S242Q+ Q254S;
E129V+K177L+R179E+K220P+N224L+S242Q+ Q254S+Y276F+L427M;
E129V+K177L+R179E+K220P+N224L+S242Q+ Q254S+M284T;
E129V+K177L+R179E+K220P+N224L+S242Q+ Q254S+N376*+I377*;
E129V+K177L+R179E+K220P+N224L+Q254S;
E129V+K177L+R179E+K220P+N224L+Q254S+ M284T;
E129V+K177L+R179E+S242Q;
E129V+K177L+R179V+K220P+N224L+S242Q+ Q254S;
K220P+N224L+S242Q+Q254S;
M284V.

The thermostable alpha-amylase may be a truncated *Bacillus stearothermophilus* alpha-amylase, preferably to have around 491 amino acids.

Second Alpha-Amylase Present and/or Added During Liquefaction

When a second alpha-amylase is present and/or added during liquefaction step i) a positive viscosity reducing effect is obtained. As can be seen from Example 10 the combination of a thermostable alpha-amylase (e.g., Alpha-Amylase BE1407) with or without the presence of a thermostable protease (e.g., Protease 196) and thermostable glucoamylase (e.g., Glucoamylase PO) and further a second alpha-amylase (e.g. Alpha-amylase A) results in decrease peak viscosity and final viscosity.

Therefore, in this aspect of the invention a second alpha-amylase is added during liquefaction step i). The second alpha-amylase may be less thermostable and/or less efficient at pH 4.5, 85° C., 0.12 mM $CaCl_2$, or around pH 4.8, than a thermostable alpha-amylase defined herein added and/or present during liquefaction according to the invention.

In an embodiment the second alpha-amylase is of bacterial origin.

In an embodiment the second alpha-amylase is derived from a strain of the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein. The second alpha-amylase may be a truncated *Bacillus stearothermophilus* alpha-amylase, preferably to have around 491 amino acids.

In an embodiment second alpha-amylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, or at least 100% identity to the mature part of the polypeptide of SEQ ID NO: 3 disclosed in WO 99/019467 or SEQ ID NO: 1 herein.

In an embodiment the second alpha-amylase has a T½ (min) at pH 4.5, 85° C., 0.12 mM $CaCl_2$) of below 10 determined as described in Example 1.

In an embodiment the second alpha-amylase has a T½ (min) at pH 4.5, 85° C., 0.12 mM $CaCl_2$) of below 8, such as below 7, such as below 6, such as below 5.

In an embodiment the second alpha-amylase has a T½ (min) at pH 4.5, 85° C., 0.12 mM $CaCl_2$) between 2 and 10, such as between 3 and 8, such as above 4 to 10, such as above 4 to 8.

In an embodiment the second alpha-amylase may be derived from *Bacillus stearothermophilus* and may have the following mutations: I181*+G182* or I181*+G182*+ N193F (using SEQ ID NO: 1 for numbering).

In an embodiment the invention relates to a process for producing fermentation products from starch-containing material comprising the steps of:

i) liquefying the starch-containing material at a pH in the range from 4.5-5.0 at a temperature in the range from 80-90° C. using:
   an alpha-amylase having a T½ (min) at pH 4.5, 85° C., 0.12 mM $CaCl_2$) of at least 10, and further a second alpha-amylase having a T½ (min) at pH 4.5, 85° C., 0.12 mM $CaCl_2$) of less than 10;

a protease having a thermostability value of more than 20% determined as Relative Activity at 80° C./70° C.;
ii) saccharifying using a glucoamylase;
iii) fermenting using a fermenting organism.

Protease Present and/or Added During Liquefaction

According to the invention a thermostable protease may be present and/or added during liquefaction together with a thermostable alpha-amylase, and optionally a carbohydrate-source generating enzyme, preferably a thermostable glucoamylase, and/or optionally a pullulanase.

A protease used in a process of the invention has either
i) a thermostability value of more than 20% determined as Relative Activity at 80° C./70° C.; and/or
ii) a thermostability value of more than 10% determined as Relative Activity at 85° C./70° C.

In an embodiment the protease has a thermostability value:
of more than 30%, more than 40%, more than 50%, more than 60%, more than 70%, more than 80%, more than 90% determined as Relative Activity at 80° C./70° C., and/or
of more than 12%, more than 14%, more than 16%, more than 18%, more than 20%, more than 25% determined as Relative Activity at 85° C./70° C.; and/or
of more that 20%, more than 30%, more than 40%, more than 50%, more than 60%, more than 70%, more than 80%, more than 90% determined as Remaining Activity at 80° C.; and/or
of more that 20%, more than 30%, more than 40%, more than 50%, more than 60%, more than 70%, more than 80%, more than 90% determined as Remaining Activity at 84° C. and/or.

Purified variants may have a thermostability for above 90, above 100 at 85° C. as determined using the Zein-BCA assay as disclosed in Example 3.

Determination of "Relative Activity" and "Remaining Activity" is determined as described in Example 2.

Proteases are classified on the basis of their catalytic mechanism into the following groups: Serine proteases (S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

In a preferred embodiment the thermostable protease used in a process of the invention is a "metallo protease" defined as a protease belonging to EC 3.4.24 (metalloendopeptidases); preferably EC 3.4.24.39 (acid metallo proteinases).

To determine whether a given protease is a metallo protease or not, reference is made to the above "Handbook of Proteolytic Enzymes" and the principles indicated therein. Such determination can be carried out for all types of proteases, be it naturally occurring or wild-type proteases; or genetically engineered or synthetic proteases.

Protease activity can be measured using any suitable assay, in which a substrate is employed, that includes peptide bonds relevant for the specificity of the protease in question. Assay-pH and assay-temperature are likewise to be adapted to the protease in question. Examples of assay-pH-values are pH 6, 7, 8, 9, 10, or 11. Examples of assay-temperatures are 30, 35, 37, 40, 45, 50, 55, 60, 65, 70 or 80° C.

Examples of protease substrates are casein, such as Azurine-Crosslinked Casein (AZCL-casein). Two protease assays are described below in the "Materials & Methods"-section, of which the so-called "AZCL-Casein Assay" is the preferred assay.

In an embodiment the protease has at least 20%, such as at least 30%, such as at least 40%, such as at least 50%, such as at least 60%, such as at least 70%, such as at least 80%, such as at least 90%, such as at least 100% of the activity of the JTP196 protease variant or Protease Pfu determined by the AZCL-casein assay.

There are no limitations on the origin of the protease used in a process of the invention as long as it fulfills the thermostability properties defined above. The protease may be a variant of, e.g., a wild-type protease as long as the protease has the thermostability properties defined above. In a preferred embodiment the protease is a variant of a metallo protease as defined above. In an embodiment the protease used in a process of the invention is of fungal origin, such as a fungal metallo protease, such as a fungal metallo protease derived from a strain of the genus *Thermoascus*, preferably a strain of *Thermoascus aurantiacus*, especially *Thermoascus aurantiacus* CGMCC No. 0670 (classified as EC 3.4.24.39).

In an embodiment the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 3 herein.

In an embodiment the protease is a variant of the mature part of the metallo protease shown in SEQ ID NO: 2 disclosed in WO 2003/048353 or the mature part of SEQ ID NO: 1 in WO 2010/008841 and shown as SEQ ID NO: 3 herein with the following mutations:
S5*+N26R+D79L+S87P+A112P+D142L;
S5*+D79L+S87P+A112P+D142L;
N26R+T46R+D79L+S87P+A112P+D142L;
A27K+D79L+Y82F+S87G+D104P+A112P+A126V+D142L;
A27K+D79L+Y82F+D104P+A112P+A126V+D142L;
A27K+D79L+S87P+A112P+T124V+D142L;
A27K+D79L+S87P+A112P+A126V+D142L;
A27K+D79L+S87P+A112P+D142L;
A27K+Y82F+S87G+D104P+A112P+A126V+D142L;
A27K+Y82F+D104P+A112P+A126V+D142L;
S36P+D79L+S87P+A112P+D142L;
A37P+D79L+S87P+A112P+D142L;
S38T+D79L+S87P+A112P+A126V+D142L;
T46R+D79L+S87P+T116V+D142L;
S49P+D79L+S87P+A112P+D142L;
S50P+D79L+S87P+A112P+D142L;
S70V+D79L+Y82F+S87G+Y97W+A112P+D142L;
S70V+D79L+Y82F+S87G+A112P+D142L;
D79L+P81R+S87P+A112P+D142L;
D79L+Y82F+S87G+Y97W+D104P+A112P+D142L;
D79L+Y82F+S87G+D104P+A112P+D142L;
D79L+Y82F+S87G+A112P+A126V+D142L;
D79L+Y82F+S87G+A112P+D142L;
D79L+Y82F+S87P+A112P+T124V+D142L;
D79L+Y82F+S87P+A112P+A126V+D142L;
D79L+Y82F+S87P+A112P+D142L;
D79L+S87P+N98C+A112P+G135C+D142L;
D79L+S87P+D104P+A112P+D142L;
D79L+S87P+A112P+T124V+A126V+D142L;
D79L+S87P+A112P+T124V+D142L;
D79L+S87P+A112P+D142L;
D79L+S87P+A112P+D142L+T141C+M161C;

Y82F+S87G+S70V+D79L+D104P+A112P+D142L;
Y82F+S87G+D79L+D104P+A112P+A126V+D142L.

In an embodiment the thermostable protease present and/or added during liquefaction step i) is derived from a strain of *Pyrococcus*, such as a strain of *Pyrococcus furiosus*. In an embodiment the protease is one shown as SEQ ID NO: 1 in U.S. Pat. No. 6,358,726-B1 (Takara Shuzo Company). In another embodiment the protease is one disclosed in SEQ ID NO: 13 herein or a protease having at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-B1 or SEQ ID NO: 13 herein. The *Pyroccus furiosus* protease can be purchased from Takara Shuzo Co. Ltd, Japan.

The *Pyrococcus furiosus* protease is a thermostable protease. The commercial product *Pyrococcus furiosus* protease (Pfu S) was found to have a thermostability of 110% (80° C./70° C.) and 103% (90° C./70° C.) at pH 4.5 determined as described in Example 2 herein.

Carbohydrate-Source Generating Enzyme Present and/or Added During Liquefaction

According to the invention a carbohydrate-source generating enzyme, preferably a thermostable glucoamylase, is present and/or added during liquefaction together with a thermostable alpha-amylase and optionally a thermostable protease. As mentioned above a pullulanase may also be present and/or added during liquefaction step i).

The term "carbohydrate-source generating enzyme" includes any enzymes generating fermentable sugars. A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrates may be converted directly or indirectly to the desired fermentation product, preferably ethanol. According to the invention a mixture of carbohydrate-source generating enzymes may be used. Specific examples include glucoamylase (being glucose generators), beta-amylase and maltogenic amylase (being maltose generators).

In a preferred embodiment the carbohydrate-source generating enzyme is a thermostable glucoamylase. The carbohydrate-source generating enzyme, in particular thermostable glucoamylase, may be added together with or separately from the thermostable alpha-amylase and optionally the thermostable protease.

In an embodiment the carbohydrate-source generating enzyme, preferably a thermostable glucoamylase, has a Relative Activity heat stability at 85° C. of at least 20%, at least 30%, preferably at least 35%. In an embodiment the carbohydrate-generating enzyme is a glucoamylase having a relative activity at pH 4.5 of at least 80%, preferably at least 85%, preferably at least 90%, preferably at least 95%.

In a specific and preferred embodiment the carbohydrate-source generating enzyme is a thermostable glucoamylase, preferably of fungal origin, preferably a filamentous fungi, such as from a strain of the genus *Penicillium*, especially a strain of *Penicillium oxalicum* disclosed as SEQ ID NO: 2 in PCT/CN10/071753 published as WO 2011/127802 (which is hereby incorporated by reference) and shown in SEQ ID NO: 9 or 14 herein.

In a preferred embodiment the carbohydrate-source generating enzyme is a variant of the *Penicillium oxalicum* glucoamylase disclosed as SEQ ID NO: 2 in PCT/CN10/071753 published as WO 2011/127802 and shown in SEQ ID NOS: 9 and 14 herein, having a K79V substitution (using the mature sequence shown in SEQ ID NO: 14 for numbering). The K79V glucoamylase variant has reduced sensitivity to protease degradation relative to the parent as disclosed in co-pending U.S. application No. 61/531,189 (which is hereby incorporated by reference).

In a specific embodiment the carbohydrate-source generating enzyme is a glucoamylase, preferably derived from a strain of the genus *Penicillium*, especially a strain of *Penicillium oxalicum* disclosed in PCT/CN10/071753 published as WO 2011/127802. The glucoamylase may also be glucoamylase having at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in PCT/CN10/071753 published as WO 2011/127802 and shown as SEQ ID NO: 9 and 14 herein.

Pullulanase Present and/or Added During Liquefaction

Optionally a pullulanase may be present and/or added during liquefaction step i) together with a thermostable alpha-amylase and optionally a thermostable protease. As mentioned above a carbohydrate-source generating enzyme, preferably a thermostable glucoamylase, may also be present and/or added during liquefaction step i).

The pullulanase may be present and/or added during liquefaction step i) and/or saccharification step ii) or simultaneous saccharification and fermentation.

Pullulanases (E.C. 3.2.1.41, pullulan 6-glucano-hydrolase), are debranching enzymes characterized by their ability to hydrolyze the alpha-1,6-glycosidic bonds in, for example, amylopectin and pullulan.

Contemplated pullulanases according to the present invention include the pullulanases from *Bacillus amyloderamificans* disclosed in U.S. Pat. No. 4,560,651 (hereby incorporated by reference), the pullulanase disclosed as SEQ ID NO: 2 in WO 01/151620 (hereby incorporated by reference), the *Bacillus deramificans* disclosed as SEQ ID NO: 4 in WO 01/151620 (hereby incorporated by reference), and the pullulanase from *Bacillus acidopullulyticus* disclosed as SEQ ID NO: 6 in WO 01/151620 (hereby incorporated by reference) and also described in FEMS Mic. Let. 115: 97-106 (1994).

Additional pullulanases contemplated according to the present invention included the pullulanases from *Pyrococcus woesei*, specifically from *Pyrococcus woesei* DSM No. 3773 disclosed in WO 92/02614, and the mature protein sequence disclosed as SEQ ID No: 6 herein.

In an embodiment the pullulanase is a family GH57 pullulanase. In an embodiment the pullulanase includes an X47 domain as disclosed in U.S. 61/289,040 published as WO 2011/087836 (which are hereby incorporated by reference). More specifically the pullulanase may be derived from a strain of the genus *Thermococcus*, including *Thermococcus litoralis* and *Thermococcus hydrothermalis*, such as the *Thermococcus hydrothermalis* pullulanase shown in SEQ ID NO: 11 truncated at site X4 right after the X47 domain (i.e., amino acids 1-782 in SEQ ID NOS: 11 and 12 herein). The pullulanase may also be a hybrid of the *Thermococcus litoralis* and *Thermococcus hydrothermalis* pullulanases or a *T. hydrothermalis/T. litoralis* hybrid enzyme with truncation site X4 disclosed in U.S. 61/289,040 published as WO 2011/087836 (which is hereby incorporated by reference) and disclosed in SEQ ID NO: 12.

The pullulanase may according to the invention be added in an effective amount which include the preferred amount of about 0.0001-10 mg enzyme protein per gram DS, preferably 0.0001-0.10 mg enzyme protein per gram DS, more preferably 0.0001-0.010 mg enzyme protein per gram DS. Pullulanase activity may be determined as NPUN. An Assay for determination of NPUN is described in the "Materials & Methods"-section below.

Suitable commercially available pullulanase products include PROMOZYME D, PROMOZYME™ D2 (Novozymes A/S, Denmark), OPTIMAX L-300 (Genencor Int., USA), and AMANO 8 (Amano, Japan).

Carbohydrate-Source Generating Enzyme present and/or added during Saccharification and/or Fermentation According to the invention a carbohydrate-source generating enzyme, preferably a glucoamylase, is present and/or added during saccharification and/or fermentation.

In a preferred embodiment the carbohydrate-source generating enzyme is a glucoamylase, of fungal origin, preferably from a strain of Aspergillus, preferably A. niger, A. awamori, or A. oryzae; or a strain of Trichoderma, preferably T. reesei; or a strain of Talaromyces, preferably T. emersonii.

Glucoamylase

According to the invention the glucoamylase present and/or added during saccharification and/or fermentation may be derived from any suitable source, e.g., derived from a microorganism or a plant. Preferred glucoamylases are of fungal or bacterial origin, selected from the group consisting of Aspergillus glucoamylases, in particular Aspergillus niger G1 or G2 glucoamylase (Boel et al., 1984, EMBO J. 3(5): 1097-1102), or variants thereof, such as those disclosed in WO 92/00381, WO 00/04136 and WO 01/04273 (from Novozymes, Denmark); the A. awamori glucoamylase disclosed in WO 84/02921, Aspergillus oryzae glucoamylase (Agric. Biol. Chem. 55(4): 941-949 (1991)), or variants or fragments thereof. Other Aspergillus glucoamylase variants include variants with enhanced thermal stability: G137A and G139A (Chen et al., 1996, Prot. Eng. 9: 499-505); D257E and D293E/Q (Chen et al., 1995, Prot. Eng. 8: 575-582); N182 (Chen et al., 1994, Biochem. J. 301: 275-281); disulphide bonds, A246C (Fierobe et al., 1996, Biochemistry 35: 8698-8704; and introduction of Pro residues in position A435 and S436 (Li et al., 1997, Protein Eng. 10: 1199-1204.

Other glucoamylases include Athelia rolfsii (previously denoted Corticium rolfsii) glucoamylase (see U.S. Pat. No. 4,727,026 and (Nagasaka et al., 1998, "Purification and properties of the raw-starch-degrading glucoamylases from Corticium rolfsii, Appl. Microbiol. Biotechnol. 50:323-330), Talaromyces glucoamylases, in particular derived from Talaromyces emersonii (WO 99/28448), Talaromyces leycettanus (U.S. Pat. No. Re. 32,153), Talaromyces duponti, Talaromyces thermophilus (U.S. Pat. No. 4,587,215). In a preferred embodiment the glucoamylase used during saccharification and/or fermentation is the Talaromyces emersonii glucoamylase disclosed in WO 99/28448.

Bacterial glucoamylases contemplated include glucoamylases from the genus Clostridium, in particular C. thermoamylolyticum (EP 135,138), and C. thermohydrosulfuricum (WO 86/01831) and Trametes cingulata, Pachykytospora papyracea; and Leucopaxillus giganteus all disclosed in WO 2006/069289; or Peniophora rufomarginata disclosed in WO 2007/124285; or a mixture thereof. Also hybrid glucoamylase are contemplated according to the invention. Examples the hybrid glucoamylases disclosed in WO 2005/045018. Specific examples include the hybrid glucoamylase disclosed in Tables 1 and 4 of Example 1 (which hybrids are hereby incorporated by reference).

In an embodiment the glucoamylase is derived from a strain of the genus Pycnoporus, in particular a strain of Pycnoporus as described in U.S. 61/264,977 published as WO 2011/066576 (SEQ ID NO: 2, 4 or 6), or from a strain of the genus Gloephyllum, in particular a strain of Gloephyllum as described in U.S. 61/406,741 published as WO 2011/068803 (SEQ ID NO: 2, 4, 6, 8, 10, 12, 14 or 16) or a strain of the genus Nigrofomes, in particular a strain of Nigrofomes sp. disclosed in U.S. 61/411,044 or PCT/US10/058375 (SEQ ID NO: 2) (all references hereby incorporated by reference). Contemplated are also glucoamylases which exhibit a high identity to any of above mention glucoamylases, i.e., at least 70%, at least 75%, at least 80%, at least 85%, at least 90%, at least 95%, at least 96%, at least 97%, at least 98%, at least 99% or even 100% identity to any one of the mature parts of the enzyme sequences mentioned above.

Contemplated are also glucoamylases which exhibit a high identity to any of above mention glucoamylases, i.e., at least 70%, at least 75%, at least 80%, at least 85%, at least 90%, at least 95%, at least 96%, at least 97%, at least 98%, at least 99% or even 100% identity to the mature enzymes sequences mentioned above.

Glucoamylases may in an embodiment be added in an amount of 0.0001-20 AGU/g DS, preferably 0.001-10 AGU/g DS, especially between 0.01-5 AGU/g DS, such as 0.1-2 AGU/g DS.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME™ ULTRA, SPIRIZYME™ ECXEL and AMG™ E (from Novozymes A/S); OPTIDEX™ 300, GC480, GC417 (from Genencor Int.); AMIGASE™ and AMIGASE™ PLUS (from DSM); G-ZYME™ G900, G-ZYME™ and G990 ZR (from Genencor Int.).

Maltogenic Amylase

The carbohydrate-source generating enzyme present and/or added during saccharification and/or fermentation may also be a maltogenic alpha-amylase. A "maltogenic alpha-amylase" (glucan 1,4-alpha-maltohydrolase, E.C. 3.2.1.133) is able to hydrolyze amylose and amylopectin to maltose in the alpha-configuration. A maltogenic amylase from Bacillus stearothermophilus strain NCIB 11837 is commercially available from Novozymes A/S. Maltogenic alpha-amylases are described in U.S. Pat. Nos. 4,598,048, 4,604,355 and 6,162,628, which are hereby incorporated by reference. The maltogenic amylase may in a preferred embodiment be added in an amount of 0.05-5 mg total protein/gram DS or 0.05-5 MANU/g DS.

A Composition Comprising Alpha-Amylase and Protease

A composition of the invention comprises a thermostable alpha-amylase and a thermostable protease. The composition may also optionally comprise a thermostable carbohydrate-source generating enzyme and optionally a pullulanase.

Therefore, in this aspect the invention relates to composition comprising an alpha-amylase and a protease, wherein the i) alpha-amylase has a T½ (min) at pH 4.5, 85° C., 0.12 mM $CaCl_2$) of at least 10;

ii) protease having a thermostability value of more than 20% determined as Relative Activity at 80° C./70° C.

The composition optionally further comprises a carbohydrate-source generating enzyme. Said carbohydrate-source generating enzyme may be a thermostable glucoamylase having a Relative Activity heat stability at 85° C. of at least 20%, at least 30%, preferably at least 35%.

The thermostable alpha-amylase is preferably a bacterial alpha-amylase, in particular of the genus *Bacillus*, such as a strain of *Bacillus stearothermophilus*, in particular a variant of a *Bacillus stearothermophilus* alpha-amylase, such as a variant of one shown in SEQ ID NO: 3 in WO 99/019467 or SEQ ID NO: 1 herein. Alpha-amylase variants are described further in the "Alpha-Amylase Present and/or Added During Liquefaction"-section above. The alpha-amylase may have a T½ (min) at pH 4.5, 85° C., 0.12 mM $CaCl_2$) of at least 15, such as at least 20, such as at least 25, such as at least 30, such as at least 40, such as at least 50, such as at least 60, such as between 10-70, such as between 15-70, such as between 20-70, such as between 25-70, such as between 30-70, such as between 40-70, such as between 50-70, such as between 60-70.

In an embodiment the alpha-amylase is selected from the group of *Bacillus* stearomthermphilus alpha-amylase variants, in particular truncated to be 491 amino acids long, with mutations selected from the group of:

I181*+G182*+N193F+V59A+Q89R+E129V+K177L+ R179E+H208Y+K220P+N224L+Q254S;

I181*+G182*+N193F+E129V+K177L+R179E; and

I181*+G182*+N193F+E129V+K177L+R179E+K220P+ N224L+S242Q+Q254S (using SEQ ID NO: 1 herein for numbering).

It should be understood that these alpha-amylases are only specific examples. Any alpha-amylase disclosed above in the "Alpha-Amylase Present and/or Added During Liquefaction"-section above may be used as the alpha-amylase component in a composition of the invention.

The protease has a thermostability of:
i) more than 30%, more than 40%, more than 50%, more than 60%, more than 70%, more than 80%, more than 90% determined as Relative Activity at 80° C./70° C.; or
ii) more than 12%, more than 14%, more than 16%, more than 18%, more than 20%, more than 25% determined as Relative Activity at 85° C./70° C.

In an embodiment the protease is a variant of the metallo protease show in SEQ ID NO: 3 derived from *Thermoascus aurantiacus* CGMCC No. 0670.

In a specific preferred embodiment the protease is a variant of the metallo protease derived from *Thermoascus aurantiacus* disclosed as the mature part of SEQ ID NO. 2 disclosed in WO 2003/048353 or the mature part of SEQ ID NO: 1 in WO 2010/008841 or SEQ ID NO: 3 herein with mutations selected from the group of:

A27K+D79L+Y82F+S87G+D104P+A112P+A126V+ D142L;

D79L+S87P+A112P+D142L; and

D79L+S87P+D142L.

In another preferred embodiment the protease is derived from a strain of *Pyrococcus furiosus*, such as the one shown in SEQ ID NO: 1 in U.S. Pat. No. 6,258,726 or SEQ ID NO: 13 herein.

In another embodiment the protease is one disclosed in SEQ ID NO: 13 herein or a protease having at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-B1 or SEQ ID NO: 13 herein. The *Pyroccus furiosus* protease can be purchased from Takara Shuzo Co. Ltd, Japan.

The *Pyrococcus furiosus* protease is a thermostable protease. The commercial product *Pyrococcus furiosus* protease (Pfu S) was found to have a thermostability of 110% (80° C./70° C.) and 103% (90° C./70° C.) at pH 4.5 determined as described in Example 2 herein.

It should be understood that these proteases are only examples. Any protease disclosed above in the "Protease Present and/or Added During Liquefaction" section above may be used as the protease component in a composition of the invention.

A composition of the invention may optionally further comprise a carbohydrate-source generating enzyme, in particular a glucoamylase, which has a heat stability at 85° C., pH 5.3, of at least 30%, preferably at least 35%.

In a preferred embodiment the carbohydrate-source generating enzyme is a glucoamylase having a relative activity of at least 80%, preferably at least 85%, preferably at least 90% at pH 4.5.

In a preferred embodiment carbohydrate-source generating enzyme is a glucoamylase having a pH stability at pH 4.5 of at least at least 80%, at least 85%, at least 90%, at least 95%, at least 100%.

Determination heat stability, and pH stability is described in the Example 4.

In a specific embodiment the carbohydrate-source generating enzyme is a glucoamylase, preferably derived from a strain of the genus *Penicillium*, especially a strain of *Penicillium oxalicum* disclosed in PCT/CN10/071753 published as WO 2011/127802. The glucoamylase may also be glucoamylase having at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in PCT/CN10/071753 published as WO 2011/127802.

In a preferred embodiment the carbohydrate-source generating enzyme is a variant of the *Penicillium oxalicum* glucoamylase disclosed as SEQ ID NO: 2 in PCT/CN10/071753 published as WO 2011/127802 and shown in SEQ ID NO: 9 and 14 herein, having a K79V substitution (using the mature sequence shown in SEQ ID NO: 14 for numbering). The K79V glucoamylase variant has reduced sensitivity to protease degradation relative to the parent as disclosed in co-pending U.S. application No. 61/531,189 (which is hereby incorporated by reference).

A composition of the invention may further comprise a pullulanase. In a preferred embodiment the pullulanase includes an X47 domain as disclosed in U.S. 61/289,040 published as WO 2011/087836 (which are hereby incorporated by reference).

Specifically the pullulanase may be derived from a strain from the genus *Thermococcus*, including *Thermococcus litoralis* and *Thermococcus hydrothermalis* or a hybrid thereof.

The pullulanase may be *Thermococcus hydrothermalis* pullulanase truncated at site X4 or a *Thermococcus hydrothermalis/T. litoralis* hybrid enzyme with truncation site X4 as disclosed in U.S. 61/289,040 published as WO 2011/087836 or shown in SEQ ID NO: 12 herein.

In an embodiment the invention relates to a composition comprising:
i) an alpha-amylase having a T½ (min) at pH 4.5, 85° C., 0.12 mM $CaCl_2$) of at least 10 derived from *Bacillus stearothermophilus*;
ii) a protease having a thermostability value of more than 20% determined as Relative Activity at 80° C./70° C. derived derived from *Pyrococcus furiosus* or *Thermoascus aurantiacus*; and optionally iii) a glucoamylase derived from *Penicillium oxalicum*.

The *Bacillus stearothermophilus* alpha-amylase, *Pyrococcus furiosus* or *Thermoascus aurantiacus* protease and/or *Penicillium oxalicum* glucoamylase may be any of the embodiments mentioned above.

In an embodiment the composition comprises a second alpha-amylase having a T½ (min) at pH 4.5, 85° C., 0.12 mM CaCl$_2$) of less than 10 derived from *Bacillus stearothermophilus*.

In an embodiment the ratio of enzyme protein (weight basis) between the components in a composition of the invention may be:

Alpha-Amylase: Glucoamylase: Protease: 0.1-10:0.5-50: 0.1-7, such as 0.5-3:1-30:0.5-2, such as 1-2:5-20:0.5-2.

Use of a Composition of the Invention

In a final aspect the invention relates to the use of a composition of the invention in a liquefaction process. In an embodiment liquefaction is a step in a process of the invention.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure, including definitions will be controlling.

Various references are cited herein, the disclosures of which are incorporated by reference in their entireties.

Materials & Methods

Materials:

Alpha-Amylase A: *Bacillus stearothermophilus* alpha-amylase with the mutations I181*+G182*+N193F truncated to 491 amino acids (SEQ ID NO: 1)

Alpha-Amylase 1093: *Bacillus stearothermophilus* alpha-amylase with the mutations I181*+G182*+N193F+E129V+K177L+R179E truncated to 491 amino acids (SEQ ID NO: 1)

Alpha-Amylase 1407: *Bacillus stearothermophilus* alpha-amylase with the mutations I181*+G182*+N193F+V59A+Q89R+E129V+K177L+R179E+H208Y+K220P+N224L+Q254S truncated to 491 amino acids (SEQ ID NO: 1)

Alpha-Amylase 1236: *Bacillus stearothermophilus* alpha-amylase with the mutations I181*+G182*+N193F+E129V+K177L+R179E+K220P+N224L+S242Q+Q254S truncated to 491 amino acids (SEQ ID NO: 1)

Protease 136: Metallo protease derived from *Thermoascus aurantiacus* CGMCC No. 0670 disclosed as amino acids 1-177 in SEQ ID NO: 3 herein and amino acids 1-177 in SEQ ID NO: 2 in WO 2003/048353 with the following mutations: D79L+Y82F+S87P+A112P+A126V+D142L Protease 196: Metallo protease derived from *Thermoascus aurantiacus* CGMCC No. 0670 disclosed as amino acids 1-177 in SEQ ID NO: 3 herein and amino acids 1-177 in SEQ ID NO: 2 in WO 2003/048353 with the following mutations: A27K+D79L+Y82F+S87G+D104P+A112P+A126V+D142L.

Protease 077: Metallo protease derived from *Thermoascus aurantiacus* CGMCC No. 0670 disclosed as amino acids 1-177 in SEQ ID NO: 3 herein and amino acids 1-177 in SEQ ID NO: 2 in WO 2003/048353 with the following mutations: A27K+D79L+S87P+A112P+D142L.

Protease Pfu: Protease derived from *Pyrococcus furiosus* purchased from Takara Bio Inc. (Japan) as Pfu Protease S (activity 10.5 mg/mL) and also shown in SEQ ID NO: 13 herein.

Glucoamylase PO: Mature part of the *Penicillium oxalicum* glucoamylase disclosed as SEQ ID NO: 2 in PCT/CN10/071753 published as WO 2011/127802 and shown in SEQ ID NO: 9 and 14 herein.

Glucoamylase PE001: Variant of the *Penicillium oxalicum* glucoamylase having a K79V substitution using the mature sequence shown in SEQ ID NO: 14 for numbering.

Glucoamylase BL: Blend of *Tamaromyces emersonii* glucoamylase disclosed in WO 99/28448 as SEQ ID NO: 7 and *Trametes cingulata* glucoamylase disclosed in WO 06/069289 in a ratio of about 9:1.

Glucoamylase BL2: Blend comprising *Talaromyces emersonii* glucoamylase disclosed in WO 99/28448, *Trametes cingulata* glucoamylase disclosed in WO 06/69289, and *Rhizomucor pusillus* alpha-amylase with *Aspergillus niger* glucoamylase linker and SBD disclosed as V039 in Table 5 in WO 2006/069290 as side activities (ratio about 65:15:1)

Substrate in Example 9: Ground corn from Corn LP, Iowa, USA (84.19% DS) and backset (6.27% DS).

Pullulanase TH: Pullulanase from *Thermococcus hydrothermalis* shown in SEQ ID NO: 11 herein.

Yeast: RED STAR ETHANOL RED™ available from Red Star/Lesaffre, USA.

Methods

Identity: The relatedness between two amino acid sequences or between two nucleotide sequences is described by the parameter "identity".

For purposes of the present invention the degree of identity between two amino acid sequences, as well as the degree of identity between two nucleotide sequences, may be determined by the program "align" which is a Needleman-Wunsch alignment (i.e. a global alignment). The program is used for alignment of polypeptide, as well as nucleotide sequences. The default scoring matrix BLOSUM50 is used for polypeptide alignments, and the default identity matrix is used for nucleotide alignments. The penalty for the first residue of a gap is −12 for polypeptides and −16 for nucleotides. The penalties for further residues of a gap are −2 for polypeptides, and −4 for nucleotides.

"Align" is part of the FASTA package version v20u6 (see Pearson and Lipman, 1988, "Improved Tools for Biological Sequence Analysis", PNAS 85:2444-2448, and Pearson, 1990, "Rapid and Sensitive Sequence Comparison with FASTP and FASTA," *Methods in Enzymology* 183:63-98). FASTA protein alignments use the Smith-Waterman algorithm with no limitation on gap size (see "Smith-Waterman algorithm", Smith and Waterman, 1981, *J. Mol. Biol.* 147: 195-197).

Protease Assays

AZCL-Casein Assay

A solution of 0.2% of the blue substrate AZCL-casein is suspended in Borax/NaH$_2$PO$_4$ buffer pH9 while stirring. The solution is distributed while stirring to microtiter plate (100 microL to each well), 30 microL enzyme sample is added and the plates are incubated in an Eppendorf Thermomixer for 30 minutes at 45° C. and 600 rpm. Denatured enzyme sample (100° C. boiling for 20 min) is used as a blank. After incubation the reaction is stopped by transferring the microtiter plate onto ice and the coloured solution is separated from the solid by centrifugation at 3000 rpm for 5 minutes at 4° C. 60 microL of supernatant is transferred to a microtiter plate and the absorbance at 595 nm is measured using a BioRad Microplate Reader.

pNA-Assay 50 microL protease-containing sample is added to a microtiter plate and the assay is started by adding 100 microL 1 mM pNA substrate (5 mg dissolved in 100 microL DMSO and further diluted to 10 mL with Borax/NaH$_2$PO$_4$ buffer pH 9.0). The increase in OD$_{405}$ at room temperature is monitored as a measure of the protease activity.

Glucoamylase Activity (AGU)

Glucoamylase activity may be measured in Glucoamylase Units (AGU).

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

AMG Incubation:
Substrate: maltose 23.2 mM
Buffer: acetate 0.1 M
pH: 4.30±0.05
incubation temperature: 37° C.±1
Reaction time: 5 minutes
Enzyme working range: 0.5-4.0 AGU/mL
Color Reaction:
GlucDH: 430 U/L
Mutarotase: 9 U/L
NAD: 0.21 mM
Buffer: phosphate 0.12 M; 0.15 M NaCl
pH: 7.60±0.05
Incubation temperature: 37° C.±1
Reaction time: 5 minutes
Wavelength: 340 nm A folder (EB-SM-0131.02/01) describing this analytical method in more detail is available on request from Novozymes A/S, Denmark, which folder is hereby included by reference.

Alpha-Amylase Activity (KNU)

The alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M Ca$^{2+}$; and pH 5.6) dextrinizes 5260 mg starch dry substance Merck Amylum solubile.

A folder EB-SM-0009.02/01 describing this analytical method in more detail is available upon request to Novozymes A/S, Denmark, which folder is hereby included by reference.

Determination of Pullulanase Activity (NPUN)

Endo-pullulanase activity in NPUN is measured relative to a Novozymes pullulanase standard. One pullulanase unit (NPUN) is defined as the amount of enzyme that releases 1 micro mol glucose per minute under the standard conditions (0.7% red pullulan (Megazyme), pH 5, 40° C., 20 minutes). The activity is measured in NPUN/ml using red pullulan.

1 mL diluted sample or standard is incubated at 40° C. for 2 minutes. 0.5 mL 2% red pullulan, 0.5 M KCl, 50 mM citric acid, pH 5 are added and mixed. The tubes are incubated at 40° C. for 20 minutes and stopped by adding 2.5 ml 80% ethanol. The tubes are left standing at room temperature for 10-60 minutes followed by centrifugation 10 minutes at 4000 rpm. OD of the supernatants is then measured at 510 nm and the activity calculated using a standard curve.

The present invention is described in further detail in the following examples which are offered to illustrate the present invention, but not in any way intended to limit the scope of the invention as claimed. All references cited herein are specifically incorporated by reference for that which is described therein.

EXAMPLES

Example 1

Stability of Alpha-Amylase Variants

The stability of a reference alpha-amylase (*Bacillus stearothermophilus* alpha-amylase with the mutations I181*+G182*+N193F truncated to 491 amino acids (SEQ ID NO: 1)) and alpha-amylase variants thereof was determined by incubating the reference alpha-amylase and variants at pH 4.5 and 5.5 and temperatures of 75° C. and 85° C. with 0.12 mM CaCl$_2$ followed by residual activity determination using the EnzChek® substrate (EnzChek® Ultra Amylase assay kit, E33651, Molecular Probes).

Purified enzyme samples were diluted to working concentrations of 0.5 and 1 or 5 and 10 ppm (micrograms/ml) in enzyme dilution buffer (10 mM acetate, 0.01% Triton X100, 0.12 mM CaCl$_2$, pH 5.0). Twenty microliters enzyme sample was transferred to 48-well PCR MTP and 180 microliters stability buffer (150 mM acetate, 150 mM MES, 0.01% Triton X100, 0.12 mM CaCl$_2$, pH 4.5 or 5.5) was added to each well and mixed. The assay was performed using two concentrations of enzyme in duplicates. Before incubation at 75° C. or 85° C., 20 microliters was withdrawn and stored on ice as control samples. Incubation was performed in a PCR machine at 75° C. and 85° C. After incubation samples were diluted to 15 ng/mL in residual activity buffer (100 mM Acetate, 0.01% Triton X100, 0.12 mM CaCl$_2$, pH 5.5) and 25 microliters diluted enzyme was transferred to black 384-MTP. Residual activity was determined using the EnzChek substrate by adding 25 microliters substrate solution (100 micrograms/ml) to each well. Fluorescence was determined every minute for 15 minutes using excitation filter at 485-P nm and emission filter at 555 nm (fluorescence reader is Polarstar, BMG). The residual activity was normalized to control samples for each setup.

Assuming logarithmic decay half life time (T % (min)) was calculated using the equation: T½ (min)=T(min)*LN (0.5)/LN(% RA/100), where T is assay incubation time in minutes, and % RA is % residual activity determined in assay.

Using this assay setup the half life time was determined for the reference alpha-amylase and variant thereof as shown in Table 1.

TABLE 1

| Mutations | T½ (min) (pH 4.5, 75° C., 0.12 mM CaCl₂) | T½ (min) (pH 4.5, 85° C., 0.12 mM CaCl₂) | T½ (min) (pH 5.5, 85° C., 0.12 mM CaCl₂) |
|---|---|---|---|
| Reference Alpha-Amylase A | 21 | 4 | 111 |
| Reference Alpha-Amylase A with the substitution V59A | 32 | 6 | 301 |
| Reference Alpha-Amylase A with the substitution V59E | 28 | 5 | 230 |
| Reference Alpha-Amylase A with the substitution V59I | 28 | 5 | 210 |
| Reference Alpha-Amylase A with the substitution V59Q | 30 | 6 | 250 |
| Reference Alpha-Amylase A with the substitutions V59A + Q89R + G112D + E129V + K177L + R179E + K220P + N224L + Q254S | 149 | 22 | ND |
| Reference Alpha-Amylase A with the substitutions V59A + Q89R + E129V + K177L + R179E + H208Y + K220P + N224L + Q254S | >180 | 28 | ND |
| Reference Alpha-Amylase A with the substitutions V59A + Q89R + E129V + K177L + R179E + K220P + N224L + Q254S + D269E + D281N | 112 | 16 | ND |
| Reference Alpha-Amylase A with the substitutions V59A + Q89R + E129V + K177L + R179E + K220P + N224L + Q254S + I270L | 168 | 21 | ND |
| Reference Alpha-Amylase A with the substitutions V59A + Q89R + E129V + K177L + R179E + K220P + N224L + Q254S + H274K | >180 | 24 | ND |
| Reference Alpha-Amylase A with the substitutions V59A + Q89R + E129V + K177L + R179E + K220P + N224L + Q254S + Y276F | 91 | 15 | ND |
| Reference Alpha-Amylase A with the substitutions V59A + E129V + R157Y + K177L + R179E + K220P + N224L + S242Q + Q254S | 141 | 41 | ND |
| Reference Alpha-Amylase A with the substitutions V59A + E129V + K177L + R179E + H208Y + K220P + N224L + S242Q + Q254S | >180 | 62 | ND |
| Reference Alpha-Amylase A with the substitutions V59A + E129V + K177L + R179E + K220P + N224L + S242Q + Q254S | >180 | 49 | >480 |
| Reference Alpha-Amylase A with the substitutions V59A + E129V + K177L + R179E + K220P + N224L + S242Q + Q254S + H274K | >180 | 53 | ND |
| Reference Alpha-Amylase A with the substitutions V59A + E129V + K177L + R179E + K220P + N224L + S242Q + Q254S + Y276F | >180 | 57 | ND |
| Reference Alpha-Amylase A with the substitutions V59A + E129V + K177L + R179E + K220P + N224L + S242Q + Q254S + D281N | >180 | 37 | ND |
| Reference Alpha-Amylase A with the substitutions V59A + E129V + K177L + R179E + K220P + N224L + S242Q + Q254S + M284T | >180 | 51 | ND |
| Reference Alpha-Amylase A with the substitutions V59A + E129V + K177L + R179E + K220P + N224L + S242Q + Q254S + G416V | >180 | 45 | ND |
| Reference Alpha-Amylase A with the substitutions V59A + E129V + K177L + R179E + K220P + N224L + Q254S | 143 | 21 | >480 |
| Reference Alpha-Amylase A with the substitutions V59A + E129V + K177L + R179E + K220P + N224L + Q254S + M284T | >180 | 22 | ND |
| Reference Alpha-Amylase A with the substitutions A91L + M96I + | >180 | 38 | ND |

TABLE 1-continued

| Mutations | T½ (min) (pH 4.5, 75° C., 0.12 mM CaCl$_2$) | T½ (min) (pH 4.5, 85° C., 0.12 mM CaCl$_2$) | T½ (min) (pH 5.5, 85° C., 0.12 mM CaCl$_2$) |
|---|---|---|---|
| E129V + K177L + R179E + K220P + N224L + S242Q + Q254S Reference Alpha-Amylase A with the substitutions E129V + K177L + R179E | 57 | 11 | 402 |
| Reference Alpha-Amylase A with the substitutions E129V + K177L + R179E + K220P + N224L + S242Q + Q254S | 174 | 44 | >480 |
| Reference Alpha-Amylase A with the substitutions E129V + K177L + R179E + K220P + N224L + S242Q + Q254S + Y276F + L427M | >180 | 49 | >480 |
| Reference Alpha-Amylase A with the substitutions E129V + K177L + R179E + K220P + N224L + S242Q + Q254S + M284T | >180 | 49 | >480 |
| Reference Alpha-Amylase A with the substitutions E129V + K177L + R179E + K220P + N224L + S242Q + Q254S + N376* + I377* | 177 | 36 | >480 |
| Reference Alpha-Amylase A with the substitutions E129V + K177L + R179E + K220P + N224L + Q254S | 94 | 13 | >480 |
| Reference Alpha-Amylase A with the substitutions E129V + K177L + R179E + K220P + N224L + Q254S + M284T | 129 | 24 | >480 |
| Reference Alpha-Amylase A with the substitutions E129V + K177L + R179E + S242Q | 148 | 30 | >480 |
| Reference Alpha-Amylase A with the substitutions E129V + K177L + R179V | 78 | 9 | >480 |
| Reference Alpha-Amylase A with the substitutions E129V + K177L + R179V + K220P + N224L + S242Q + Q254S | 178 | 31 | >480 |
| Reference Alpha-Amylase A with the substitutions K220P + N224L + S242Q + Q254S | 66 | 17 | >480 |
| Reference Alpha-Amylase A with the substitutions K220P + N224L + Q254S | 30 | 6 | 159 |
| Reference Alpha-Amylase A with the substitution M284T | 35 | 7 | 278 |
| Reference Alpha-Amylase A with the substitutions M284V | 59 | 13 | ND |

ND not determined

The results demonstrate that the alpha-amylase variants have a significantly greater half-life and stability than the reference alpha-amylase.

Example 2

Preparation of Protease Variants and Test of Thermostability
Chemicals used were commercial products of at least reagent grade.
Strains and Plasmids:
E. coli DH12S (available from Gibco BRL) was used for yeast plasmid rescue. pJTP000 is a S. cerevisiae and E. coli shuttle vector under the control of TPI promoter, constructed from pJC039 described in WO 01/92502, in which the Thermoascus aurantiacus M35 protease gene (WO 03/048353) has been inserted.
Saccharomyces cerevisiae YNG318 competent cells: MATa Dpep4[cir+] ura3-52, leu2-D2, his 4-539 was used for protease variants expression. It is described in J. Biol. Chem. 272(15): 9720-9727 (1997).

Media and Substrates
10× Basal solution: Yeast nitrogen base w/o amino acids (DIFCO) 66.8 g/L, succinate 100 g/l, NaOH 60 g/l.
SC-glucose: 20% glucose (i.e., a final concentration of 2%=2 g/100 mL)) 100 mL/L, 5% threonine 4 mL/L, 1% tryptophan 10 ml/l, 20% casamino acids 25 ml/l, 10× basal solution 100 ml/l. The solution is sterilized using a filter of a pore size of 0.20 micrometer. Agar (2%) and H$_2$O (approx. 761 mL) is autoclaved together, and the separately sterilized SC-glucose solution is added to the agar solution.
YPD: Bacto peptone 20 g/l, yeast extract 10 g/L, 20% glucose 100 mL/L.
YPD+Zn: YPD+0.25 mM ZnSO$_4$.
PEG/LiAc solution: 40% PEG4000 50 ml, 5 M Lithium Acetate 1 mL.
96 Well Zein Micro Titre Plate:
Each well contains 200 microL of 0.05-0.1% of zein (Sigma), 0.25 mM ZnSO$_4$ and 1% of agar in 20 mM sodium acetate buffer, pH 4.5.

DNA Manipulations

Unless otherwise stated, DNA manipulations and transformations were performed using standard methods of molecular biology as described in Sambrook et al. (1989) Molecular cloning: A laboratory manual, Cold Spring Harbor lab. Cold Spring Harbor, N.Y.; Ausubel, F. M. et al. (eds.) "Current protocols in Molecular Biology", John Wiley and Sons, 1995; Harwood, C. R. and Cutting, S. M. (Eds.).

Yeast Transformation

Yeast transformation was performed using the lithium acetate method. 0.5 microL of vector (digested by restriction endnucleases) and 1 microL of PCR fragments is mixed. The DNA mixture, 100 microL of YNG318 competent cells, and 10 microL of YEAST MAKER carrier DNA (Clontech) is added to a 12 mL polypropylene tube (Falcon 2059). Add 0.6 mL PEG/LiAc solution and mix gently. Incubate for 30 min at 30° C., and 200 rpm followed by 30 min at 42° C. (heat shock). Transfer to an eppendorf tube and centrifuge for 5 sec. Remove the supernatant and resolve in 3 mL of YPD. Incubate the cell suspension for 45 min at 200 rpm at 30° C. Pour the suspension to SC-glucose plates and incubate 30° C. for 3 days to grow colonies. Yeast total DNA are extracted by Zymoprep Yeast Plasmid Miniprep Kit (ZYMO research).

DNA Sequencing

*E. coli* transformation for DNA sequencing was carried out by electroporation (BIO-RAD Gene Pulser). DNA Plasmids were prepared by alkaline method (Molecular Cloning, Cold Spring Harbor) or with the Qiagen® Plasmid Kit. DNA fragments were recovered from agarose gel by the Qiagen gel extraction Kit. PCR was performed using a PTC-200 DNA Engine. The ABI PRISM™ 310 Genetic Analyzer was used for determination of all DNA sequences.

Construction of Protease Expression Vector

The *Themoascus* M35 protease gene was amplified with the primer pair Prot F (SEQ ID NO: 4) and Prot R (SEQ ID NO: 5). The resulting PCR fragments were introduced into *S. cerevisiae* YNG318 together with the pJC039 vector (described in WO 2001/92502) digested with restriction enzymes to remove the *Humicola insolens* cutinase gene.

The Plasmid in yeast clones on SC-glucose plates was recovered to confirm the internal sequence and termed as pJTP001.

Construction of Yeast Library and Site-Directed Variants

Library in yeast and site-directed variants were constructed by SOE PCR method (Splicing by Overlap Extension, see "PCR: A practical approach", p. 207-209, Oxford University press, eds. McPherson, Quirke, Taylor), followed by yeast in vivo recombination.

General Primers for Amplification and Sequencing

The primers AM34 (SEQ ID NO: 6) and AM35 (SEQ ID NO:7) were used to make DNA fragments containing any mutated fragments by the SOE method together with degenerated primers (AM34+Reverse primer and AM35+forward primer) or just to amplify a whole protease gene (AM34+AM35).

| PCR reaction system: | | Conditions: |
|---|---|---|
| 48.5 microL H$_2$O | 1 | 94° C. 2 min |
| 2 beads puRe Taq Ready-To-Go PCR (Amersham Biosciences) | 2 | 94° C. 30 sec |
| 0.5 microL × 2 100 pmole/microL of primers | 3 | 55° C. 30 sec |
| 0.5 microL template DNA | 4 | 72° C. 90 sec |
| | 2-4 | 25 cycles |
| | 5 | 72° C. 10 min |

DNA fragments were recovered from agarose gel by the Qiagen gel extraction Kit. The resulting purified fragments were mixed with the vector digest. The mixed solution was introduced into *Saccharomyces cerevisiae* to construct libraries or site-directed variants by in vivo recombination.

Relative Activity Assay

Yeast clones on SC-glucose were inoculated to a well of a 96-well micro titre plate containing YPD+Zn medium and cultivated at 28° C. for 3 days. The culture supernatants were applied to a 96-well zein micro titer plate and incubated at at least 2 temperatures (ex., 70° C. and 80° C.) for more than 4 hours or overnight. The turbidity of zein in the plate was measured as A630 and the relative activity (higher/lower temperatures) was determined as an indicator of thermoactivity improvement. The clones with higher relative activity than the parental variant were selected and the sequence was determined.

Remaining Activity Assay

Yeast clones on SC-glucose were inoculated to a well of a 96-well micro titre plate and cultivated at 28° C. for 3 days. Protease activity was measured at 65° C. using azo-casein (Megazyme) after incubating the culture supernatant in 20 mM sodium acetate buffer, pH 4.5, for 10 min at a certain temperature (80° C. or 84° C. with 4° C. as a reference) to determine the remaining activity. The clones with higher remaining activity than the parental variant were selected and the sequence was determined.

Azo-Casein Assay 20 microL of samples were mixed with 150 microL of substrate solution (4 mL of 12.5% azo-casein in ethanol in 96 mL of 20 mM sodium acetate, pH 4.5, containing 0.01% triton-100 and 0.25 mM ZnSO$_4$) and incubated for 4 hours or longer.

After adding 20 microL/well of 100% trichloroacetic acid (TCA) solution, the plate was centrifuge and 100 microL of supernatants were pipette out to measure A440.

Expression of Protease Variants in *Aspergillus oryzae*

The constructs comprising the protease variant genes were used to construct expression vectors for *Aspergillus*. The *Aspergillus* expression vectors consist of an expression cassette based on the *Aspergillus niger* neutral amylase II promoter fused to the *Aspergillus nidulans* triose phosphate isomerase non translated leader sequence (Pna2/tpi) and the *Aspergillus niger* amyloglycosidase terminator (Tamg). Also present on the plasmid was the *Aspergillus* selective marker amdS from *Aspergillus nidulans* enabling growth on acetamide as sole nitrogen source. The expression plasmids for protease variants were transformed into *Aspergillus* as described in Lassen et al., 2001, Appl. Environ. Microbiol. 67: 4701-4707. For each of the constructs 10-20 strains were isolated, purified and cultivated in shake flasks.

Purification of Expressed Variants

1. Adjust pH of the 0.22 μm filtered fermentation sample to 4.0.
2. Put the sample on an ice bath with magnetic stirring. Add (NH$_4$)$_2$SO$_4$ in small aliquots (corresponding to approx. 2.0-2.2 M (NH$_4$)$_2$SO$_4$ not taking the volume increase into account when adding the compound).
3. After the final addition of (NH$_4$)$_2$SO$_4$, incubate the sample on the ice bath with gentle magnetic stirring for min. 45 min.
4. Centrifugation: Hitachi himac CR20G High-Speed Refrigerated Centrifuge equipped with R20A2 rotor head, 5° C., 20,000 rpm, 30 min.
5. Dissolve the formed precipitate in 200 mL 50 mM Na-acetate pH 4.0.

6. Filter the sample by vacuum suction using a 0.22 micro m PES PLUS membrane (IWAKI).
7. Desalt/buffer-exchange the sample to 50 mM Na-acetate pH 4.0 using ultrafiltration (Vivacell 250 from Vivascience equipped with 5 kDa MWCO PES membrane) overnight in a cold room. Dilute the retentate sample to 200 ml using 50 mM Na-acetate pH 4.0. The conductivity of sample is preferably less than 5 mS/cm.
8. Load the sample onto a cation-exchange column equilibrated with 50 mM Na-acetate pH 4.0. Wash unbound sample out of the column using 3 column volumes of binding buffer (50 mM Na-acetate pH 4.0), and elute the sample using a linear gradient, 0-100% elution buffer (50 mM Na-acetate+1 M NaCl pH 4.0) in 10 column volumes.
9. The collected fractions are assayed by an endo-protease assay (cf. below) followed by standard SDS-PAGE (reducing conditions) on selected fractions. Fractions are pooled based on the endo-protease assay and SDS-PAGE.

Endo-Protease Assay

1. Protazyme OL tablet/5 ml 250 mM Na-acetate pH 5.0 is dissolved by magnetic stirring (substrate: endo-protease Protazyme AK tablet from Megazyme—cat. # PRAK 11/08).
2. With stirring, 250 microL of substrate solution is transferred to a 1.5 mL Eppendorf tube.
3. 25 microL of sample is added to each tube (blank is sample buffer).
4. The tubes are incubated on a Thermomixer with shaking (1000 rpm) at 50° C. for 15 minutes.
5. 250 microL of 1 M NaOH is added to each tube, followed by vortexing.
6. Centrifugation for 3 min. at 16,100×G and 25° C.
7. 200 microL of the supernatant is transferred to a MTP, and the absorbance at 590 nm is recorded.

TABLE 2

Relative Activity of protease variants. Numbering of substitution(s) starts from N-terminal of the mature peptide in amino acids 1 to 177 of SEQ ID NO: 3.

| | | Remaining Activity | |
|---|---|---|---|
| Variant | Substitution(s) and/or deletion(s) | 80° C. | 84° C. |
| JTP082 | ΔS5/D79L/S87P/A112P/D142L | | 53% |
| JTP091 | D79L/S87P/A112P/T124V/D142L | 43% | |
| JTP092 | ΔS5/N26R/D79L/S87P/A112P/D142L | | 60% |
| JTP095 | N26R/T46R/D79L/S87P/A112P/D142L | | 62% |
| JTP096 | T46R/D79L/S87P/T116V/D142L | | 67% |
| JTP099 | D79L/P81R/S87P/A112P/D142L | | 80% |
| JTP101 | A27K/D79L/S87P/A112P/T124V/D142L | 81% | |
| JTP116 | D79L/Y82F/S87P/A112P/T124V/D142L | 59% | |
| JTP117 | D79L/Y82F/S87P/A112P/T124V/D142L | 94% | |
| JTP127 | D79L/S87P/A112P/T124V/A126V/D142L | 53% | |

TABLE 3

Relative Activity of protease variants. Numbering of substitution(s) starts from N-terminal of the mature peptide in amino acids 1 to 177 of SEQ ID NO: 3.

| | | Relative Activity | |
|---|---|---|---|
| Variant | Substitutions | 80° C./ 70° C. | 85° C./ 70° C. |
| JTP050 | D79L S87P A112P D142L | 23% | 9% |
| JTP134 | D79L Y82F S87P A112P D142L | 40% | |
| JTP135 | S38T D79L S87P A112P A126V D142L | 62% | |
| JTP136 | D79L Y82F S87P A112P A126V D142L | 59% | |
| JTP137 | A27K D79L S87P A112P A126V D142L | 54% | |

TABLE 3-continued

Relative Activity of protease variants. Numbering of substitution(s) starts from N-terminal of the mature peptide in amino acids 1 to 177 of SEQ ID NO: 3.

| | | Relative Activity | |
|---|---|---|---|
| Variant | Substitutions | 80° C./ 70° C. | 85° C./ 70° C. |
| JTP145 | S49P D79L S87P A112P D142L | 59% | |
| JTP146 | S50P D79L S87P A112P D142L | 63% | |
| JTP148 | D79L S87P D104P A112P D142L | 64% | |
| JTP161 | D79L Y82F S87G A112P D142L | 30% | 12% |
| JTP180 | S70V D79L Y82F S87G Y97W A112P D142L | 52% | |
| JTP181 | D79L Y82F S87G Y97W D104P A112P D142L | 45% | |
| JTP187 | S70V D79L Y82F S87G A112P D142L | 45% | |
| JTP188 | D79L Y82F S87G D104P A112P D142L | 43% | |
| JTP189 | D79L Y82F S87G A112P A126V D142L | 46% | |
| JTP193 | Y82F S87G S70V D79L D104P A112P D142L | | 15% |
| JTP194 | Y82F S87G D79L D104P A112P A126V D142L | | 22% |
| JTP196 | A27K D79L Y82F S87G D104P A112P A126V D142L | | 18% |

TABLE 4

Relative Activity of protease variants. Numbering of substitution(s) starts from N-terminal of the mature peptide in amino acids 1 to 177 of SEQ ID NO: 3.

| Variant | Substitutions | Relative Activity 80° C./ 70° C. |
|---|---|---|
| JTP196 | A27K D79L Y82F S87G D104P A112P A126V D142L | 55% |
| JTP210 | A27K Y82F S87G D104P A112P A126V D142L | 36% |
| JTP211 | A27K D79L Y82F D104P A112P A126V D142L | 44% |
| JTP213 | A27K Y82F D104P A112P A126V D142L | 37% |

Example 3

Temperature Profile of Selected Protease Variants Using Purified Enzymes

Selected protease variants showing good thermostability were purified and the purified enzymes were used in a zein-BCA assay as described below. The remaining protease activity was determined at 60° C. after incubation of the enzyme at elevated temperatures as indicated for 60 min.

Zein-BCA Assay:

Zein-BCA assay was performed to detect soluble protein quantification released from zein by variant proteases at various temperatures.

Protocol:
1) Mix 10 microL of 10 micro g/mL enzyme solutions and 100 microL of 0.025% zein solution in a micro titer plate (MTP).
2) Incubate at various temperatures for 60 min.
3) Add 10 microL of 100% trichloroacetic acid (TCA) solution.
4) Centrifuge MTP at 3500 rpm for 5 min.
5) Take out 15 microL to a new MTP containing 100 microL of BCA assay solution (Pierce Cat #:23225, BCA Protein Assay Kit).
6) Incubate for 30 min. at 60° C.
7) Measure A562.

The results are shown in Table 5. All of the tested protease variants showed an improved thermostability as compared to the wild type (WT) protease.

TABLE 5

| | Zein-BCA assay | | | | | | |
|---|---|---|---|---|---|---|---|
| | Sample incubated 60 min at indicated temperatures (° C.) (micro g/mL Bovine serum albumin equivalent peptide released) | | | | | | |
| WT/Variant | 60° C. | 70° C. | 75° C. | 80° C. | 85° C. | 90° C. | 95° C. |
| WT | 94 | 103 | 107 | 93 | 58 | 38 | |
| JTP050 (D79L + S87P + A112P + D142L) | 86 | 101 | 107 | 107 | 104 | 63 | 36 |
| JTP077 (A27K + D79L + S87P + A112P + D142L) | 82 | 94 | 104 | 105 | 99 | 56 | 31 |
| JTP188 (D79L + Y82F + S87G + D104P + A112P + D142L) | 71 | 83 | 86 | 93 | 100 | 75 | 53 |
| JTP196 (A27K + D79L + Y82F + S87G + D104P + A112P + A126V + D142L) | 87 | 99 | 103 | 106 | 117 | 90 | 38 |

Example 4

Characterization of *Penicillium oxalicum* Glucoamylase

The *Penicillium oxalicum* glucoamylase is disclosed WO 2011/127802 and in SEQ ID NO: 9 herein.

Substrate.

Substrate: 1% soluble starch (Sigma S-9765) in deionized water

Reaction buffer: 0.1 M Acetate buffer at pH 5.3

Glucose concentration determination kit: Wako glucose assay kit (LabAssay glucose, WAKO, Cat #298-65701).

Reaction Condition.

20 microL soluble starch and 50 microL acetate buffer at pH5.3 were mixed. 30 microL enzyme solution (50 micro g enzyme protein/ml) was added to a final volume of 100 microL followed by incubation at 37° C. for 15 min.

The glucose concentration was determined by Wako kits.

All the work carried out in parallel.

Temperature Optimum.

To assess the temperature optimum of the *Penicillium oxalicum* glucoamylase the "Reaction condition"-assay described above was performed at 20, 30, 40, 50, 60, 70, 80, 85, 90 and 95° C. The results are shown in Table 6.

TABLE 6

| Temperature optimum | | | | | | | | | | |
|---|---|---|---|---|---|---|---|---|---|---|
| Temperature (° C.) | 20 | 30 | 40 | 50 | 60 | 70 | 80 | 85 | 90 | 95 |
| Relative activity (%) | 63.6 | 71.7 | 86.4 | 99.4 | 94.6 | 100.0 | 92.9 | 92.5 | 82.7 | 82.8 |

From the results it can be seen that the optimal temperature for *Penicillium oxalicum* glucoamylase at the given conditions is between 50° C. and 70° C. and the glucoamylase maintains more than 80% activity at 95° C.

Heat Stability.

To assess the heat stability of the *Penicillium oxalicum* glucoamylase the Reaction condition assay was modified in that the the enzyme solution and acetate buffer was preincubated for 15 min at 20, 30, 40, 50, 60, 70, 75, 80, 85, 90 and 95° C. Following the incubation 20 microL of starch was added to the solution and the assay was performed as described above.

The results are shown in Table 7.

TABLE 7

| Heat stability | | | | | | | | | | |
|---|---|---|---|---|---|---|---|---|---|---|
| Temperature (° C.) | 20 | 30 | 40 | 50 | 60 | 70 | 80 | 85 | 90 | 95 |
| Relative activity (%) | 91.0 | 92.9 | 88.1 | 100.0 | 96.9 | 86.0 | 34.8 | 36.0 | 34.2 | 34.8 |

From the results it can be seen that *Penicillium oxalicum* glucoamylase is stable up to 70° C. after preincubation for 15 min in that it maintains more than 80% activity.

pH Optimum.

To assess the pH optimum of the *Penicillium oxalicum* glucoamylase the Reaction condition assay described above was performed at pH 2.0, 3.0, 3.5, 4.0, 4.5, 5.0, 6.0 7.0, 8.0, 9.0, 10.0 and 11.0. Instead of using the acetate buffer described in the Reaction condition assay the following buffer was used 100 mM Succinic acid, HEPES, CHES, CAPSO, 1 mM $CaCl_2$, 150 mM KCl, 0.01% Triton X-100, pH adjusted to 2.0, 3.0, 3.5, 4.0, 4.5, 5.0, 6.0 7.0, 8.0, 9.0, 10.0 or 11.0 with HCl or NaOH.

The results are shown in Table 8.

TABLE 8

| pH optimum | | | | | | | | | | | | |
|---|---|---|---|---|---|---|---|---|---|---|---|---|
| pH | 2.0 | 3.0 | 3.5 | 4.0 | 4.5 | 5.0 | 6.0 | 7.0 | 8.0 | 9.0 | 10.0 | 11.0 |
| Relative activity (%) | 71.4 | 78.6 | 77.0 | 91.2 | 84.2 | 100.0 | 55.5 | 66.7 | 30.9 | 17.8 | 15.9 | 16.1 |

From the results it can be seen that *Penicillium oxalicum* glucoamylase at the given conditions has the highest activity at pH 5.0. The *Penicillium oxalicum* glucoamylase is active in a broad pH range in the it maintains more than 50% activity from pH 2 to 7.

pH Stability.

To assess the heat stability of the *Penicillium oxalicum* glucoamylase the Reaction condition assay was modified in that the enzyme solution (50 micro g/mL) was preincubated for 20 hours in buffers with pH 2.0, 3.0, 3.5, 4.0, 4.5, 5.0, 6.0 7.0, 8.0, 9.0, 10.0 and 11.0 using the buffers described under pH optimum. After preincubation, 20 microL soluble starch to a final volume of 100 microL was added to the solution and the assay was performed as described above.

The results are shown in Table 9.

TABLE 9

| pH stability | | | | | | | | | | | | |
|---|---|---|---|---|---|---|---|---|---|---|---|---|
| pH | 2.0 | 3.0 | 3.5 | 4.0 | 4.5 | 5.0 | 6.0 | 7.0 | 8.0 | 9.0 | 10.0 | 11.0 |
| Relative activity (%) | 17.4 | 98.0 | 98.0 | 103.2 | 100.0 | 93.4 | 71.2 | 90.7 | 58.7 | 17.4 | 17.0 | 17.2 |

From the results it can be seen that *Penicillium oxalicum* glucoamylase, is stable from pH 3 to pH 7 after preincubation for 20 hours and it decreases its activity at pH 8.

Example 5

Improved Ethanol Production Process
Mash Preparation:
Corn mashes were prepared through liquefaction in an 85° C. water bath for 2 hours. The dry solids (DS) content was around 30-33% and the backset ratio around 30%.
Mash Preparation:
Corn slurries were prepared for liquefaction by weighing out the specified amounts of ground corn, backset, and tap water into Nalgene bottles. Slurries were pH-adjusted to either 5.80 (Control) using 50% w/w NaOH or 4.50 (Study A, B) or 4.80 (Study C, D, E, F) using 40% v/v $H_2SO_4$. Control mashes using Alpha-Amylase A were made at pH 5.8. Aliquots of enzyme stock solutions were added. Bottles were tightly capped and placed into the water bath. Slurries were shaken vigorously once every 5 minutes for the first 30 minutes and then once every 30 minutes thereafter for a total of 2 hours. Mashes were immediately cooled in an ice bath. Urea and penicillin were then added to each mash to reach concentrations of 500 and 3 ppm, respectively.
Fermentation Setup:
Mashes were adjusted to pH 5.0 using 40% $H_2SO_4$ or 50% NaOH. Approximately 5 g of each mash was transferred into pre-weighed 15 mL plastic Falcon centrifuge tubes for fermentation. Typically, five replicate fermentations were prepared for each treatment. A small hole was drilled into the lid of each tube to allow for $CO_2$ release during fermentation. Following mash transfer, all tubes were reweighed to obtain their initial sample weights. Into each tube was then added 100 microL of rehydrated RED STAR ETHANOL RED yeast (rehydrated by weighing 5.5 g of dry yeast into a 150 mL Erlenmeyer flask, adding 100 mL of tap water and stirring in a 32° C. water bath for 30 minutes), an aliquot of diluted Glucoamylase BL (diluted in deionized water) needed to reach starting concentrations of 0.50 AGU/g DS. Deionized water was added to each tube such that the total volume of liquid added to each tube relative to the sample weight was the same. All tubes were then reweighed and then placed into a water bath set at 32° C. Fermentation was typically allowed to progress for 54 hours (if nothing else is stated). Tubes were vigorously vortexed after approximately 7 hours and then vortexed and reweighed twice per day for the remaining fermentation time. The grams of ethanol produced per gram of dry solids in each tube were calculated from the weight loss data according to the following equation:

$$\text{g ethanol/g } DS = \frac{\text{g } CO_2 \text{ weight loss} \times \frac{1 \text{ mol } CO_2}{44.0098 \text{ g } CO_2} \times \frac{1 \text{ mol ethanol}}{1 \text{ mol } CO_2} \times \frac{46.094 \text{ g ethanol}}{1 \text{ mol ethanol}}}{\text{g corn in tube} \times \% \text{ } DS \text{ of corn}}$$

Typically, 4 replicate tubes for each treatment were pulled after 54 hours of fermentation for HPLC analysis. Pulled samples were treated with 50 microL of 40% $H_2SO_4$ to stop fermentation and vortexed thoroughly. The samples were then centrifuged at 1460×g for 10 minutes and then filtered into HPLC vials through 0.45 micro m syringe filters. HPLC analysis was finally conducted on the samples to quantify the amounts of ethanol.

Results
An overview of the results is provided in Table 10.

TABLE 10

The doses of enzymes are listed in parentheses for each and are expressed as micro g EP/g DS.

| Study | pH | Enzymes In liquefaction step i). | Glucoamylase In SSF | HPLC EtOH vs Reference Alpha-Amylase A (Control) |
|---|---|---|---|---|
| A | 4.5 | Alpha-Amylase 1093 (1.4) Protease 077 (2) Pullulanase TH (2) | Glucoamylase BL | 3.0% |
| B | 4.5 | Alpha-amylase 1093 (2.75) Protease 077 (5) Pullulanase TH (2) | Glucoamylase BL | 1.6% |
| C | 4.8 | Alpha-amylase 1236 (2) Protease 136 (2) Glucoamylase PO (15) | Glucoamylase BL | 4.7% |
| D | 4.8 | Alpha-Amylase 1093 (2) Protease 180 (2, 1) Glucoamylase PO (10) | Glucoamylase BL | 4.2% (48 hrs) |
| E | 4.8 | Alpha-Amylase 1236 (2) Protease 188 (2) Glucoamylase PO (15) | Glucoamylase BL | 7.1% |
| F | 4.8 | Alpha-Amylase 1407 (1) Protease 196 (2) Glucoamylase PO (2) | Glucoamylase BL | 4.8% (at 72 hrs) |

*measured at 54 hours unless otherwise noted.

Example 6

Whole Corn Liquefaction and SSF Process Using the *P. oxalicum* AMG Variant (PE001)

The *Penicillium oxalicum* glucoamylase (Glucoamylase PO) variant, Glucoamylase PE001, showing reduced sensitivity to protease degradation, was tested in both whole corn liquefaction and starch saccharification (shown in next section). For the whole corn liquefactions, the Glucoamylase PE001 enzyme was added in different doses with a low pH amylase variant, Alpha-Amylase 1407. In some liquefactions, the Glucoamylase PE001 variant was tested with both the low pH amylase Alpha-Amylase 1407 and the thermostable protease Protease 196. In all experiments, the liquefactions were done using the automated system called the "Lab-O-Mat". This instrument controls the temperature and provides constant mixing. The other experimental conditions were: pH was 4.8 (for the liquefacts containing the Alpha-Amylase 1407 low pH amylase) or 5.8 (for the Alpha-Amylase A control), 32% dry solids, 85° C., 2 hours total time. The enzyme dosing schemes are shown in Table 11. The liquefied mashes were saccharified and fermented using Glucoamylase BL2 (at a dose of 0.5 AGU/gram dry solids for 54 hours at 32° C.).

TABLE 11

Enzyme dosing scheme for the three whole corn liquefaction experiments done using Glucoamylase PO protease nicking stable variant, i.e., Glucoamylase PE001.

| Alpha-Amylase (Dose) | Protease (Dose) | Glucoamylase (Dose) |
|---|---|---|
| Alpha-Amylase A (0.02% w/w corn) | None | None |
| Alpha-Amylase 1407 (1.4 µg EP/g DS) | None | None |
| Alpha-Amylase 1407 (1.4 µg EP/g DS) | None | Glucoamylase PO (P3HK) (10 µg EP/g DS) |
| Alpha-Alpha 1407 (1.4 µg EP/g DS) | None | Glucoamylase PE001 (10 µg EP/g DS) |
| Alpha-Amylase 1407 (1.4 µg EP/g DS) | Protease 196 (1 µg EP/g DS) | Glucoamylase PO (P3HK) (10 µg EP/g DS) |
| Alpha-Amylase 1407 (1.4 µg EP/g DS) | Protease 196 (1 µg EP/g DS) | Glucoamylase PE001 (10 µg EP/g DS) |

The HPLC quantified ethanol titers (in grams per liter) are shown in Table 12.

TABLE 12

Average ethanol titers and associated standard deviations, in grams per liter. The Protease196 is a temperature stable protease described in WO 2011/072191 and Alpha-Amylase 1407 is a low pH amylase described in WO 2011/082425.

| Treatment | Ethanol (Average ± Standard deviation; grams/liter) |
|---|---|
| Alpha-Amylase A control | 126.4 ± 0.3 |
| Alpha-Amylase 1407 (low pH alpha-amylase variant) control | 126.7 ± 0.3 |
| Glucoamylase PO (wild-type) P3HK (10 µg EP/g DS) | 127.2 ± 0.4 |
| Glucoamylase PE001 variant (10 µg EP/g DS) | 127.1 ± 0.5 |
| Glucoamylase PO (wild-type) P3HK (10 µg EP/g DS) + Protease 196 (1 µg EP/g DS) | 127.6 ± 0.4 |
| Glucoamylase PE001 variant (10 µg EP/g DS) + Protease 196 (1 µg EP/g DS) | 127.7 ± 0.2 |

Example 7

Thermostability of Protease Pfu

The thermostability of the *Pyrococcus furiosus* protease (Pfu S) purchased from Takara Bio, (Japan) was tested using the same methods as in Example 2. It was found that the thermostability (Relative Activity) was 110% at (80° C./70° C.) and 103% (90° C./70° C.) at pH 4.5.

Example 8

Ethanol Production Using Alpha-Amylase 1407 and Pfu Protease for Liquefaction

The purpose of this experiment was to evaluate application performance of Protease Pfu derived from *Pyrococcus furiosus* at pH 4.8 during liquefaction at 85° C. for 2 hours.

Liquefaction (Labomat)

Each liquefaction received ground corn (84.19% DS), backset (6.27% DS), and tap water targeting a total weight of 100 g at 32.50% Dry Solids (DS). Backset was blended at 30% w/w of total slurry weight. Initial slurry pH was approximately 5.2 and was adjusted to pH 4.8 with 40% v/v sulfuric acid prior to liquefaction. All enzymes were added according to the experimental design listed in Table 13 below. Liquefaction took place in a Labomat using the following conditions: 5° C./min. Ramp, 17 minute Ramp, 103 minute hold time, 40 rpm for the entire run, 200 mL stainless steel canisters. After liquefaction, all canisters were cooled in an ice bath and prepared for fermentation based on the protocol listed below under SSF.

Simultaneous Saccharification and Fermentation (SSF)

Each mash was adjusted to pH 5.0 with 50% w/w Sodium Hydroxide or 40% v/v sulfuric acid. Penicillin was applied to each mash to a total concentration of 3 ppm. The tubes were prepared with mash by aliquoting approximately 4.5 g of mash per 15 mL pre-drilled test tubes to allow $CO_2$ release. The test tubes sat, overnight, at 4° C. until the next morning.

All test tubes of mash were removed from cold storage and warmed up to 32° C. in the walk-in incubation chamber. Once warmed, Glucoamylase BL2, was dosed to each tube of mash at 0.50 AGU/g DS, water was added so that all tubes received 120 µL of liquid and each mash sample received 100 µL of rehydrated yeast. Rehydrated yeast was prepared by mixing 5.5 g of Fermentis RED STAR into 100 mL of 32° C. tap water for at least 15 minutes.

In monitoring $CO_2$ weight-loss over time, each unit of $CO_2$ generated and lost is converted to gram ethanol produced per gram of dry solids (g EtOH/gDS) by the following:

$$\text{g ethanol/g } DS = \frac{\text{g CO2 weight loss} \times \frac{1 \text{ mol CO2}}{44.0098 \text{ g CO2}} \frac{1 \text{ mol ethanol}}{1 \text{ mol CO2}} \frac{46.094 \text{ g ethanol}}{1 \text{ mol ethanol}}}{\text{g mash in tube } \% \text{ } DS \text{ of mash}}$$

HPLC Analysis

Fermentation sampling took place after 54 hours of fermentation by taking 3 tubes per treatment. Each sample was deactivated with 50 µL of 40% v/v $H_2SO_4$, vortexing, centrifuging at 1460×g for 10 minutes, and filtering through a 0.45 µm Whatman PP filter. 54 hour samples were analyzed under HPLC without further dilution. Samples were stored at 4° C. prior to and during HPLC analysis.

| HPLC system | Agilent's 1100/1200 series with Chem station software Degasser, Quaternary Pump, Auto-Sampler, Column Compartment/w Heater Refractive Index Detector (RI) |
|---|---|
| Column | Bio-Rad HPX-87H Ion Exclusion Column 300 mm × 7.8 mm part# 125-0140 Bio-Rad guard cartridge cation H part# 125-0129, Holder part# 125-0131 |
| Method | 0.005M $H_2SO_4$ mobile phase Flow rate: 0.6 ml/min Column temperature: 65° C. RI detector temperature: 55° C. |

The method quantified analyte(s) using calibration standard for ethanol (% w/v). A four point calibration including the origin is used for quantification.

Where applicable, data were analyzed using JMP software (Cary, N.C.) with Oneway ANOVA of pairs using Tukey-Kramer HSD or Dunnett's. Error bars denoting the 95% confidence level were established by multiplying the standard error of Oneway Anova analysis by 1.96.

TABLE 13

Experimental Plan.
Liquefaction at 85° C. (pH 4.8)

| Alpha-amylase | Dose μg/g DS | Protease | Dose μg/g DS | Glucoamylase | Dose μg/g DS |
|---|---|---|---|---|---|
| 1407 | 1.4 | — | — | — | — |
| 1407 | 1.4 | Pfu | 2 | — | — |
| 1407 | 1.4 | Pfu | 2 | PE001 | 10 |

Figure 1:
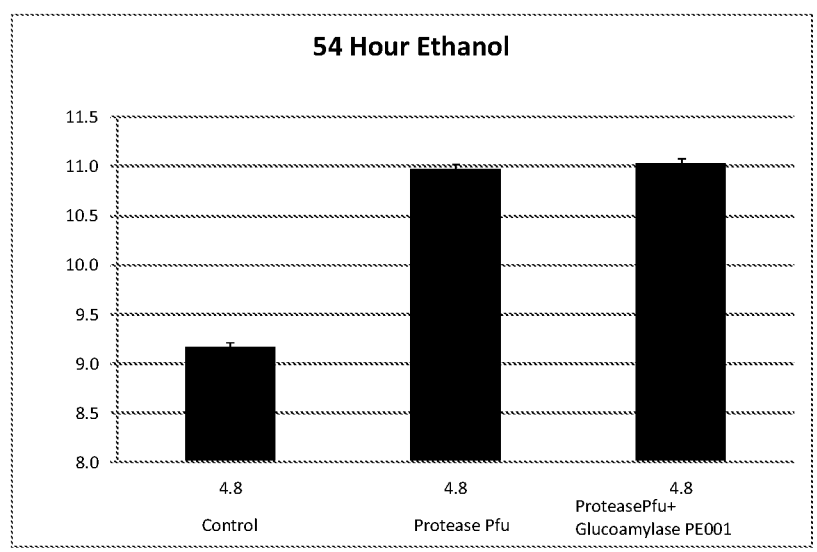
FIG. 1 shows a comparison of 54 hour ethanol for liquefactions (85° C.) prepared with Alpha-Amylase 1407 with and without Protease Pfu or Glucoamylase PE001 at pH 4.8.
Figure 2:
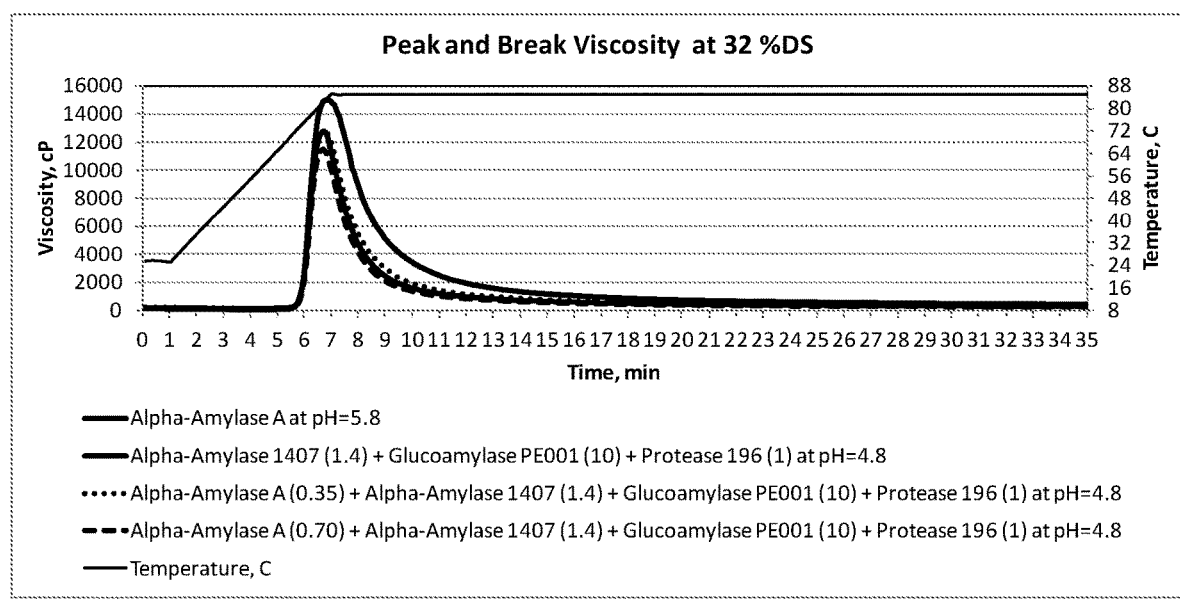
FIG. 2 shows the peak and break viscosity at 32% DS for the experiment in Example 10 comparing
Alpha-Amylase A (1.4 micro g) (pH 5.8);
Alpha-Amylase 1407 (1.4 micro g)+Glucoamylase PE001 (10 micro g)+Protease 196 (1 micro g) (pH 4.8);
Alpha-Amylase A (0.35 micro g)+Alpha-Amylase 1407 (1.4 micro g)+Glucoamylase PE001 (10 micro g)+Protease 196 (1 micro g) (pH 4.8);
Alpha-Amylase A (0.7 micro g)+Alpha-Amylase 1407 (1.4 micro g)+Glucoamylase PE001 (10 micro g)+Protease 196 (1 micro g) (pH 4.8)
Figure 3:
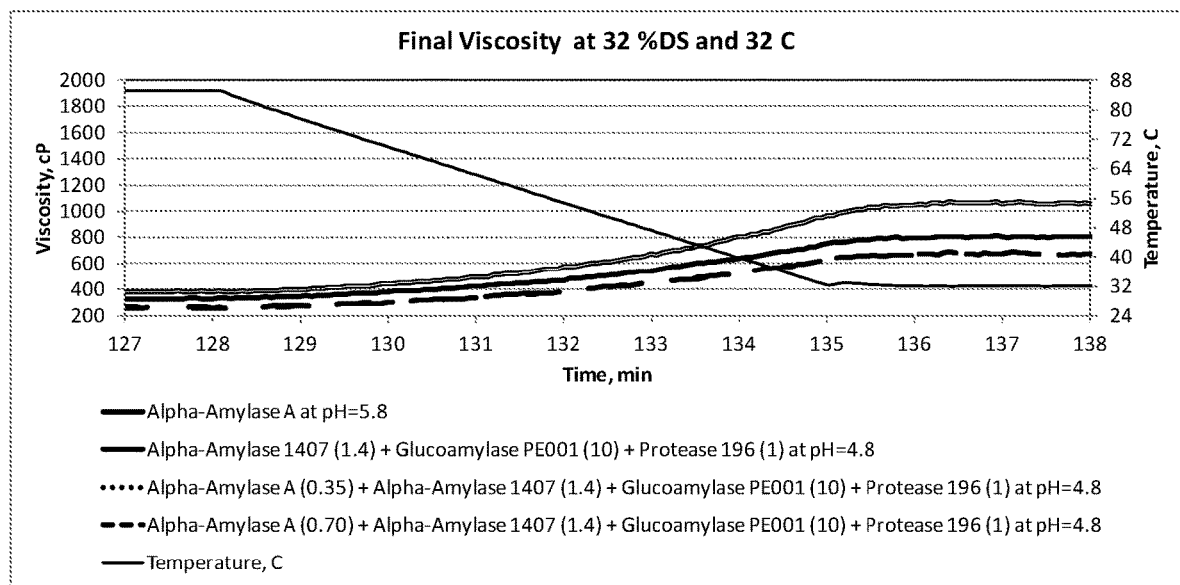
FIG. 3 shows the final viscosity at 32% DS at 32° C. for the experiment in Example 10 comparing
Alpha-Amylase A (1.4 micro g) (pH 5.8);
Alpha-Amylase 1407 (1.4 micro g)+Glucoamylase PE001 (10 micro g)+Protease 196 (1 micro g) (pH 4.8);
Alpha-Amylase A (0.35 micro g)+Alpha-Amylase 1407 (1.4 micro g)+Glucoamylase PE001 (10 micro g)+Protease 196 (1 micro g) (pH 4.8)

Table 14 and FIG. 1 below show the results:

| Treatment | pH | EtOH (% w/v) | EtOH (%Δ) | JMP Std Error | 95% CI |
|---|---|---|---|---|---|
| Control | 4.8 | 9.2 | 100% | 0.022 | 0.042 |
| Pfu | 4.8 | 11.0 | 120% | 0.022 | 0.042 |
| Pfu + PE001 | 4.8 | 11.0 | 120% | 0.022 | 0.042 |

Example 9

Ethanol Production Using Alpha-Amylase 1407 and Pfu Protease for Liquefaction

The purpose of this experiment was to evaluate application performance of Protease Pfu derived from *Pyrococcus furiosus* at pH 4.8 during liquefaction at 85° C. for 2 hours.

Liquefaction (Labomat)

Each liquefaction received ground corn (84.19% DS), backset (6.27% DS), and tap water targeting a total weight of 100 g at 32.50% Dry Solids (DS). Backset was blended at 30% w/w of total slurry weight. Initial slurry pH was approximately 5.2 and was adjusted to pH 4.8 with 40% v/v sulfuric acid prior to liquefaction. All enzymes were added according to the experimental design listed in Table 13 below. Liquefaction took place in a Labomat using the following conditions: 5° C./min. Ramp, 17 minute Ramp, 103 minute hold time, 40 rpm for the entire run, 200 mL stainless steel canisters. After liquefaction, all canisters were cooled in an ice bath and prepared for fermentation based on the protocol listed below under SSF.

Simultaneous Saccharification and Fermentation (SSF)

Each mash was adjusted to pH 5.0 with 50% w/w Sodium Hydroxide or 40% v/v sulfuric acid. Penicillin was applied to each mash to a total concentration of 3 ppm. The tubes were prepared with mash by aliquoting approximately 4.5 g of mash per 15 mL pre-drilled test tubes to allow $CO_2$ release. The test tubes sat, overnight, at 4° C. until the next morning.

All test tubes of mash were removed from cold storage and warmed up to 32° C. in the walk-in incubation chamber. Once warmed, Glucoamylase BL2, was dosed to each tube of mash at 0.50 AGU/g DS, water was added so that all tubes received 120 μL of liquid and each mash sample received 100 μL of rehydrated yeast. Rehydrated yeast was prepared by mixing 5.5 g of Fermentis RED STAR into 100 mL of 32° C. tap water for at least 15 minutes.

In monitoring $CO_2$ weight-loss over time, each unit of $CO_2$ generated and lost is converted to gram ethanol produced per gram of dry solids (g EtOH/gDS) by the following:

$$g\ ethanol/g\ DS = \frac{g\ CO2\ weight\ loss \times \frac{1\ mol\ CO2}{44.0098\ g\ CO2} \frac{1\ mol\ ethanol}{1\ mol\ CO2} \frac{46.094\ g\ ethanol}{1\ mol\ ethanol}}{g\ mash\ in\ tube\ \%\ DS\ of\ mash}$$

HPLC Analysis

Fermentation sampling took place after 54 hours of fermentation by taking 3 tubes per treatment. Each sample was deactivated with 50 μL of 40% v/v $H_2SO_4$, vortexing, centrifuging at 1460×g for 10 minutes, and filtering through a 0.45 μm Whatman PP filter. 54 hour samples were analyzed under HPLC without further dilution. Samples were stored at 4° C. prior to and during HPLC analysis.

| | |
|---|---|
| HPLC system | Agilent's 1100/1200 series with Chem station software Degasser, Quaternary Pump, Auto-Sampler, Column Compartment/w Heater Refractive Index Detector (RI) |
| Column | Bio-Rad HPX-87H Ion Exclusion Column 300 mm × 7.8 mm part# 125-0140 Bio-Rad guard cartridge cation H part# 125-0129, Holder part# 125-0131 |
| Method | 0.005M $H_2SO_4$ mobile phase Flow rate: 0.6 ml/min Column temperature: 65° C. RI detector temperature: 55° C. |

The method quantified analyte(s) using calibration standard for ethanol (% w/v). A four point calibration including the origin is used for quantification.

Where applicable, data were analyzed using JMP software (Cary, N.C.) with Oneway ANOVA of pairs using Tukey-Kramer HSD or Dunnett's. Error bars denoting the 95% confidence level were established by multiplying the standard error of Oneway Anova analysis by 1.96.

TABLE 15

Experimental Plan.
Liquefaction at 85° C. (pH 4.8)

| Alpha-amylase | Dose μg/g DS | Protease | Dose μg/g DS | Glucoamylase | Dose μg/g DS |
|---|---|---|---|---|---|
| 1407 | 1.4 | — | — | — | — |
| 1407 | 1.4 | Pfu | 2 | — | — |
| 1407 | 1.4 | Pfu | 2 | PE001 | 10 |

Table 16 below shows the results:

| Treatment | pH | EtOH (% w/v) | EtOH (%Δ) | JMP Std Error | 95% CI |
|---|---|---|---|---|---|
| Control | 4.8 | 9.2 | 100% | 0.022 | 0.042 |
| Pfu | 4.8 | 11.0 | 120% | 0.022 | 0.042 |
| Pfu + PE001 | 4.8 | 11.0 | 120% | 0.022 | 0.042 |

Example 10

Improved Lower Viscosity in the Ethanol Production Process

Corn Flour Preparation:

Corn flour from Corn LP, Iowa, USA, was sieved and its particle size distribution (PSD) defined. U.S. Standard Test Sieves with ASTM E-11 Specifications for number 12, 16, 20, 30, 40, and 60 sieves were used. The dry-solids (DS) content of the received flour was around 87.4%. Each experimental run was prepared to have the same PSD.

Viscosity Profile Setup and Determination in Rapid Visco Analyzer:

A Perten RVA-4 unit was used for measuring the viscosity profile during liquefaction. Corn slurries were prepared for liquefaction by weighing out specified amounts of sieved corn flour into a Perten metal cup that replicated the PSD of the received flour. A 40 gram slurry was made to 32% DS by adding tap water and the pH-adjusted to either 5.80 (Control) using 50% w/w NaOH or 4.80 using 40% v/v $H_2SO_4$. Aliquots of enzyme stock solutions were added prior to each run in the Perten RVA-4 and the amounts were also considered for getting the desired solids. The control slurry used Alpha-Amylase A at pH 5.8. The Perten RVA-4 was programmed to mix the slurry for 1 minute at 25° C., increase the slurry temperature from 25° C. to 85° C. in 6 minutes, hold the temperature at 85° C. constant for 2 hours, cool the liquefied mash temperature from 85° C. down to 32° C. in 7 minutes, and maintain the liquefied mash temperature at 32° C. for 5 minutes. During each run, the mixing was maintained constant at 210 rpm.

Results

An overview of the results is provided in Table 17 and shown in FIGS. 2-5.

TABLE 17

The doses of enzymes are listed in parentheses for each and are expressed as micro g EP/g DS.

| Experiment No. | Enzyme Description | Peak Viscosity | Average Viscosity Peak-to-Final | Final Viscosity | % Reduction of Peak Viscosity vs. Experiment 2 | % Reduction of Average Viscosity Peak-to-Final vs. Experiment 2 | % Reduction of Final Viscosity vs. Experiment 2 |
|---|---|---|---|---|---|---|---|
| 1 | Alpha-Amylase A (1.4) at pH = 5.8 | 12769 | 535 | 1078 | | | |
| 2 | Alpha-Amylase 1407 (1.4) + Glucoamylase PE001 (10) + Protease 196 (1) at pH = 4.8 | 15050 | 659 | 816 | | | |
| 3 | Alpha-Amylase A (1.4) + Glucoamylase PE001 (10) + Protease 196 (1) at pH = 4.8 | 11848 | 728 | 1831 | | | |
| 4 | Alpha-Amylase A (0.35) + Alpha-Amylase 1407 (1.4) + Glucoamylase PE001 (10) + Protease 196 (1) at pH = 4.8 | 12927 | 527 | 689 | 14% | 20% | 16% |
| 5 | Alpha-Amylase A (0.7) + Alpha-Amylase 1407 (1.4) + Glucoamylase PE001 (10) + Protease 196 (1) at pH = 4.8 | 11454 | 423 | 682 | 24% | 36% | 16% |

The present invention is further described in the following numbered paragraphs:

[1]. A process for producing fermentation products from starch-containing material comprising the steps of:

i) liquefying the starch-containing material at a pH in the range from 4.5-5.0 at a temperature in the range from 80-90° C. using:

an alpha-amylase having a T½ (min) at pH 4.5, 85° C., 0.12 mM $CaCl_2$) of at least 10;

optionally a protease having a thermostability value of more than 20% determined as Relative Activity at 80° C./70° C.;

ii) saccharifying using a carbohydrate-source generating enzyme;

iii) fermenting using a fermenting organism.

[2]. The process of paragraph [1], further comprises, prior to the liquefaction step i), the steps of:

a) reducing the particle size of the starch-containing material, preferably by dry milling;

b) forming a slurry comprising the starch-containing material and water.

[3]. The process of paragraph [1] or [2], wherein at least 50%, preferably at least 70%, more preferably at least 80%, especially at least 90% of the starch-containing material fit through a sieve with #6 screen.

[4]. The process of any of paragraphs [1]-[3], wherein the pH during liquefaction is between 4.5-4.8.

[5]. The process of any of paragraphs [1]-[4], wherein the temperature during liquefaction is in the range from 82–88° C., preferably around 85° C.

[6]. The process of any of paragraphs [1]-[5], wherein a jet-cooking step is carried out after liquefaction in step i).

[7]. The process of paragraph [6], wherein the jet-cooking is carried out at a temperature between 110-145° C., preferably 120-140° C., such as 125-135° C., preferably around 130° C. for about 1-15 minutes, preferably for about 3-10 minutes, especially around about 5 minutes.

[8]. The process of any of paragraphs [1]-[7], wherein saccharification and fermentation is carried out sequentially or simultaneously.

[9]. The process of any of paragraphs [1]-[8], wherein saccharification is carried out at a temperature from 20-75° C., preferably from 40-70° C., such as around 60° C., and at a pH between 4 and 5, such as about pH 4.5 or about 4.8.

[10]. The process of any of paragraphs [1]-[9], wherein fermentation or simultaneous saccharification and fermentation (SSF) is carried out carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours.

[11]. The process of any of paragraphs [1]-[10], wherein the fermentation product is recovered after fermentation, such as by distillation.

[12]. The process of any of paragraphs [1]-[11], wherein the fermentation product is an alcohol, preferably ethanol, especially fuel ethanol, potable ethanol and/or industrial ethanol.

[13]. The process of any of paragraphs [1]-[12], wherein the starch-containing starting material is whole grains.

[14]. The process of any of paragraphs [1]-[13], wherein the starch-containing material is derived from corn, wheat, barley, rye, milo, sago, cassava, manioc, tapioca, sorghum, rice or potatoes.

[15]. The process of any of paragraphs [1]-[14], wherein the fermenting organism is yeast, preferably a strain of Saccharomyces, especially a strain of Saccharomyces cerevisae.

[16]. The process of any of paragraphs [1]-[15], wherein the alpha-amylase has a T½ (min) at pH 4.5, 85° C., 0.12 mM CaCl$_2$) of at least 10, such as at least 15, such as at least 20, such as at least 25, such as at least 30, such as at least 40, such as at least 50, such as at least 60, such as between 10-70, such as between 15-70, such as between 20-70, such as between 25-70, such as between 30-70, such as between 40-70, such as between 50-70, such as between 60-70.

[17]. The process of any of paragraphs [1]-[16], wherein the alpha-amylase is a bacterial alpha-amylase.

[18]. The process of paragraph [17], wherein the bacterial alpha-amylase is derived from the genus Bacillus, such as a strain of Bacillus stearothermophilus, in particular a variant of a Bacillus stearothermophilus alpha-amylase, such as the one shown in SEQ ID NO: 3 in WO 99/019467 or SEQ ID NO: 1 herein, in particular the Bacillus stearothermophilus alpha-amylase is truncated, preferably to have around 491 amino acids.

[19]. The process of any of paragraphs [1]-[18], wherein the alpha-amylase variant has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 3 disclosed in WO 99/019467 or SEQ ID NO: 1 herein.

[20]. The process of any of paragraphs [1]-[19], wherein the alpha-amylase is derived from Bacillus stearothermophilus alpha-amylase truncated to have around 491 amino acids with the mutations selected from the group consisting of:
I181*+G182*+N193F+V59A+Q89R+E129V+K177L+ R179E+H208Y+K220P+N224L+Q254S;
I181*+G182*+N193F+E129V+K177L+R179E; and
I181*+G182*+N193F+E129V+K177L+R179E+K220P+ N224L+5242Q+Q254S.

[21]. The process of any of paragraphs [1]-[20], wherein a second alpha-amylase is added during liquefaction step i).

[22]. The process of paragraph [21], wherein the second alpha-amylase is of bacterial origin.

[23]. The process of paragraph [21] or [22], wherein the second alpha-amylase is derived from a strain of the genus Bacillus, such as a strain of Bacillus stearothermophilus, in particular a variant of a Bacillus stearothermophilus alpha-amylase, such as the one shown in SEQ ID NO: 3 in WO 99/019467 or SEQ ID NO: 1 herein, in particular wherein the second alpha-amylase is a truncated Bacillus stearothermophilus alpha-amylase, preferably to have around 491 amino acids.

[24]. The process of any of paragraphs [1]-[23], wherein the second alpha-amylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, or at least 100% identity to the mature part of the polypeptide of SEQ ID NO: 3 disclosed in WO 99/019467 or SEQ ID NO: 1 herein.

[25]. The process of any of paragraphs [21]-[24], wherein the second alpha-amylase has a T½ (min) at pH 4.5, 85° C., 0.12 mM CaCl$_2$) of below 10.

[26]. The process of any of paragraphs [21]-[25], wherein the second alpha-amylase has a T½ (min) at pH 4.5, 85° C., 0.12 mM CaCl$_2$) of below 8, such as below 7, such as below 6, such as below 5.

[27]. The process of any of paragraphs [21]-[26], wherein the second alpha-amylase has a T½ (min) at pH 4.5, 85° C., 0.12 mM CaCl$_2$) between 2 and 10, such as between 3 and 8, such as above 4 to 10, such as above 4 to 8.

[28]. The process of any of paragraphs [21]-[27], wherein the second alpha-amylase is derived from Bacillus stearothermophilus and has the following mutations I181*+G182* or I181*+G182*+N193F (using SEQ ID NO: 1 for numbering).

[29]. The process of any of paragraphs [1]-[28], comprising the steps of:
i) liquefying the starch-containing material at a pH in the range from 4.5-5.0 at a temperature in the range from 80–90° C. using:
an alpha-amylase having a T½ (min) at pH 4.5, 85° C., 0.12 mM CaCl$_2$) of at least 10, in particular an alpha-amylase of any one paragraphs 16-20 and further a second alpha-amylase having a T½ (min) at pH 4.5, 85° C., 0.12 mM CaCl$_2$) of less than 10, in particular a second alpha-amylase of any one of paragraphs 21-28;
a protease having a thermostability value of more than 20% determined as Relative Activity at 80° C./70° C.;

ii) saccharifying using a glucoamylase;
iii) fermenting using a fermenting organism.

[30]. The process of any of paragraphs [1]-[29], wherein the protease has a thermostability of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C.

[31]. The process of any of paragraphs [1]-[30], wherein the protease has a thermostability between 50 and 115%, such as between 50 and 70%, such as between 50 and 60%, such as between 100 and 120%, such as between 105 and 115% determined as Relative Activity at 80° C./70° C.

[32]. The process of any of paragraphs [1]-[31], wherein the protease has a thermostability of more than 12%, more than 14%, more than 16%, more than 18%, more than 20%, more than 25%, more than 30%, more than 40%, more that 50%, more than 60%, more than 70%, more than 80%, more than 90%, more than 100%, more than 110% determined as Relative Activity at 85° C./70° C.

[33]. The process of any of paragraphs [1]-[32], which protease variant has a thermostability between 10 and 50%, such as between 10 and 30%, such as between 10 and 25% determined as Relative Activity at 85° C./70° C.

[34]. The process of any of paragraphs [1]-[33], wherein the thermostability of the protease is between 50 and 110%, such as between 70 and 110%, such as between 90 and 110% determined as Relative Activity at 85° C./70° C.

[35]. The process of any of paragraphs [1]-[34], wherein the protease is fungal organism.

[36]. The process of any of paragraph [1]-[35], wherein the protease is a variant of the metallo protease derived from a strain of the genus *Thermoascus*, preferably a strain of *Thermoascus aurantiacus*, especially *Thermoascus aurantiacus* CGMCC No. 0670.

[37]. The process of any of paragraphs [1]-[36], wherein the protease is a variant of the metallo protease disclosed as the mature part of SEQ ID NO. 2 disclosed in WO 2003/048353 or the mature part of SEQ ID NO: 1 in WO 2010/008841 or SEQ ID NO: 3 herein.

[38]. The process of any of paragraphs [1]-[37], wherein the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 3 herein.

[39]. The process of any of paragraphs [1]-[38], wherein the protease is a variant of the *Thermoascus aurantiacus* protease shown in SEQ ID NO: 3 with the mutations selected from the group consisting of:
A27K+D79L+Y82F+S87G+D104P+A112P+A126V+D142L.
D79L+Y82F+S87G+A112P+D142L;
Y82F+S87G+S70V+D79L+D104P+A112P+D142L;
Y82F+S87G+D79L+D104P+A112P+A126V+D142L; and

[40]. The process of any of paragraphs [1]-[39], wherein the protease is of bacterial origin.

[41]. The process of any of paragraphs [1]-[40], wherein the protease is derived from a strain of *Pyrococcus*, preferably a strain of *Pyrococcus furiosus*.

[42]. The process of any of paragraphs [1]-[41] wherein the protease is the one shown in SEQ ID NO: 1 in U.S. Pat. No. 6,258,726 or SEQ ID NO: 13 herein.

[43]. The process of any of paragraphs [1]-[42], wherein the protease is one having at least 80%, such as at least 85%, such as at least 90%, such as at least 95%, such as at least 96%, such as at least 97%, such as at least 98%, such as at least 99% identity to SEQ ID NO: 1 in U.S. Pat. No. 6,258,726 or SEQ ID NO: 13 herein.

[44]. The process of any of paragraphs [1]-[43], further wherein a carbohydrate-source generating enzyme is present and/or added during liquefaction step i).

[45]. The process of paragraph [44], wherein the carbohydrate-source generating enzyme present and/or added during liquefaction step i) is a glucoamylase.

[46]. The process of paragraph [44] or [45], wherein the carbohydrate-source generating enzyme is a glucoamylase having a heat stability at 85° C., pH 5.3, of at least 30%, preferably at least 35%.

[47]. The process of any of paragraphs [44]-[46], wherein the carbohydrate-generating enzyme is a glucoamylase having a relative activity at pH 4.5 of at least 80%, preferably at least 85%, preferably at least 90%.

[48]. The process of any of paragraphs [44]-[47], wherein the carbohydrate-generating enzyme is a glucoamylase having a pH stability at pH 4.5 of at least at least 80%, at least 85%, at least 90%, at least 95%, at least 100%.

[49]. The process of any of paragraphs [44]-[48], wherein the carbohydrate-source generating enzyme is a glucoamylase, preferably derived from a strain of the genus *Penicillium*, especially a strain of *Penicillium oxalicum* disclosed as SEQ ID NO: 2 in PCT/CN10/071753 published as WO 2011/127802 or SEQ ID NO: 9 or 14 herein.

[50]. The process of any of paragraphs [44]-[49], wherein the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in PCT/CN10/071753 published as WO 2011/127802 or SEQ ID NO: 9 or 14 herein, or wherein the carbohydrate-source generating enzyme is a variant of the glucoamylase derived from a strain of *Penicillium oxalicum* having a K79V substitution in SEQ ID NO: 9 or 14 (using the mature sequence shown in SEQ ID NO: 14 for numbering).

[51]. The process of any of paragraphs [1]-[50], further wherein a glucoamylase is present and/or added during saccharification and/or fermentation.

[52]. The process of any of paragraphs [1]-[51], wherein the glucoamylase present and/or added during saccharification and/or fermentation is of fungal origin, preferably from a strain of *Aspergillus*, preferably *A. niger, A. awamori*, or *A. oryzae*; or a strain of *Trichoderma*, preferably *T. reesei*; or a strain of *Talaromyces*, preferably *T. emersonii*, or a strain of *Pycnoporus*, or a strain of *Gloeophyllum*.

[53]. The process of any of paragraphs [1]-[52], further wherein a pullulanase is present during liquefaction and/or saccharification.

[54]. The process of paragraph [53], wherein the pullulanase present or added during liquefaction step i) is a family GH57 pullulanase, wherein the pullulanase preferably includes an X47 domain as disclosed in U.S. 61/289,040 published as WO 2011/087836 or shown in SEQ ID NO: 12 herein.

[55]. The process of paragraph [53] or [54], wherein the pullulanase is derived from a strain from the genus *Ther-*

*mococcus*, including *Thermococcus litoralis* and *Thermococcus hydrothermalis* or a hybrid thereof.

[56]. The process of any of paragraphs [53]-[55], wherein the pullulanase is the truncated *Thermococcus hydrothermalis* pullulanase at site X4 or a *T. hydrothermalis/T. litoralis* hybrid enzyme with truncation site X4 disclosed in U.S. 61/289,040 published as WO 2011/087836 or shown in SEQ ID NO: 12 herein.

[57]. The process of any of paragraphs [1]-[56], comprising the steps of:
  i) liquefying the starch-containing material at a pH in the range from 4.5-5.0 at a temperature in the range from 80–90° C. using:
    an alpha-amylase derived from *Bacillus stearothermophilus* having a T½ (min) at pH 4.5, 85° C., 0.12 mM CaCl$_2$) of at least 10;
    a protease having a thermostability value of more than 20% determined as Relative Activity at 80° C./70° C. derived from *Pyrococcus furiosus* or *Thermoascus aurantiacus*;
  ii) saccharifying using a glucoamylase enzyme;
  iii) fermenting using a fermenting organism.

[58]. A composition comprising an alpha-amylase and a protease, wherein the i) alpha-amylase has a T½ (min) at pH 4.5, 85° C., 0.12 mM CaCl$_2$) of at least 10; ii) protease having a thermostability value of more than 20% determined as Relative Activity at 80° C./70° C.

[59]. The composition of paragraph [58], further comprising a carbohydrate-source generating enzyme.

[60]. The composition of paragraph [58] or [59], wherein the carbohydrate-source generating enzyme is a glucoamylase having a Relative Activity heat stability at 85° C. of at least 20%, at least 30%, preferably at least 35%.

[61]. The composition of any of paragraphs [58]-[60], wherein the alpha-amylase is a bacterial alpha-amylase, in particular of the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein, in particular wherein the *Bacillus stearothermophilus* alpha-amylase variant is truncated, preferably to have around 491 amino acids.

[62]. The process of any of paragraphs [58]-[61], wherein the alpha-amylase variant has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 3 disclosed in WO 99/019467 or SEQ ID NO: 1 herein.

[63]. The composition of any of paragraphs [58]-[62], wherein the alpha-amylase is derived from *Bacillus stearothermophilus* alpha-amylase truncated to have around 491 amino acids with the mutations selected from the group consisting of:
  I181*+G182*+N193F+V59A+Q89R+E129V+K177L+R179E+H208Y+K220P+N224L+Q254S;
  I181*+G182*+N193F+E129V+K177L+R179E; and
  I181*+G182*+N193F+E129V+K177L+R179E+K220P+N224L+S242Q+Q254S.

[64]. The composition of any of paragraphs [58]-[63], wherein the alpha-amylase has a T½ (min) at pH 4.5, 85° C., 0.12 mM CaCl$_2$) of at least 15, such as at least 20, such as at least 25, such as at least 30, such as at least 40, such as at least 50, such as at least 60, such as between 10-70, such as between 15-70, such as between 20-70, such as between 25-70, such as between 30-70, such as between 40-70, such as between 50-70, such as between 60-70.

[65]. The composition of any of paragraphs [58]-[64], further wherein the composition comprises a second alpha-amylase, in particular of bacterial origin.

[66]. The composition of paragraph [65], wherein the second alpha-amylase is derived from a strain of the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein, in particular wherein the second alpha-amylase is a truncated *Bacillus stearothermophilus* alpha-amylase, preferably to have around 491 amino acids.

[67]. The process of any of paragraphs [58]-[66], wherein the second alpha-amylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, or at least 100% identity to the mature part of the polypeptide of SEQ ID NO: 3 disclosed in WO 99/019467 or SEQ ID NO: 1 herein.

[68]. The composition of any of paragraphs [65]-[67], wherein the second alpha-amylase has a T½ (min) at pH 4.5, 85° C., 0.12 mM CaCl$_2$) of below 10.

[69]. The composition of any of paragraphs [65]-[68], wherein the second alpha-amylase has a T½ (min) at pH 4.5, 85° C., 0.12 mM CaCl$_2$) of below 8, such as below 7, such as below 6, such as below 5.

[70]. The composition of any of paragraphs [65]-[69], wherein the second alpha-amylase has a T½ (min) at pH 4.5, 85° C., 0.12 mM CaCl$_2$) between 2 and 10, such as between 3 and 8, such as above 4 to 10, such as above 4 to 8.

[71]. The composition of paragraph [64]-[70], wherein the second alpha-amylase is derived from *Bacillus stearothermophilus* and has the following mutations I181*+G182* or I181*+G182*+N193F (using SEQ ID NO: 1 for numbering).

[72]. The composition of any of paragraphs [58]-[71], comprising:
  an alpha-amylase having a T½ (min) at pH 4.5, 85° C., 0.12 mM CaCl$_2$) of at least 10;
  a second alpha-amylase having a T½ (min) at pH 4.5, 85° C., 0.12 mM CaCl$_2$) of less than 10;
  a protease having a thermostability value of more than 20% determined as Relative Activity at 80° C./70° C.;
  a thermostable glucoamylase.

[73]. The composition of paragraph [72], wherein the thermostable alpha-amylase is one of any of paragraphs 61-64.

[74]. The composition of paragraph [72] or [73], wherein the second alpha-amylase is one of any of paragraphs 65-71.

[75]. The composition of any of paragraphs [58]-[74], wherein the protease has a thermostability of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C.

[76]. The composition of any of paragraphs [58]-[75], wherein the protease has a thermostability between 50 and 115%, such as between 50 and 70%, such as between 50 and 60%, such as between 100 and 120%, such as between 105 and 115% determined as Relative Activity at 80° C./70° C.

[77]. The composition of any of paragraphs [58]-[76], wherein the protease has a thermostability of more than 12%, more than 14%, more than 16%, more than 18%, more than 20%, more than 25%, more than 30%, more than 40%, more that 50%, more than 60%, more than 70%, more than 80%, more than 90%, more than 100%, more than 110% determined as Relative Activity at 85° C./70° C.

[78]. The composition of any of paragraphs [58]-[77], wherein the protease has a thermostability of between 10 and 50%, such as between 10 and 30%, such as between 10 and 25% determined as Relative Activity at 85° C./70° C.

[79]. The composition of any of paragraphs [58]-[78], wherein the protease has a thermostability between 50 and 110%, such as between 70 and 110%, such as between 90 and 110% determined as Relative Activity at 85° C./70° C.

[80]. The composition of any of paragraphs [58]-[79], wherein the protease is a variant of the metallo protease derived from *Thermoascus aurantiacus* CGMCC No. 0670 show in SEQ ID NO: 3 herein.

[81]. The composition of any of paragraphs [58]-[80], wherein the protease variant of the *Thermoascus aurantiacus* protease shown in SEQ ID NO: 3 with the mutations selected from the group consisting of:

A27K+D79L+Y82F+S87G+D104P+A112P+A126V+D142L;
D79L+Y82F+S87G+A112P+D142L;
Y82F+S87G+S70V+D79L+D104P+A112P+D142L; and
Y82F+S87G+D79L+D104P+A112P+A126V+D142L.

[82]. The composition of any of paragraphs [58]-[81], wherein the protease is derived from a strain of *Pyrococcus*, preferably a strain of *Pyrococcus furiosus*.

[83]. The composition of any of paragraphs [58]-[82], wherein the protease is the one shown in SEQ ID NO: 1 in U.S. Pat. No. 6,258,726 or SEQ ID NO: 13 herein.

[84]. The composition of any of paragraphs [58]-[83], wherein the protease is one having at least 80%, such as at least 85%, such as at least 90%, such as at least 95%, such as at least 96%, such as at least 97%, such as at least 98%, such as at least 99% identity to SEQ ID NO: 1 in U.S. Pat. No. 6,258,726 or SEQ ID NO: 13 herein.

[85]. The composition of any of paragraphs [58]-[84], further comprising a carbohydrate-source generating enzyme, in particular a glucoamylase, which has a heat stability at 85° C., pH 5.3, of at least 30%, preferably at least 35%.

[86]. The composition of paragraph [85], wherein the carbohydrate-generating enzyme is a glucoamylase having a relative activity at pH 4.5 of at least 80%, preferably at least 85%, preferably at least 90%.

[87]. The composition of paragraph [85] or [86], wherein carbohydrate-generating enzyme is a glucoamylase having a pH stability at pH 4.5 of at least at least 80%, at least 85%, at least 90%, at least 95%, at least 100%.

[88]. The composition of any of paragraphs [85]-[87], wherein the carbohydrate-source generating enzyme is a glucoamylase, preferably derived from a strain of the genus *Penicillium*, especially a strain of *Penicillium oxalicum* disclosed as SEQ ID NO: 2 in PCT/CN10/071753 published as WO 2011/127802 or SEQ ID NO: 9 or 14 herein.

[89]. The composition of any of paragraphs [85]-[88], wherein the carbohydrate-source generating enzyme is a variant of the glucoamylase derived from a strain of *Penicillium oxalicum* disclosed as SEQ ID NO: 2 in WO 2011/127802 having a K79V substitution in SEQ ID NO: 9 or 14 (using the mature sequence shown in SEQ ID NO: 14 for numbering).

[90]. The composition of any of paragraphs [85]-[89], wherein the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in PCT/CN10/071753 published as WO 2011/127802 or shown in SEQ ID NO: 9 or 14 herein.

[91]. The composition of paragraphs [58]-[90], further comprising a pullulanase.

[92]. The composition of paragraph [91], wherein the pullulanase is a GH57 pullulanase, which preferably includes an X47 domain as disclosed in U.S. 61/289,040 published as WO 2011/087836.

[93]. The composition of paragraph [91] or [92], wherein the pullulanase is derived from a strain from the genus *Thermococcus*, including *Thermococcus litoralis* and *Thermococcus hydrothermalis* shown in SEQ ID NO: 10 herein, or a hybrid thereof.

[94]. The composition of paragraph [93], wherein the pullulanase is the truncated *Thermococcus hydrothermalis* pullulanase at site X4 or a *T. hydrothermalis/T. litoralis* hybrid enzyme with truncation site X4 disclosed in U.S. 61/289,040 published as WO 2011/087836 or shown in SEQ ID NO: 12 herein.

[95]. The composition of any of paragraphs [58]-[94] comprising:

i) an alpha-amylase having a T½ (min) at pH 4.5, 85° C., 0.12 mM CaCl$_2$) of at least 10 derived from *Bacillus stearothermophilus*;

ii) a protease having a thermostability value of more than 20% determined as Relative Activity at 80° C./70° C. derived derived from *Pyrococcus furiosus* or *Thermoascus aurantiacus*; and optionally iii) a glucoamylase derived from *Penicillium oxalicum*.

[96]. The composition of paragraph [95], wherein the composition further comprising a second alpha-amylase having a T½ (min) at pH 4.5, 85° C., 0.12 mM CaCl$_2$) of less than 10 derived from *Bacillus stearothermophilus*.

[97]. Use of a composition of any of paragraphs [58]-[96] in a liquefaction process.

[98]. The use according to paragraph 97, wherein liquefaction is carried out as defined in any of paragraphs [1]-[57].

The invention claimed is:

1. A process for producing fuel ethanol from corn comprising:
   i) liquefying the corn at a temperature above 80° C. using:
      a thermostable bacterial alpha-amylase; and
      a thermostable bacterial serine protease that has a thermostability value of more than 20% determined as Relative Activity at 80° C./70° C.;
   ii) saccharifying the liquefied material obtained in step i) using a glucoamylase; and
   iii) fermenting the saccharified material obtained in step ii) using a yeast fermenting organism.

2. The process of claim 1, wherein the alpha-amylase is a variant of a *Bacillus stearothermophilus* alpha-amylase.

3. The process of claim 1, wherein the alpha-amylase variant has at least 80%, but less than 100% identity to the mature part of the polypeptide of SEQ ID NO: 1 herein.

4. The process of claim 3, wherein the alpha-amylase is truncated to have 491 amino acids.

5. The process of claim 1, wherein the alpha-amylase is a truncated *Bacillus stearothermophilus* alpha-amylase with the mutations selected from the group consisting of:
   I181*+G182*+N193F+V59A+Q89R+E129V+K177L+R179E+H208Y+K220P+N224L+Q254S;
   I181*+G182*+N193F+E129V+K177L+R179E; and
   I181*+G182*+N193F+E129V+K177L+R179E+K220P+N224L+S242Q+Q254S; wherein each position corresponds to a position in the amino acid sequence set forth in SEQ ID NO: 1.

6. The process of claim 1, wherein the protease is a serine protease.

7. The process of claim 1, wherein the protease is from a strain of *Pyrococcus*.

8. The process of claim 1, wherein the protease is the *Pyrococcus furiosus* protease of SEQ ID NO: 13, or one having at least 90% sequence identity thereto.

9. The process of claim 8, wherein the protease has as at least 95% sequence identity to SEQ ID NO: 13.

10. The process of claim 1, further wherein a thermostable glucoamylase is present and/or added during liquefaction step i).

11. The process of claim 10, wherein the glucoamylase has a heat stability at 85° C., pH 5.3, of at least 30%.

12. The process of claim 10, wherein the glucoamylase is from a strain of the genus *Penicillium*.

13. The process of claim 12, wherein the glucoamylase is a *Penicillium oxalicum* glucoamylase having the amino acid sequence of SEQ ID NO: 9 or 14.

14. The process of claim 13, wherein the glucoamylase has a K79V substitution in SEQ ID NO: 9 or 14 (using the mature sequence shown in SEQ ID NO: 14 for numbering).

15. The process of claim 13, wherein the glucoamylase has at least 80% identity to the mature polypeptide shown in SEQ ID NO: 9 or 14 herein.

16. The process of claim 1, wherein a pullulanase is present during liquefaction and/or saccharification.

17. The process of claim 1, wherein the glucoamylase is of fungal origin.

18. The process of claim 17, wherein the glucoamylase is from a strain selected from the group consisting of *Aspergillus*, *Trichoderma*, *Talaromyces*, *Pycnoporus*, and *Gloeophyllum*.

19. The process of claim 1, wherein the alpha-amylase has a T½ (min) at pH 4.5, 85° C., 0.12 mM $CaCl_2$)) of at least 10.

20. The process of claim 1, wherein the alpha-amylase has a T½ (min) at pH 4.5, 85° C., 0.12 mM $CaCl_2$)) of at least 15.

21. The process of claim 1, wherein the alpha-amylase has a T½ (min) at pH 4.5, 85° C., 0.12 mM $CaCl_2$)) of at least 20.

22. The process of claim 1, wherein the alpha-amylase has a T½ (min) at pH 4.5, 85° C., 0.12 mM $CaCl_2$)) of at least 25.

23. The process of claim 1, wherein the alpha-amylase has a T½ (min) at pH 4.5, 85° C., 0.12 mM $CaCl_2$)) of at least 30.

24. The process of claim 1, wherein the alpha-amylase has a T½ (min) at pH 4.5, 85° C., 0.12 mM $CaCl_2$)) of at least 40.

25. The process of claim 1, wherein the alpha-amylase has a T½ (min) at pH 4.5, 85° C., 0.12 mM $CaCl_2$)) of at least 50.

26. The process of claim 1, wherein the alpha-amylase has a T½ (min) at pH 4.5, 85° C., 0.12 mM $CaCl_2$)) of at least 60.

27. The process of claim 1, wherein the alpha-amylase has a T½ (min) at pH 4.5, 85° C., 0.12 mM $CaCl_2$)) of at least 10.

28. The process of claim 1, wherein the protease has a thermostability value of more than 20% determined as Relative Activity at 80° C./70° C.

29. The process of claim 1, wherein the protease has a thermostability value of more than 30% determined as Relative Activity at 80° C./70° C.

30. The process of claim 1, wherein the protease has a thermostability value of more than 40% determined as Relative Activity at 80° C./70° C.

31. The process of claim 1, wherein the protease has a thermostability value of more than 50% determined as Relative Activity at 80° C./70° C.

32. The process of claim 1, wherein the protease has a thermostability value of more than 60% determined as Relative Activity at 80° C./70° C.

33. The process of claim 1, wherein the protease has a thermostability value of more than 70% determined as Relative Activity at 80° C./70° C.

34. The process of claim 1, wherein the protease has a thermostability value of more than 80% determined as Relative Activity at 80° C./70° C.

35. The process of claim 1, wherein the protease has a thermostability value of more than 90% determined as Relative Activity at 80° C./70° C.

36. The process of claim 1, wherein the protease has a thermostability value of more than 10% determined as Relative Activity at 85° C./70° C.

37. The process of claim 1, wherein the protease has a thermostability value of more than 12% determined as Relative Activity at 85° C./70° C.

38. The process of claim 1, wherein the protease has a thermostability value of more than 14% determined as Relative Activity at 85° C./70° C.

39. The process of claim 1, wherein the protease has a thermostability value of more than 16% determined as Relative Activity at 85° C./70° C.

40. The process of claim 1, wherein the protease has a thermostability value of more than 18% determined as Relative Activity at 85° C./70° C.

41. The process of claim 1, wherein the protease has a thermostability value of more than 20% determined as Relative Activity at 85° C./70° C.

42. The process of claim 1, wherein the protease has a thermostability value of more than 25% determined as Relative Activity at 85° C./70° C.

43. The process of claim 1, wherein the protease has a thermostability value of more than 20% determined as Remaining Activity at 80° C.

44. The process of claim 1, wherein the protease has a thermostability value of more than 30% determined as Remaining Activity at 80° C.

45. The process of claim 1, wherein the protease has a thermostability value of more than 40% determined as Remaining Activity at 80° C.

46. The process of claim 1, wherein the protease has a thermostability value of more than 50% determined as Remaining Activity at 80° C.

47. The process of claim 1, wherein the protease has a thermostability value of more than 60% determined as Remaining Activity at 80° C.

48. The process of claim 1, wherein the protease has a thermostability value of more than 70% determined as Remaining Activity at 80° C.

49. The process of claim 1, wherein the protease has a thermostability value of more than 80% determined as Remaining Activity at 80° C.

50. The process of claim 1, wherein the protease has a thermostability value of more than 90% determined as Remaining Activity at 80° C.

51. The process of claim 1, wherein the protease has a thermostability value of more than 20% determined as Remaining Activity at 84° C.

52. The process of claim 1, wherein the protease has a thermostability value of more than 30% determined as Remaining Activity at 84° C.

53. The process of claim 1, wherein the protease has a thermostability value of more than 40% determined as Remaining Activity at 84° C.

54. The process of claim 1, wherein the protease has a thermostability value of more than 50% determined as Remaining Activity at 84° C.

55. The process of claim 1, wherein the protease has a thermostability value of more than 60% determined as Remaining Activity at 84° C.

56. The process of claim 1, wherein the protease has a thermostability value of more than 70% determined as Remaining Activity at 84° C.

57. The process of claim 1, wherein the protease has a thermostability value of more than 80% determined as Remaining Activity at 84° C.

58. The process of claim 1, wherein the protease has a thermostability value of more than 90% determined as Remaining Activity at 84° C.

59. The process of claim 1, further wherein a thermostable glucoamylase is present and/or added during liquefaction step i).

60. The process of claim 59, wherein the glucoamylase has a heat stability at 85° C., pH 5.3, of at least 20%.

61. The process of claim 59, wherein the glucoamylase has a heat stability at 85° C., pH 5.3, of at least 30%.

62. The process of claim 59, wherein the glucoamylase has a heat stability at 85° C., pH 5.3, of at least 35%.

63. The process of claim 59, wherein the glucoamylase has a relative activity at pH 4.5 of at least 80%.

64. The process of claim 59, wherein the glucoamylase has a relative activity at pH 4.5 of at least 85%.

65. The process of claim 59, wherein the glucoamylase has a relative activity at pH 4.5 of at least 90%.

66. The process of claim 59, wherein the glucoamylase has a pH stability at pH 4.5 of at least 80%.

67. The process of claim 59, wherein the glucoamylase has a pH stability at pH 4.5 of at least 85%.

68. The process of claim 59, wherein the glucoamylase has a pH stability at pH 4.5 of at least 90%.

69. The process of claim 59, wherein the glucoamylase has a pH stability at pH 4.5 of at least 95%.

70. The process of claim 59, wherein the glucoamylase has a pH stability at pH 4.5 of at least 100%.

71. The process of claim 1, wherein saccharification and fermentation are carried out simultaneously.

72. The process of claim 71, wherein fermentation or simultaneous saccharification and fermentation (SSF) are carried out at a temperature from 25 degrees centigrade to 40 degrees centigrade.

73. The process of claim 71, wherein fermentation or simultaneous saccharification and fermentation (SSF) are carried out at a temperature from 28 degrees centigrade to 35 degrees centigrade.

74. The process of claim 71, wherein fermentation or simultaneous saccharification and fermentation (SSF) are carried out at a temperature from 30 degrees centigrade to 34 degrees centigrade.

75. The process of claim 71, wherein fermentation or simultaneous saccharification and fermentation (SSF) are carried out at a temperature of around 32 degrees centigrade.

76. The process of claim 1, wherein saccharification is carried out at a temperature from 20-75 degrees centigrade.

77. The process of claim 1, wherein saccharification is carried out at a temperature from 40-70 degrees centigrade.

78. The process of claim 1, wherein saccharification is carried out at a temperature of around 60 degrees centigrade.

79. The process of claim 1, wherein fermentation is ongoing for 6 to 120 hours.

80. The process of claim 1, wherein fermentation is ongoing for 24 to 96 hours.

81. The process of claim 1, wherein the yeast fermenting organism is a strain of *Saccharomyces*.

82. The process of claim 1, wherein the yeast fermenting organism is a strain of *Saccharomyces cerevisiae*.

83. The process of claim 1, wherein the liquefying step is done at a pH in the range of about 4.5-5.0.

84. The process of claim 1, wherein the liquefying step is done at a temperature in the range of about 80° C.-90° C.

85. The process of claim 1, wherein the liquefying step lasts for 1-3 hours.

86. The process of claim 1, wherein the liquefying step lasts for 2 hours.

87. The process of claim 1, wherein prior to the liquefying step i), the process further comprises the steps of: a) reducing the particle size of the corn; and b) forming an aqueous slurry comprising the corn and water.

88. The process of claim 87, wherein the particle size of the corn is reduced by dry milling.

89. The process of claim 87, wherein the aqueous slurry contains from 10-55 w/w percent dry solids (DS) of the corn.

90. The process of claim 87, wherein the aqueous slurry contains from 25-45 w/w-percent dry solids (DS) of the corn.

91. The process of claim 87, wherein the aqueous slurry contains from 30-40 w/w-percent dry solids (DS) of the corn.

92. The process of claim 1, wherein the fuel ethanol is recovered after fermentation.

93. The process of claim 1, wherein the fuel ethanol is recovered after fermentation by distillation.

94. The process of claim 1, wherein:
(i) the alpha-amylase has a T½ (min) at pH 4.5, 85° C., 0.12 mM CaCl2) of at least 10; and
(ii) the protease has a thermostability value of more than 90% determined as Relative Activity at 80° C./70° C.

95. The process of claim 1, wherein:
(i) the alpha-amylase has a T½ (min) at pH 4.5, 85° C., 0.12 mM CaCl2) of at least 10;
(ii) the protease has a thermostability value of more than 90% determined as Relative Activity at 80° C./70° C.;
(iii) the temperature during liquefying step i) is between 80° C.-95° C.;
(iv) the pH during liquefying step i) is from 4.5-5.0;
(v) the glucoamylase is of fungal origin; and
(vi) the saccharifying step (ii) and fermenting step (iii) are carried out as a simultaneous saccharification and fermentation.

96. The process of claim 1, wherein:
(i) the alpha-amylase has a T½ (min) at pH 4.5, 85° C., 0.12 mM CaCl2) of at least 20;
(ii) the protease has a thermostability value of more than 90% determined as Relative Activity at 80° C./70° C.;
(iii) the temperature during liquefying step i) is between 80° C.-95° C.;
(iv) the pH during liquefying step i) is from 4.5-5.0;
(v) the glucoamylase is of fungal origin; and
(vi) the saccharifying step (ii) and fermenting step (iii) are carried out as a simultaneous saccharification and fermentation.

97. The process of claim 1, wherein:
(i) the alpha-amylase is a bacterial alpha-amylase having a T½ (min) at pH 4.5, 85° C., 0.12 mM CaCl2) of at least 20;
(ii) the protease has a thermostability value of more than 90% determined as Relative Activity at 80° C./70° C.;
(iii) the temperature during liquefying step i) is between 80° C.-90° C.;
(iv) the pH during liquefying step i) is from 4.5-5.0;
(v) the glucoamylase is of fungal origin; and (vi) the saccharifying step (ii) and fermenting step (iii) are carried out as a simultaneous saccharification and fermentation.

98. The process of claim 1, wherein:
(i) the alpha-amylase is a bacterial alpha-amylase derived from the genus *Bacillus* having a T½ (min) at pH 4.5, 85° C., 0.12 mM CaCl2) of at least 20;
(ii) the protease has a thermostability value of more than 95% determined as Relative Activity at 80° C./70° C.;
(iii) the temperature during liquefying step i) is between 80° C.-95° C.;
(iv) the pH during liquefying step i) is from 4.5-5.0;
(v) the glucoamylase is of fungal origin; and
(vi) the saccharifying step (ii) and fermenting step (iii) are carried out as a simultaneous saccharification and fermentation.

99. The process of claim 1, wherein:
(i) the alpha-amylase is a bacterial alpha-amylase derived from the genus *Bacillus* having a T½ (min) at pH 4.5, 85° C., 0.12 mM CaCl2) of at least 20;
(ii) the protease has a thermostability value of more than 95% determined as Relative Activity at 80° C./70° C.;
(iii) the temperature during liquefying step i) is between 80° C.-90° C.;
(iv) the pH during liquefying step i) is from 4.5-5.0;
(v) the glucoamylase is of fungal origin; and
(vi) the saccharifying step (ii) and fermenting step (iii) are carried out as a simultaneous saccharification and fermentation.

100. The process of claim 1, wherein:
(i) the alpha-amylase is a bacterial alpha-amylase derived from the genus *Bacillus* having a T½ (min) at pH 4.5, 85° C., 0.12 mM CaCl2) of at least 30;
(ii) the protease has a thermostability value of more than 90% determined as Relative Activity at 80° C./70° C.;
(iii) the temperature during liquefying step i) is between 80° C.-90° C.;
(iv) the pH during liquefying step i) is from 4.5-5.0;
(v) the glucoamylase is of fungal origin; and
(vi) the saccharifying step (ii) and fermenting step (iii) are carried out as a simultaneous saccharification and fermentation.

101. The process of claim 1, wherein:
(i) the alpha-amylase is a bacterial alpha-amylase derived from the genus *Bacillus* having a T½ (min) at pH 4.5, 85° C., 0.12 mM CaCl2) of at least 40;
(ii) the protease has a thermostability value of more than 90% determined as Relative Activity at 80° C./70° C.;
(iii) the temperature during liquefying step i) is between 80° C.-90° C.;
(iv) the pH during liquefying step i) is from 4.5-5.0;
(v) the glucoamylase is of fungal origin; and
(vi) the saccharifying step (ii) and fermenting step (iii) are carried out as a simultaneous saccharification and fermentation.

102. The process of claim 1, wherein:
(i) the alpha-amylase is a bacterial alpha-amylase derived from the genus *Bacillus* having a T½ (min) at pH 4.5, 85° C., 0.12 mM CaCl2) of at least 50;
(ii) the protease has a thermostability value of more than 95% determined as Relative Activity at 80° C./70° C.;
(iii) the temperature during liquefying step i) is between 80° C.-90° C.;
(iv) the pH during liquefying step i) is from 4.5-5.0;
(v) the glucoamylase is of fungal origin; and
(vi) the saccharifying step (ii) and fermenting step (iii) are carried out as a simultaneous saccharification and fermentation.

103. The process of claim 1, wherein:
(i) the alpha-amylase is a bacterial alpha-amylase derived from the genus *Bacillus* having a T½ (min) at pH 4.5, 85° C., 0.12 mM CaCl2) of at least 60;
(ii) the protease has a thermostability value of more than 95% determined as Relative Activity at 80° C./70° C.;
(iii) the temperature during liquefying step i) is between 80° C.-90° C.;
(iv) the pH during liquefying step i) is from 4.5-5.0;
(v) the glucoamylase is of fungal origin; and
(vi) the saccharifying step (ii) and fermenting step (iii) are carried out as a simultaneous saccharification and fermentation.

104. The process of claim 1, wherein:
(i) the alpha-amylase is a bacterial alpha-amylase derived from the genus *Bacillus* having a T½ (min) at pH 4.5, 85° C., 0.12 mM CaCl2) of at least 70;
(ii) the protease has a thermostability value of more than 100% determined as Relative Activity at 80° C./70° C.;
(iii) the temperature during liquefying step i) is from 80° C.-90° C.;
(iv) the pH during liquefying step i) is from 4.5-5.0;
(v) the glucoamylase is of fungal origin; and
(vi) the saccharifying step (ii) and fermenting step (iii) are carried out as a simultaneous saccharification and fermentation.

105. The process of claim 1, wherein:
(i) the alpha-amylase is a bacterial alpha-amylase derived from the genus *Bacillus stearothermophilus* having a T½ (min) at pH 4.5, 85° C., 0.12 mM CaCl2) of at least 10;
(ii) the protease has a thermostability value of more than 100% determined as Relative Activity at 80° C./70° C.;
(iii) the temperature during liquefying step i) is between 80° C.-90° C.;
(iv) the pH during liquefying step i) is from 4.5-5.0;
(v) the glucoamylase is of fungal origin; and
(vi) the saccharifying step (ii) and fermenting step (iii) are carried out as a simultaneous saccharification and fermentation.

106. The process of claim 1, wherein:
(i) the protease has a thermostability value of more than 90% determined as Relative Activity at 80° C./70° C.;
(ii) the pH during liquefying step i) is from 4.5-5.0; and
(iii) the saccharifying step (ii) and fermenting step (iii) are carried out as a simultaneous saccharification and fermentation.

107. The process of claim 1, wherein:
(i) the protease has a thermostability value of more than 95% determined as Relative Activity at 80° C./70° C.;
(ii) the pH during liquefying step i) is from 4.5-5.0; and
(iii) the saccharifying step (ii) and fermenting step (iii) are carried out as a simultaneous saccharification and fermentation.

108. The process of claim 1, wherein:
(i) the protease has a thermostability value of more than 100% determined as Relative Activity at 80° C./70° C.; and
(ii) the pH during liquefying step i) is from 4.5-5.0; and
(iii) the saccharifying step (ii) and fermenting step (iii) are carried out as a simultaneous saccharification and fermentation.

109. The process of claim 1, wherein:
(i) the protease has a thermostability value of more than 90% determined as Relative Activity at 80° C./70° C.; and
(ii) the pH during liquefying step i) is from 4.5-5.0; and
(iii) the temperature during liquefying step i) is between 80° C.-95° C.; and
(iv) the saccharifying step (ii) and fermenting step (iii) are carried out as a simultaneous saccharification and fermentation.

110. The process of claim 1, wherein:
(i) the protease has a thermostability value of more than 90% determined as Relative Activity at 80° C./70° C.;
(ii) the pH during liquefying step i) is from 4.5-5.0;
(iii) the temperature during liquefying step i) is between 80° C.-90° C.; and
(iv) the saccharifying step (ii) and fermenting step (iii) are carried out as a simultaneous saccharification and fermentation.

111. The process of claim 1, wherein:
(i) the protease has a thermostability value of more than 95% determined as Relative Activity at 80° C./70° C.;
(ii) the pH during liquefying step i) is from 4.5-5.0;
(iii) the temperature during liquefying step i) is between 80° C.-95° C.; and
(vi) the saccharifying step (ii) and fermenting step (iii) are carried out as a simultaneous saccharification and fermentation.

112. The process of claim 1, wherein:
(i) the protease has a thermostability value of more than 95% determined as Relative Activity at 80° C./70° C.;
(ii) the pH during liquefying step i) is from 4.5-5.0;
(iii) the temperature during liquefying step i) is between 80° C.-90° C.; and
(iv) the saccharifying step (ii) and fermenting step (iii) are carried out as a simultaneous saccharification and fermentation.

113. The process of claim 1, wherein:
(i) the protease has a thermostability value of more than 100% determined as Relative Activity at 80° C./70° C.;
(ii) the pH during liquefying step i) is from 4.5-5.0;
(iii) the temperature during liquefying step i) is between 80° C.-95° C.; and
(iv) the saccharifying step (ii) and fermenting step (iii) are carried out as a simultaneous saccharification and fermentation.

114. The process of claim 1, wherein:
(i) the protease has a thermostability value of more than 100% determined as Relative Activity at 80° C./70° C.;
(ii) the pH during liquefying step i) is from 4.5-5.0;
(iii) the temperature during liquefying step i) is between 80° C.-90° C.; and
(iv) the saccharifying step (ii) and fermenting step (iii) are carried out as a simultaneous saccharification and fermentation.

\* \* \* \* \*

UNITED STATES PATENT AND TRADEMARK OFFICE
CERTIFICATE OF CORRECTION

PATENT NO. : 10,941,422 B2
APPLICATION NO. : 16/407840
DATED : March 9, 2021
INVENTOR(S) : Deinhammer et al.

Page 1 of 1

It is certified that error appears in the above-identified patent and that said Letters Patent is hereby corrected as shown below:

On the Title Page

In the Listing of Foreign Patent Documents under References Cited in item (56):
Replace "WO 2006/087692" with --WO 2006/086792--.

Signed and Sealed this
First Day of June, 2021

Drew Hirshfeld
*Performing the Functions and Duties of the*
*Under Secretary of Commerce for Intellectual Property and*
*Director of the United States Patent and Trademark Office*